(12) United States Patent
Bernstein et al.

(10) Patent No.: US 6,365,602 B1
(45) Date of Patent: Apr. 2, 2002

(54) N-SUBSTITUTED NAPHTHALENE CARBOXAMIDES AS NEUROKININ-RECEPTOR ANTAGONISTS

(75) Inventors: Peter Bernstein, Wallingford, PA (US); Robert Dedinas, Newark, DE (US); Keith Russell, Newark, DE (US); Ashokkumar Shenyl, Wilmington, DE (US)

(73) Assignee: Astra Zeneca AB (SE)

( * ) Notice: Subject to any disclaimer, the term of this patent is extended or adjusted under 35 U.S.C. 154(b) by 0 days.

(21) Appl. No.: 09/743,335

(22) PCT Filed: Jul. 7, 1999

(86) PCT No.: PCT/GB99/02178

§ 371 Date: Jan. 5, 2001

§ 102(e) Date: Jan. 5, 2001

(87) PCT Pub. No.: WO00/02859

PCT Pub. Date: Jan. 20, 2000

(30) Foreign Application Priority Data

| Jul. 10, 1998 | (GB) | 9814886 |
| Oct. 7, 1998 | (GB) | 9821699 |
| Oct. 7, 1998 | (GB) | 9821703 |
| Apr. 30, 1999 | (GB) | 9909840 |

(51) Int. Cl.[7] ................ A61K 31/445; A61K 31/505
(52) U.S. Cl. .................. 514/319; 514/269; 514/316; 514/326; 544/316; 546/205; 546/208; 546/188
(58) Field of Search ............. 546/247, 188, 546/205, 208; 544/316; 514/316, 319, 326, 269

(56) References Cited

FOREIGN PATENT DOCUMENTS

| EP | 0 428 434 A | 5/1991 |
| EP | 0 474 561 A | 3/1992 |
| EP | 0 515 240 A | 11/1992 |
| EP | 0 559 538 A | 9/1993 |
| EP | 0 630 887 A | 12/1994 |

OTHER PUBLICATIONS

Monaghan, SM 'Preparation of quaternary ammonium compounds for use as tachykinin antagonists' CA 128:205021 1998.*

Edmonds–ALT X et al: "Pharmacological Profile and Chemical Synthesis of SR 48968, A Non–Peptide Antagonist of the Neurokinin A (NK2) Receptor" Bioorganic & Medicinal Chemistry Letters, vol. 3, No. 5, Jan. 1, 1993 pp. 925–939, XP002068450 ISSN: 0960–894X compound 13.

* cited by examiner

Primary Examiner—Amelia Owens
(74) Attorney, Agent, or Firm—Richard V. Person

(57) ABSTRACT

A compound of formula I

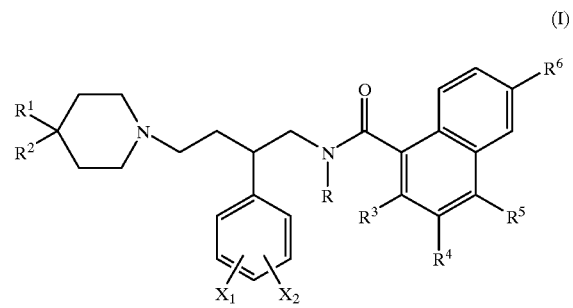

wherein: R is alkyl; $R^1$ is optionally substituted phenyl 2-oxo-tetrahydro-1(2H)-pyrimidinyl, or 2-oxo-1-piperidinyl; $R^2$ is hydrogen, alkoxy, alkanoyloxy, alkoxycarbonyl, alkanoylamino, acyl, alkyl, carbamoyl, N-alkylcarbamoyl, N,N-dialkylcarbamoyl where the alkyl groups are the same or different, hydroxy, thioacyl, thiocarbamoyl, N-alkylthiocarbamoyl, or N,N-dialkylthiocarbamoyl where the alkyl groups are the same or different. $X_1$ and $X_2$ are independently hydrogen or halo, provided that at least one of $X_1$ or $X_2$ is halo; and $R^3$, $R^4$, $R^5$ and $R^6$ are independently hydrogen, cyano, nitro, trifluoromethoxy, trifluoromethyl, or alkylsulfonyl are antagonists of at least one tachykinin receptor and are useful in the treatment of depression, anxiety, asthma, pain, inflammation, urinary incontinence and other disease conditions. Process for their preparation are described, as are compositions containing them and their use.

17 Claims, No Drawings

N-SUBSTITUTED NAPHTHALENE CARBOXAMIDES AS NEUROKININ-RECEPTOR ANTAGONISTS

This invention relates to N-substituted naphthalenecarboxamides, to pharmaceutical compositions containing such compounds, as well as to their uses and to processes for their preparation. These compounds antagonise the pharmacological actions of the endogenous neuropeptide tachykinins known as neurokinins and are useful whenever such antagonism is desired.

Tachykinins are a family of neuropeptides which share a common C-terminal amino acid sequence. Mammalian tachykinins include substance P (SP), neurokinin A (NKA) and neurokinin B (NKB). In addition there are at least two N-terminally extended forms of NKA designated as neuropeptide Y and neuropeptide K. The tachykinins are distributed widely in the peripheral and central nervous systems. At least three receptor types are known for the three principal tachykinins and based upon their relative selectivities favouring the agonists SP, NKA and NKB, the receptors are classified as NK1 (neurokinin 1), NK2 (neurokinin 2) and NK3 (neurokinin 3) receptors, respectively.

As stated above, SP, NKA and NKB are found within the central nervous system. SP is frequently co-localised with NKA. In the peripheral nervous system. NKA and SP are predominantly located in the endings of capsaicin-sensitive primary afferent neurones. A second major source of tachykinins in the periphery is in neuronal cell bodies of the myenteric and submucous plexuses of the gastrointestinal tract. Other neuronal sources include the neurones innervating the salivary glands and a small proportion of intramural neurones in the urinary bladder. Tachykinin-like immunoreactivity has been demonstrated in several other locations including the endocrine cells of the gut, parenchymal cells in the carotid body, chromaffin cells of the adrenal gland, cells of the anterior pituitary, eosinophils and vascular endothelial cells. Human lymphocytes have also been shown to produce substance P.

An important action of tachykinins is neuronal stimulation which is thought to underlie their actions in the CNS, e.g. the excitation of second-order sensory neurones in the spinal cord, the activation of spinal reflexes and induction of pain, the induction of central neurochemical responses such as stimulation of dopamine metabolism, autonomic responses and modulation of salt and water intake. In the periphery, neuronal stimulation by tachykinins leads to facilitation of transmitter release, e.g. contraction of the guinea-pig ileum is mediated partly by neurogenic mechanisms and partly by direct effects.

Tachykinins modulate neuronal activity in sympathetic ganglia. Tachykinins released from collaterals of primary afferent neurones act as mediators of slow excitatory postsynaptic potentials. Central administration of SP and NKA induce tachycardia and an increase in blood pressure in rats via activation of sympathetic nerve activity.

Tachykinins produce an endothelium-dependent vasodilatation which is measurable in vivo as a transient hypotension following i.v. infusion. The effect is mediated via $NK_1$ receptors located on endothelial cells and is thought to involve the release of nitric oxide. Tachykinin-mediated stimulation of endothelial cells also induces their proliferation, migration and angiogenesis, indicating a possible role in growth and repair. In certain blood vessels tachykinins induce vasoconstriction e.g. via the $NK_2$ and $NK_3$ receptors in the rabbit pulmonary artery and the rat hepatic portal vein respectively.

Smooth muscle contraction mediated by tachykinins appears to be predominantly due to a direct spasmogenic effect on the muscle. The combination of this direct effect with the tachykinin-stimulated release of tachkinins from nerve endings forms the basis for their status as excitatory neurotransmitters in the airways, intestine and urinary tract. In human bronchus, urinary bladder, urethra and colon the $NK_2$ receptor is the mediator of this stimulatory response. Tachykinins can also induce smooth muscle relaxation via a $NK_1$ receptor-mediated stimulation of prostanoid production in airway epithelial cells.

SP, NKA and/or NAB have been implicated in the pathology of numerous diseases including asthma, allergic rhinitis, chronic obstructive pulmonary disease (COPD), pulmonary hypertension, airway reactivity, cough, cold, urticaria, inflammation (including neurogenic inflammation), pain, various pain states (including neuropathic pain, visceral pain, ocular pain), migraine, tension headache, angiogenesis, rheumatoid arthritis, psychoses including depression and anxiety, including major depressive disorders, major depressive disorders with anxiety, cognitive disorders, movement disorder, bipolar disorders, substance use disorders, stress disorders, sleep disorders, motion sickness, panic attacks and social phobia, mania, hypomania, aggressive behaviour, pre-menstrual tension and associated appetite disorders, memory loss, emesis, (including ondansetron-resistance emesis), hypertension, oedema, Huntingdon's disease, Alzheimer's disease, schizophrenia, neuronal injury such as stroke, epilepsy, spinal cord disorder, Parkinson's Disease, gastrointestinal-hypermotility, 'gastric asthma', gastroesphageal reflux disease, Crohn's disease, gastric emptying disorders. ulcerative colitis, irritable bowel syndrome, inflammatory bowel syndrome, bladder hypermotility, urinary incontinence, cystitis, obesity, bulimia nervosa, cancer, parathyroid hormone deficiency, bone loss, mammalian hair growth, sexual dysfunction, tardive dyskinesia, renal disorders, skin disorders and itch (for example atopic dermatitis and psoriasis).

Examples of reviews covering the use of tachykinin antagonists in various of these disease conditions are: Maggi, C A., Patacchini, R, Rovero, P and Giachetti, A (1993)) Tachykinin receptors and tachykinin receptor antagonists *J Auton, Pharmacol*. 13, 23–93; McLean, S. (1996), Nonpeptide antagonists of the $NK_1$ tachykinin receptor *Med. Res. Rev*. 16, 297–317; Raffa R B, Possible role(s) of neurokinins in CNS development and neurodegenerative or other disorders. *Neuroscience & Biobehavioral Reviews*. 22(6): 789–813, 1998 October; Holzer P, Implications of tachykinins and calcitonin gene-related peptide in inflammatory bowel disease *Digestion*. 59(4): 269–83, 1998 July–August; Maggi C A., Tachykinins as peripheral modulators of primary afferent nerves and visceral sensitivity. *Pharmacological Research*. 36(2): 153–69, 1997 August; Kudlacz E M, Expert Opinion. Invest. Drugs (1998), 7(7), 1055–62; and von Sprecher et al, Drugs (1998), 1(1), 73–91.

The N-substituted naphthalenecarboxamide compounds of the present invention are antagonists of at least one of the tachykinin receptors and are of value in treating implicated disease conditions. In particular the compounds have a high degree of NK1 and/or NK2 receptor antagonist activity. Additionally, by manipulation of the substituents on the naphthalene and piperidine rings of the formula (I) hereinbelow, the ratio of activity at the NK1 and NK2 receptors can be modified, affording compounds that are predominantly active at either NK1 or NK2 receptors, or affording compounds with a balanced activity and, as such, are particularly useful when combined antagonism of both receptors is desired. In particular preferred compounds of the present invention also possess a high degree of NK1 and/or NK2 antagonism upon oral administration.

Accordingly, the present invention provides the compounds of the formula (I):

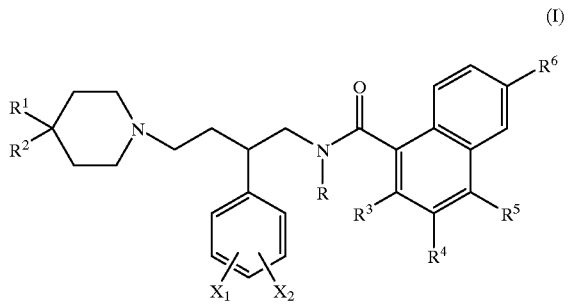

wherein:
R is alkyl; $R^1$ is optionally substituted phenyl, 2-oxo-tetrahydro-1(2H)-pyrimidinyl, or 2-oxo-1-piperidinyl;
$R^2$ is hydrogen, alkoxy, alkanoyloxy, alkoxycarbonyl, alkanoylamino, acyl, alkyl, carbamoyl, N-alkylcarbamoyl, N,N-dialkylcarbamoyl where the alkyl groups are the same or different, hydroxy, thioacyl, thiocarbamoyl, N-alkylthiocarbamoyl, or N,N-dialkylthiocarbamoyl where the alkyl groups are the same or different;
$X_1$ and $X_2$ are independently hydrogen or halo, provided that at least one of $X_1$ or $X_2$ is halo; and
$R^3$ $R^4$ $R^5$ and $R^6$ are independently hydrogen, cyano, nitro, trifluoromethoxy, trifluoromethyl, or alkylsulfonyl, provided that at least one of $R^3$, $R^4$, $R^5$, and $R^6$ is not hydrogen;
and pharmaceutically acceptable salts and in vivo hydrolysable precursors thereof.

"Alkyl" means a saturated aliphatic hydrocarbon group which may be straight or branched and having about 1 to about 20 carbon atoms in the chain, Branched means that one or more lower alkyl groups such as methyl, ethyl or propyl are attached to a linear alkyl chain.

Preferred alkyl groups are the lower alkyl groups which are those alkyl groups having from 1 to about 6 carbons, for example $C_{1-6}$alkyl. "Acyl" means an alkylcarbonyl group for example $C_{1-6}$alkanoyl. "Thioacyl" means an alkylthiocarbonyl group for example $C_{1-6}$alkylthiocarbonyl.

R is alkyl for example $C_{1-6}$alkyl such as methyl, ethyl or n-propyl. Preferably R is methyl so that in one aspect the present invention provides the compounds of the formula (I) wherein R is methyl and the pharmaceutically acceptable salts thereof. In a further aspect the present invention provides the compounds of the formula (I) wherein R is methyl, $R^1$, $X_1$ and $X_2$ are as hereinabove defined; and $R^2$ is hydrogen, acyl, alkyl, carbamoyl, N-alkylcarbamoyl. N,N-dialkylcarbamoyl, hydroxy, thioacyl, thiocarbamoyl, N-alkylthiocarbamoyl or N,N-dialkylthiocarbamoyl, and the pharmaceutically acceptable salts thereof.

In one aspect $R^1$ is optionally substituted phenyl. Suitable substituents for the phenyl ring include:
alkyl such as $C_{1-6}$alkyl for example methyl or ethyl; alkylthio such as $C_{1-6}$alkylthio for example methylthio or ethylthio; alkylsulfinyl such as $C_{1-6}$alkylsulfinyl for example methylsulfinyl, ethylsulfinyl or propylsulfinyl; alkylsulfonyl such as $C_{1-6}$alkylsulfonyl for example methylsulfonyl or ethylsulfonyl; hydroxy; alkoxy such as $C_{1-6}$alkoxy for example methoxy or ethoxy; amino; halo for example fluoro, chloro, bromo or iodo; carboxy; alkoxycarbonyl such as $C_{1-6}$alkoxycarbonyl for example methoxycarbonyl; nitro; alkylamino such as $C_{1-6}$alkylamino for example methylamino or ethylamino; di-alkylamino (wherein the alkyl groups may be the same or different) such as di-$C_{1-6}$alkylamino for example dimethylamino; trifluoromethyl; carbamoyl; alkylcarbamoyl such as $C_{1-6}$alkylcarbamoyl for example methylcarbamoyl; di-alkylcarbamoyl (wherein the alkyl groups may be the same or different) such as di-$C_{1-6}$alkylcarbamoyl for example dimethylcarbamoyl; trifluoromethylthio; trifluoromethylsulfinyl; trifluoromethylsulfonyl; alkanesulfonamido such as $C_{1-6}$alkanesulfonamido for example methanesulfonamido; alkanoyl such as $C_{1-6}$alkanoyl for example acetyl; succinamido; N-alkoxy, N-alkylamino such as N—$C_{1-6}$alkoxy, N—$C_{1-6}$alkylamino for example N-methoxy, N-methylamino; alkanoylamino such as $C_{1-6}$alkanoylamino for example acetamido or propionamido; ureido; alkylureido such as $C_{1-6}$alkylureido for example methylureido (MeNHCONH—) di-alkylureido such as di-$C_{1-6}$alkylureido for example dimethylureido; alkylsulfonyloxy such as $C_{1-6}$alkylsulfonyloxy for example methylsulfonyloxy; 2-oxopyrrolidino; N-oxo-N,N-dialkylamino such as N-oxo-N,N-di-$C_{1-6}$alkylamino for example N-oxo-N,N-dimethylamino; alkoxycarbonylamino such as $C_{1-6}$alkoxycarbonylamino for example methoxycarbonylamino; alkoxycarbonylcarbonylamino such as $C_{1-6}$alkoxycarbonylcarbonylamino for example methoxycarbonylcarbonylamino; alkylcarbamoylalkoxy such as $C_{1-6}$alkylcarbamoyl$C_{1-6}$alkoxy for example methylcarbamoyl methoxy; dialkylcarbamoyl$C_{1-6}$alkoxy such as di-$C_{1-6}$alkylcarbamoylalkoxy for example dimethylcarbamoylmethoxy; and $C_{1-6}$alkyl for example methyl substituted by any of the hereinabove substituents for example methylsulfinylmethyl.

In one aspect $R^1$ is a phenyl group substituted in the ortho-position and in a preferred aspect the ortho-substituent is $C_{1-6}$alkylthio for example methylthio; $C_{1-6}$alkylsulfinyl for example methylsulfinyl, ethylsulfinyl or propylsulfinyl; $C_{1-6}$alkylsulfonyl for example methylsulfonyl or ethylsulfonyl; trifluoromethylthio; trifluoromethylsulfinyl; $C_{1-6}$alkanesulfonamido for example methanesulfonamido; $C_{1-6}$alkanoyl for example acetyl or propionyl; $C_{1-6}$alkoxycarbonyl for example methoxycarbonyl; succinamido; carbamoyl; $C_{1-6}$alkylcarbamoyl for example methylcarbamoyl; di-$C_{1-6}$alkylcarbamoyl for example dimethylcarbamoyl; hydroxy; $C_{1-6}$alkoxy, $C_{1-6}$alkylcarbamoyl for example N-methoxy, N-methylcarbamoyl; $C_{1-6}$alkanoylamino for example acetylamino; ureido, $C_{1-6}$alkylureido for example methylureido; di-$C_{1-6}$ alkylureido for example dimethylureido; amino; $C_{1-6}$alkylamino for example methylamino or ethylamino; di-$C_{1-6}$alkylamino for example dimethylamino; $C_{1-6}$alkyl-sulfonyloxy for example methylsulfonyloxy; 2-oxopyrrolidino; N-oxo-N,N-di-$C_{1-6}$alkylamino for example N-oxo-N,N-dimethylamino; $C_{1-6}$alkoxycarbonylamino for example methoxycarbonylamino; $C_{1-6}$alkoxycarbonylcarbonylamino for example methoxycarbonylcarbonylamino; $C_{1-6}$alkylcarbamoylalkoxy for example methylcarbamoylmethoxy; di-$C_{1-6}$alkylcarbamoylalkoxy for example dimethylcarbamoylmethoxy; or methylsulfinylmethyl. In addition to the ortho-substituent, the phenyl group may have further substituents.

In a further aspect the ortho-substituent is $C_{1-6}$alkylthio for example methylthio; $C_{1-6}$alkylsulfinyl for example methylsulfinyl, ethylsulfinyl or propylsulfinyl; $C_{1-6}$alkylsulfonyl for example methylsulfonyl or ethylsulfonyl; trifluoromethylthio; trifluoromethylsulfinyl; $C_{1-6}$alkanesulfonamido for example methanesulfonamido; $C_{1-6}$alkanoyl for example acetyl or propionyl; $C_{1-6}$alkoxycarbonyl for example methoxycarbonyl; succinamido; carbamoyl; $C_{1-6}$alkylcarbamoyl for example methylcarbamoyl; di-$C_{1-6}$alkylcarbamoyl for example dimethylcarbamoyl; $C_{1-6}$alkoxy, $C_{1-6}$alkylcarbamoyl for example N-methoxy, N-methylcarbamoyl; $C_{1-6}$alkanoylamino for example acetylamino; ureido, $C_{1-6}$alkylureido for example methylureido; di-$C_{1-6}$alkylureido for example dimethylureido; amino; $C_{1-6}$alkylamino for example methylamino or ethylamino; or di-$C_{1-6}$alkylamino for example dimethylamino. In addition to the ortho-substituent, the phenyl group may have further substituents.

Suitable further substituents, which are optional, for the ortho-substituted phenyl ring include $C_{1-6}$alkyl for example methyl or ethyl; $C_{1-6}$alkylthio for example methylthio or ethylthio; $C_{1-6}$alkylsulfinyl for example methylsulfinyl, ethylsulfinyl or propylsulfinyl; $C_{1-6}$alkylsulfonyl for example methylsulfonyl or ethylsulfonyl; $C_{1-6}$alkoxy for example methoxy, ethoxy or propoxy; halo for example bromo, fluoro, chloro or iodo; carboxy; $C_{1-6}$alkoxycarbonyl for example methoxycarbonyl; $C_{1-6}$alkanoyl for example acetyl or propionyl; nitro; amino; $C_{1-6}$alkylamino for example methylamino or ethylamino; di-$C_{1-6}$alkylamino where the alkyl groups may be the same or different, for example dimethylamino; trifluoromethyl; $CF_3S(O)_x$ wherein x is 0 to 2, for example trifluoromethylthio, trifluoromethylsulfinyl or trifluoromethylsulfonyl; $C_{1-6}$alkanoylamino for example acetylamino or propionylamino; $C_{1-6}$alkylsulphonamido for example methylsulphonamido; ureido; $C_{1-6}$alkylureido for example methylureido (MeNHCONH—), di-$C_{1-6}$alkylureido for example dimethylureido ($Me_2NCONH$—); carbamoyl; $C_{1-6}$alkylcarbamoyl for example methylcarbamoyl; di-$C_{1-6}$alkylcarbamoyl where the alkyl groups may be the same or different, for example dimethylcarbamoyl; and $C_{1-6}$alkyl for example methyl substituted by any of the hereinabove substituents. Another suitable further substituent for the ortho-substituted ring is hydroxy.

In one aspect, suitable further substituents for a phenyl group already substituted in the ortho-position are $C_{1-6}$alkyl, $C_{1-6}$alkylsulfinyl, $C_{1-6}$alkylsulfonyl, $C_{1-6}$alkoxy, amino, halo, carboxy, $C_{1-6}$alkoxycarbonyl, nitro, N—$C_{1-6}$alkylamino, N,N-di-$C_{1-6}$alkylamino (where the alkyl groups may be the same or different), trifluoromethyl, $C_{1-6}$alkylthio, carbamoyl, N—$C_{1-6}$alkylcarbamoyl and N,N-di-$C_{1-6}$alkylcarbamoyl (where the alkyl groups may be the same or different), $C_{1-6}$alkanoyl, $C_{1-6}$alkanesulfonamido, trifluoromethylthio, trifluoromethylsulfinyl, hydroxy, ureido, $C_{1-6}$alkylureido and di-$C_{1-6}$alkylureido. Preferably these further substituents are at the 4-position of the phenyl group.

Preferred values for the ortho-substituent are methylsulfinyl, ethylsulfinyl, propylsulfinyl, methylsulfonyl, trifluoromethylthio, trifluoromethylsulfinyl, methanesulfonamido, acetyl, methoxycarbonyl, succinamido, carbamoyl, methylcarbamoyl, dimethylcarbamoyl, N-methoxy, N-methylcarbamoyl, acetylamino, ureido, methylureido, dimethylureido, amino, methylamino and dimethylamino.

In particular the ortho-substituent is methylsulfinyl, methylsulfonyl, methylureido, dimethylureido, amino, methylamino or dimethylamino. Of these methylsulfinyl is particularly preferred.

Favourably the ortho-substituted phenyl ring is not substituted further or is substituted by up to three optional substituents. In particular the ortho-substituted phenyl ring is not substituted further or is substituted at the 4-position, that is the position para- to the bond with the piperidine ring, so forming a 2, 4-disubstituted phenyl group, preferably a 2-MeSO, 4-substituted phenyl group.

Preferred substituents, if present, for the ortho-substituted phenyl ring, are methyl, methoxy, acetyl, acetylamino, methoxycarbonyl, methanesulfonylamino, methylsulfinyl, methylsulfonyl, trifluoromethyl, trifluoromethylthio, trifluoromethylsulfinyl, bromo. fluoro, chloro, hydroxy, carbamoyl, methylcarbamoyl, dimethylcarbamoyl, methylureido and dimethylureido. In particular these preferred substituents may be at the 4-position of the phenyl ring.

A preferred class of compounds is that wherein $R^1$ is of the formula (Ia):

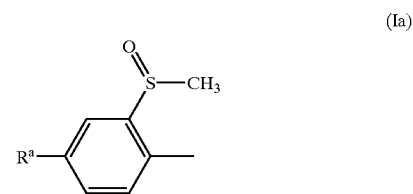

(Ia)

wherein $R^a$ is hydrogen, $C_{1-6}$alkyl, $C_{1-6}$alkylsulfinyl, $C_{1-6}$alkylsulfonyl, $C_{1-6}$alkoxy, amino, halo, carboxy, $C_{1-6}$alkanoyloxy, nitro, N—$C_{1-6}$alkyl amino, di-$C_{1-6}$ alkylamino, trifluoromethyl. $C_{1-6}$alkylthio, carbamoyl, $C_{1-6}$alkylcarbamoyl and di-$C_{1-6}$alkylcarbamoyl; and $R^2$ is hydrogen. More preferably, $R^a$ is hydrogen, $C_{1-6}$alkoxy for example methoxy or ethoxy, halo for example bromo, chloro or fluoro, $C_{1-6}$alkylsulfinyl for example methylsulfinyl or carboxy.

In one aspect $R^a$ is hydrogen or $C_{1-6}$alkoxy.
In another aspect $R^a$ is hydrogen, $C_{1-6}$alkoxy or halo.
More particularly $R^a$ is hydrogen, methoxy or fluoro.
In a particularly preferred aspect $R^a$ is hydrogen.
In another particularly preferred aspect $R^a$ is methoxy.
The compounds of the invention have a number of chiral centres. It is preferred that the ortho-methylsulfinyl substituent, if present, has the stereochemistry depicted in formula (Ib):

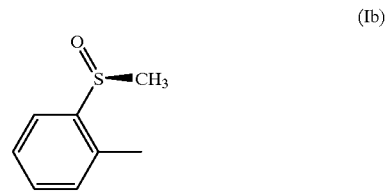

(Ib)

That is the S-stereochemistry according to the Cahn-Prelog-Ingold sequence rules. Preferred values for $R^1$ are therefore 2(S)-methylsulfinylphenyl and 4-methoxy-2(S)-methylsulfinylphenyl.

In another aspect $R^1$ is 2-oxotetrahydro-1(2H)-pyrimidinyl.
In a further aspect $R^1$ is 2-oxo-1-piperidinyl.
$R^2$ is hydrogen; acyl such as $C_{1-6}$alkanoyl for example acetyl or propionyl; alkyl such as $C_{1-6}$alkyl for example methyl or ethyl; carbamoyl; N-alkylcarbamoyl such as $C_{1-6}$alkylcarbamoyl for example methylcarbamoyl or ethylcarbamoyl; N,N-dialkylcarbamoyl such as di-$C_{1-6}$ alkylcarbamoyl for example dimethylcarbamoyl; hydroxy; thioacyl such as $C_{1-6}$alkylthiocarbonyl for example methylthiocarbonyl; thiocarbamoyl ($NH_2CS$—);

N-alkylthiocarbamoyl such as $C_{1-6}$alkylthiocarbamoyl for example methylthiocarbamoyl (MeNHCS—); N,N-dialkylthiocarbamoyl such as di-$C_{1-6}$alkylthiocarbamoyl for example dimethylthiocarbamoyl (Me$_2$NCS—); alkoxy such as $C_{1-6}$alkoxy for example methoxy or ethoxy; alkanoyloxy such as $C_{1-6}$ alkanoyloxy for example acetyloxy or propionoxy; alkoxycarbonyl such as $C_{1-6}$alkoxycarbonyl for example methoxycarbonyl or ethoxycarbonyl; or alkanoylamino such as $C_{1-6}$alkanoylamino for example acetylamino.

In one aspect $R^2$ is hydrogen, acyl, alkyl, carbamoyl, N-alkylcarbamoyl, N,N-dialkylcarbamoyl, hydroxy, thioacyl, thiocarbamoyl. N-alkylthiocarbamoyl or N,N-dialkylthiocarbamoyl.

in a preferred aspect $R^2$ is hydrogen, hydroxy, methoxycarbonyl, methylcarbamoyl or dimethylcarbamoyl. When $R^1$ is optionally substituted phenyl, preferably $R^2$ is hydrogen or hydroxy, most preferably hydrogen. When $R^1$ is 2-oxo-tetrahydro-1-(2H)-pyrimidinyl or 2-oxo-1-piperidinyl, preferably $R^2$ is hydrogen, methoxycarbonyl, methylcarbamoyl or dimethylcarbamoyl. In another aspect when $R^1$ is 2-oxo-tetrahydro-1-(2H)-pyrimidinyl or 2-oxo-1-piperidinyl, $R^2$ is hydrogen or N—$C_{1-6}$alkylcarbamoyl for example methylcarbamoyl.

Ph—$X_1$, $X_2$ is phenyl mono-or di-substituted by halo. Preferably halo is chloro or fluoro and in particular Ph—$X_1$, $X_2$ is 4-chloro, 4-fluoro, 3,4-difluoro or 3,4-dichloro. Of these 3,4-dichloro is most preferred.

$R^3$, $R^4$, $R^5$ and $R^6$ are independently hydrogen, cyano, nitro, trifluoromethoxy, trifluoromethyl or alkylsulfonyl (for example $C_{1-6}$alkylsulfonyl) with the proviso that at least one of $R^3$-$R^6$ is not hydrogen, Preferably $R^3$ is hydrogen. Preferably $R^4$ is cyano. nitro or methylsulfonyl. Preferably $R^5$ is hydrogen or cyano. Preferably $R^6$ is hydrogen, cyano or nitro.

More preferably $R^3$ and $R^6$ are hydrogen, $R^4$ is cyano or nitro, and $R^5$ is hydrogen or cyano.

Most preferably $R^3$, $R^5$ and $R^6$ are hydrogen and $R^4$ is cyano or nitro, in particular cyano so forming the 3-cyano-naphth-1-yl group.

The compounds of the present invention possess a number of chiral centres, at —CH(Ph—$X_1$, $X_2$)—, and possibly in the optional substituents (for example the MeSO— substituent) on the phenyl groups if present. The present invention covers all isomers, diastereoisomers, atropisomers and mixtures thereof that antagonise tachykinins.

The preferred configuration at —CH(Ph—$X_1$, $X_2$)— is shown in formula (Ic) hereinbelow:

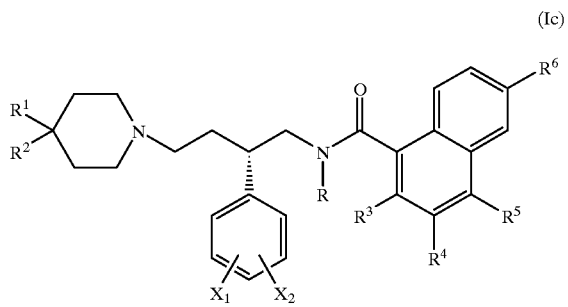

(Ic)

A preferred class of compounds is that of the formula (II):

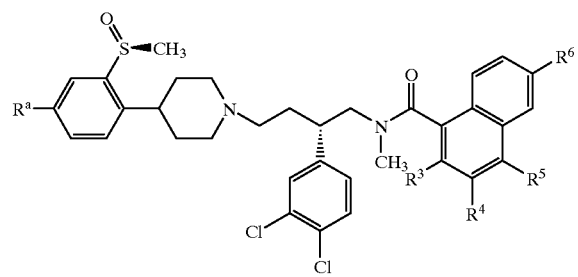

wherein $R^a$ is hydrogen, $C_{1-6}$alkoxy, halo, $C_{1-6}$alkylsulfinyl or carboxy; $R^3$ is hydrogen; $R^4$ is cyano or nitro; $R^5$ is hydrogen or cyano; and $R^6$ is hydrogen. In particular $R^a$ is hydrogen, methoxy or fluoro; $R^3$, $R^5$ and $R^6$ are all hydrogen and $R^4$ is cyano or nitro, preferably cyano.

Particular compounds of this invention include those of the Examples hereinbelow.

Pharmaceutically acceptable salts of the compounds of the formula (I) include those made with inorganic or organic acids which afford a physiologically acceptable anion, such as with, for example, hydrochloric, hydrobromic, sulfuric, phosphoric, methanesulfonic, sulfamic, para-toluenesulfonic, acetic, citric, lactic, tartaric, malonic, fumaric, maleic, maleic, ethanesulfonic, benzenesulfonic, cyclohexylsulfamic, salicyclic and quinic acids.

In vivo hydrolysable precursors include in vivo hydrolysable esters, amides and carbamates which hydrolyse in the animal (e.g. human) body to produce the parent compound. Such precursors, for example esters, amides and carbamates, can be identified by administering, for example intravenously to a test animal, the compound under test and by subsequently examining the test animal's body fluids. Suitable in vivo hydrolysable precursors include esters of carboxy (RXOOC—) and of hydroxy (RYCOO—).

In order to use a compound of the formula (I) or a pharmaceutically acceptable salt or an in-vivo hydrolysable precursor thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in-vivo hydrolysable precursor and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt or an in vivo hydrolysable precursor thereof. In another example, for administration by inhalation, a compound of the formula (I) or a pharmaceutically acceptable salt or an in vivo hydrolysable precursor thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt or an in vivo hydrolysable precursor thereof may be used.

Therefore in a further aspect, the present invention provides a compound of the formula (I) or a pharmaceutically acceptable salt or an in vivo hydrolysable precursor thereof for use in a method of therapeutic treatment of the human or animal body.

In yet a further aspect the present invention provides a method of treating a disease condition wherein antagonism of at least one tachykinin receptor is beneficial which comprises administering to a patient in need thereof an effective amount of a compound of the formula (I) or a pharmaceutically acceptable salt or an in vivo hydrolysable precursor thereof. The present invention also provides the use of a compound of the formula (I) or a pharmaceutically acceptable salt or an in vivo hydrolysable precursor thereof in the preparation of a medicament for use in a disease condition wherein antagonism of at least one tachykinin receptor is beneficial. In particular the present invention provides a method of treating a disease condition wherein antagonism of the NK1 and/or NK2 receptors is beneficial.

In particular the present invention provides a method of treating asthma which comprises administering to a patient in need thereof an effective amount of a compound of the formula (I) or a pharmaceutically acceptable salt or an in vivo hydrolysable precursor thereof.

In particular the present invention provides a method of treating chronic obstructive pulmonary disease which comprises administering to a patient in need thereof an effective amount of a compound of the formula (I) or a pharmaceutically acceptable salt or an in vivo hydrolysable precursor thereof.

In particular the present invention provides a method of treating pain which comprises administering to a patient in need thereof an effective amount of a compound of the formula (I) or a pharmaceutically acceptable salt or an in vivo hydrolysable precursor thereof.

In particular the present invention provides a method of treating depression which comprises administering to a patient in need thereof an effective amount of a compound of the formula (I) or a pharmaceutically acceptable salt or an in vivo hydrolysable precursor thereof.

In particular the present invention provides a method of treating urinary incontinence which comprises administering to a patient in need thereof an effective amount of a compound of the formula (I) or a pharmaceutically acceptable salt or an in vivo hydrolysable precursor thereof.

In another aspect the present invention provides a process for preparing a compound of the formula (I) or a pharmaceutically acceptable salt or an in vivo hydrolysable precursor thereof which process comprises:

a) reacting a compound of the formula (III) with a compound of the formula (IV):

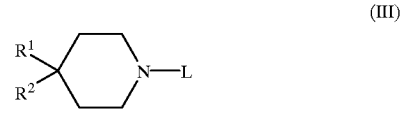

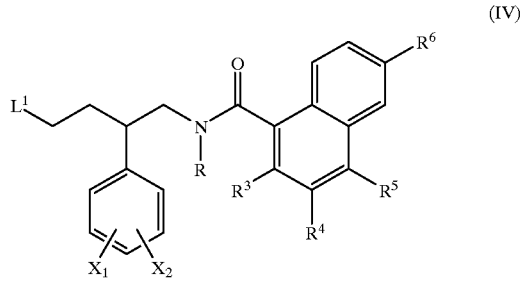

wherein R, $R^1$–$R^6$, $X_1$ and $X_2$ are as hereinbefore defined; and L and $L^1$ are groups such that reductive amination of the compounds of the formulae (III) and (IV) forms a N—C bond; or b) reacting a compound of the formula (V) with a compound of the formula (VI):

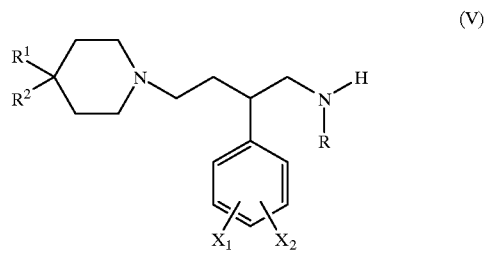

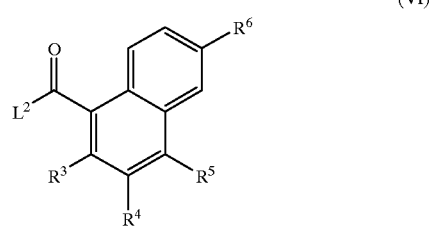

wherein $R^1$–$R^6$, $R^2$, $X_1$ and $X_2$ are as hereinbefore defined; and $L^2$ is a leaving group; wherein any other functional group is protected, if necessary, and:

i) removing any protecting groups;
ii) optionally forming a pharmaceutically acceptable salt or in vivo hydrolysable precursor.

Protecting groups may in general be chosen from any of the groups described in the literature or known to the skilled chemist as appropriate for the protection of the group in question, and may be introduced and removed by conventional methods; see for example: Theodora W. Greene et al., Wiley (1991), Protective Groups in Organic Chemistry; J F W McOmie, Plenum Press (1973) and Kocienski, Philip J, Georg Thieme Verlag (1994), Protecting Groups. Methods of removal are chosen so as to effect removal of the protecting group with minimum disturbance of groups elsewhere in the molecule.

It will also be appreciated that certain of the various optional substituents in the compounds of the formula (I) may be introduced by standard aromatic substitution reactions or generated by conventional functional group modifications either prior to or immediately following the processes described hereinabove. The reagents and reaction conditions for such procedures are well known in the chemical art.

Pharmaceutically acceptable salts may be prepared from the corresponding acid in conventional manner. Non-pharmaceutically acceptable salts may be useful as intermediates and as such are another aspect of the present invention.

In vivo hydrolysable precursors may be prepared from the corresponding functional derivative in conventional manner at any convenient stage of the synthesis.

It is well known in the art how to prepare optically-active forms (for example by resolution of the racemic form or by synthesis from optically-active starting materials) and how to determine the tachykinin antagonist properties by the standard tests known in the art and those described hereinafter.

The compounds of the formulae (III) and (IV) are reacted under conditions of reductive amination. Typically in the compounds of the formula (III) L is hydrogen.

Typically in the compounds of the formula (IV) $L^1$ is an oxo group so forming an aldehyde moiety (i.e. $L^1$ and the carbon atom to which is joined are OHC—). The reaction is typically performed at a non-extreme temperature, for example 0–100° C., suitably ambient temperature in a substantially inert solvent for example methanol or dichloromethane. Typical reducing agents include borohydrides such as sodium cyanoborohydride.

In an alternative, in the compounds of the formula (IV), $L^1$ is a leaving group such as halo for example chloro or bromo or is a sulfonate for example methanesulfonate or p-toluenesulfonate. Such compounds are reacted with compounds of the formula (III) wherein L is hydrogen in the presence of a base.

The compounds of the formula (III) are known or may be prepared in conventional manner. The compounds of the formula (IV) may be prepared in a conventional manner. For example when $L^1$ is oxo, compounds of the formula (IV) may be prepared by oxidising a compound of the formula (VII):

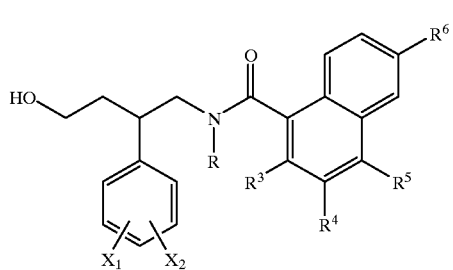

(VII)

wherein $X^1$, $X^2$, R and $R^3$–$R^6$ are as hereinbefore described. Suitable oxidation conditions include Swern conditions for example oxidation with oxalyl chloride in the presence of dimethylsulfoxide. The compounds of the formula (IV) wherein $L^1$ is a leaving group may be prepaed in conventional manner from a compound of the formula (VII).

The compounds of the formula (VII) may be prepared, for example by reacting a compound of the formula (VI) with a compound of the formula (VIII):

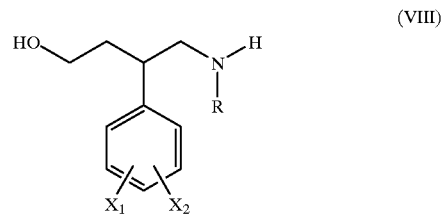

(VIII)

wherein R, $X_1$ and $X_2$ are as hereinbefore defined under conventional acylation conditions The compounds of the formulae (V) and (VI) may be reacted under conventional acylation conditions wherein the compound of formula (VI) is an acid or an activated acid derivative. Typical activated acid derivatives are well known in the literature. They may be formed in situ from the acid or they may be prepared, isolated and subsequently reacted. Typically $L^2$ is chloro thereby forming the acid chloride. Typically the acylation reaction is performed in the presence of a non-nucleophilic base, for example di-isopropylethylamine, in a substantially inert solvent at a non-extreme temperature. The compounds of the formula (V) are known or may be prepared in a conventional manner.

The compounds of the formulae (IV) and (VII) are not only useful intermediates but also have good tachykinin antagonist activity, in particular at the NK1 receptor.

Therefore in another aspect, the present invention provides a compound of the formula (IV) or (VII) or a pharmaceutically salt or in vivo hydrolysable precursor thereof.

More particularly the present invention provides a compound of the formula (IX):

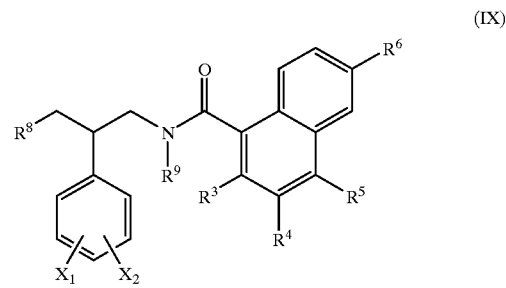

(IX)

wherein $X^1$, $X^2$ and $R^3$–$R^6$ are as hereinbefore defined;
$R^8$ is —CHO; —CH$_2$OR$^{10}$ wherein $R^{10}$ is hydrogen or an ester thereof or $C_{1-6}$alkyl; and $R^9$ is hydrogen or a group R as hereinbefore defined;
or a pharmaceutically acceptable salt or in vivo hydrolysable precursor thereof.

Suitably $R^9$ is $C_{1-6}$alkyl for example methyl.

In one aspect $R^8$ is aldehydo (—CHO) or is a derivative thereof. A suitable derivative is an acetal, for example of the formula ($R^b$O)CH(OR$^c$)— wherein $R^b$ and $R^c$ are independently selected from $C_{1-6}$alkyl or together form a $C_{2-4}$methylene chain thus forming a dioxo ring. More suitably $R^b$ and $R^c$ have the same value and are both methyl or are both ethyl.

In a further aspect $R^8$ is —CH$_2$OR$^{10}$ wherein $R^{10}$ is hydrogen or $C_{1-6}$alkyl. Preferably $R^{10}$ is hydrogen, methyl or ethyl and in particular $R^{10}$ is hydrogen. In yet a further aspect $R^{10}$ may represent an ester forming group for example forming a group of the formula —$CH_2OCOR^d$ wherein $R^d$ is $C_{1-6}$alkyl for example methyl, aryl for example phenyl or aryl$C_{1-6}$alkyl for example benzyl.

Acetals of —CHO and esters of hydroxymethyl (HOCH$_2$—) may be prepared in standard manner.

Preferred values of $X^1$, $X^2$, R and $R^3$–$R^6$ are as described hereinabove for compounds of the formula (I). Accordingly in the compounds of the formula (IX), preferably —Ph$X_1X_2$— is 3,4-dichlorophenyl and R is methyl. A preferred class of compounds is that of the formula (X):

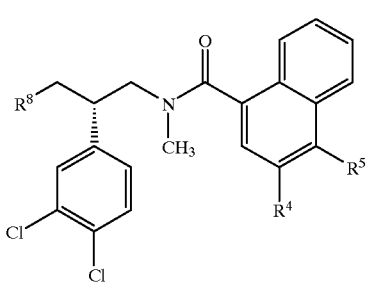

(X)

wherein $R^8$ is —CHO or an acetal thereof such as $(CH_3O)_2CH$—; or an ester thereof for example acetoxymethyl, or $R^8$ methoxymethyl or ethoxymethyl; $R^4$ is cyano or nitro; and $R^5$ is hydrogen or cyano. In particular $R^5$ is hydrogen and $R^4$ is cyano or nitro, most preferably cyano, and $R^8$ is —CHO or —$CH_2OH$.

These compounds antagonise the NK1 receptor in particular and therefore are particularly beneficial in treating disease conditions mediated through such receptors, for example depression, anxiety, emesis, pain and other disease conditions identified in the literature.

The compounds of the formulae (IX) and (X) may be formulated and administered as described hereinbefore in relation to the compounds of the formula (I).

The following biological test methods, data and Examples serve to illustrate and further describe the invention.

The utility of a compound of the invention or a pharmaceutically acceptable salt or in vivo hydrolysable precursor thereof (hereinafter, collectively referred to as a "Compound") may be demonstrated by known tests and by clinical studies.

SP Receptor Binding Assay (Test A)

The ability of a Compound of the invention to antagonize the binding of SP at the NK1 receptor may be demonstrated with an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.*, 1991, 180, 1110–1117; and the NK1 receptor was expressed in Mouse Erythroleukemia (MEL) cells using a procedure similar to that described in Test B below.

In general, the Compounds of the invention having NK1 antagonist activity which were tested demonstrated statistically significant binding activity in Test A with a $K_i$ of 1 microM or much less typically being measured.

Neurokinin A (NKA) Receptor Binding Assay (Test B)

The ability of a Compound of the invention to antagonize the binding of NKA at the NK2 receptor may be demonstrated with an assay using the human NK2 receptor expressed in Mouse Erythroleukemia (MEL) cells, as described in: Aharony, D., et al. "Isolation and Pharmacological Characterization of a Hamster Neurokinin A Receptor cDNA" *Molecular Pharmacology*, 1994, 45, 9–19.

The selectivity of a Compound for binding at the NK1 and the NK2 receptors may be shown by determining its binding at other receptors using standard assays, for example, one using a tritiated derivative of NKB in a tissue preparation selective for NK3 receptors. In general, the Compounds of the invention having NK2 antagonist activity which were tested demonstrated statistically significant binding activity in Test A and Test B with a $K_i$ of 1 microM or much less typically being measured.

Neurokinin B (NKB) Receptor Binding Assay (Test C)

The ability of a Compound of the invention to antagonise the binding of a selective NKB receptor ligand at the NK3 receptor may be demonstrated with an assay using the human NK3 receptor, cloned from human brain and expressed in Mouse Erythroleukemia (MEL) cells. Human NK3 receptor was expressed in MEL cells with a similar procedure to that described for the human NK2 receptor in: Aharony, D., et al. "Isolation and Pharmacological Characterization of a Hamster Neurokinin A Receptor cDNA" *Molecular Pharmacology*, 1994, 45, 9–19.

The selectivity of a Compound for binding at the NK1 and the NK2 receptors may be shown by determining its binding at other receptors using standard assays, for example, one using a tritiated derivative of NKB in a clonal cells expressing the human NK3 receptors. In general, the Compounds of the invention having NK2 antagonist activity which were tested demonstrated statistically significant binding activity in Test A and Test B with a $K_i$ of 1 microM or much less typically being measured.

Rabbit Pulmonary Artery: NK1 in vitro functional assay (Test D)

The ability of a Compound of the invention to antagonize the action of the agonist Ac-[Arg$^6$, Sar$^9$, Met(O$_2$)$^{11}$] Substance P (6–11), ASMSP, in a pulmonary tissue may be demonstrated as described in Bialecki et al. Kca channel antagonists reduce NO donor-mediated relaxation of vascular and tracheal smooth muscle. Am. J. Physiol. 268: L152–L159, 1995.

Paired tissue segments of pulmonary artery excised from male New Zealand white rabbits are suspended between stainless steel stirrups for analyses of isometric relaxation under standard conditions in physiological salt solution (PSS) containing indomethacin (5 microM; to block cyclooxygenase) and propranolol (1 microM; to block β adrenergic receptors).

Initial tension placed on each tissue is 2 grams, which is maintained throughout the 1.0 hour equilibration period. Tissues are washed with PSS at 15 minute intervals. At the 30 and 45 minute wash the following treatments are added: Thiorphan (1 microM; to block E.C.3.4.24.11), ((3R)-3-[(1S)-1-(3,4-Dichlorophenyl)-3-(4-[(R or S)-2-methylsulfinyl-phenyl]-piperidino)propyl]-2-ethyl-2,3-dihydroisoindol-1-one) (0.03 microM; to block NK$^2$ receptors as described in: "Aharony D., et al. Pharmacological Characterization of ZD7944: A Novel, Potent and orally-Active Non-Peptide Neurokinin-A (NK-2) Receptor Antagonist Eur. Respir. J. 12 (Suppl. 12):20S, 1998"), and the given concentration of the Compound being tested. After equilibration, phenylephrine (3 microM) is added to produce steady-state contraction of the tissue and a dose relaxation curve to ASMSP is constructed. Constructed curves are complete when each tissue fails to relax further for 2 consecutive doses. Papaverine (1 milliM) is then added to obtain a maximum reference relaxation.

For antagonists behaving in a noncompetitive manner, the percent inhibition of relaxation is determined at a given concentration of the antagonist. Percent inhibition is determined when a tested Compound produces a statistically significant reduction of the magnitude of maximum relaxation and is calculated as a percentage of the papaverine reference response For antagonists behaving competitively, potencies are determined by calculating the negative log value of the apparent dissociation constant ($pK_B$) for each concentration tested. Statistical significance is determined when the P value is <0.05 using the Student's t-test for paired comparisons.

In general, the Compounds of the invention having NK1 antagonist activity which were tested demonstrated statistically significant values of the negative log apparent dissociation constant in Test D with a $pK^B$ of 6 or much greater typically being measured.

NK2 in vitro functional assay (Test E)

The ability of a Compound of the invention to antagonize the action of the agonist [$\beta$-ala$^8$] NKA (4–10), BANK, in a pulmonary tissue may be demonstrated as described in Bialecki et al. Kca channel antagonists reduce NO donor-mediated relaxation of vascular and tracheal smooth muscle. Am. J. Physiol. 268: L152–L159, 1995". Left and right pulmonary arteries are excised from male New Zealand white rabbits. The pulmonary arteries are cut into ring segments and the intimal surface rubbed gently to remove the endothelium. Paired tissue segments of pulmonary artery are suspended between stainless steel stirrups for analyses of isometric tension development under standard conditions in physiological salt solution (PSS) containing indomethacin, (5 microM; to inhibit cyclooxygenase).

Initial tension placed on each tissue is 2 grams, which is maintained throughout the 45 minute equilibration period. Tissues are washed with PSS at 15 minute intervals. After the 45 minute equilibration period, $3 \times 10^{-2}$M KCl is applied for 60 minutes to test tissue viability. The tissues are then washed extensively for 30 minutes. The concentration of the Compound being tested is then added for 30 minutes before constructing a cumulative concentration-response curve with BANK. The curve is considered complete when each tissue fails to contract further for 2 consecutively increasing BANK concentrations. $BaCl_2$ ($3 \times 10^{-2}$M) is then added to produce a maximum reference contraction.

Percent inhibition is determined when a tested Compound produces a statistically significant reduction in the magnitude of maximum contraction and is calculated as a percentage of the $BaCl_2$ reference response. For antagonists behaving competitively, potencies are determined by calculating the negative log value of the apparent dissociation constant ($pK_B$) for each concentration tested. Statistical significance is determined when the P value is <0.05 using the Student's t-test for paired comparisons.

In general, the Compounds of the invention having NK2 antagonist activity which were tested demonstrated statistically significant values of the negative log apparent dissociation constant in Test E with a $pK^B$ value of 6 or much greater typically being measured. $NK_1$ and $NK_2$ in vivo functional assay (Test F)

The activity of a compound as an antagonist of NK1 and/or NK2 receptors also may be demonstrated in vivo in laboratory animals as described in: Buckner et al. "Differential Blockade by Tachykinin NK1 and NK2 Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." J. Pharm. Exp. Ther., 1993, Vol 267(3), pp 1168–1175. The assay is carried out as follows.

Compounds are tested in anesthetized guinea pigs pretreated with i.v. indomethacin (10 mg/kg, 20 min.), propranolol (0.5 mg/kg, 15 min.), and thiorphan (10 mg/kg, 10 min).

Antagonists or vehicle are administered i.v. and orally, 30 and 120 minutes prior to increasing concentrations of agonist, respectively. The agonists used in these studies are ASMSP (Ac-[Arg$^6$, Sar$^9$, Met($O_2$)$^{11}$]-SP(6–11)) and BANK ($\beta$-ala-8 NKA4–10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm ($-logED_{50}$). The $ED_{50}$ values, obtained in the presence (P) and absence (A) of antagonist, are used to calculate a Dose Ratio (P/A), an expression of potency. Data are expressed as mean$\pm$SEM and statistical differences were determined using ANOVA/Tukey-Kramer and Student's t-test, with $p<0.05$ considered statistically significant.

Compounds of the present invention exhibit marked activity in the foregoing tests and are considered useful for the treatment of those diseases in which the NK1 and/or NK2 receptor is implicated, for example, in the treatment of asthma and related conditions.

Results of testing of representative compounds of the present invention by the above methods are presented in the Table I.

TABLE I

| Example | Test D NK1pKb | Test E NK2pKb | Test F NK1 P/A | Test F NK2 P/A |
|---|---|---|---|---|
| 1 | 8.99 | 8.26 | 32.5 (2 hr) | 21.4 (2 hr) |
| 2 | 8.1 | 8.7 | 25.0 (2 hr) | 83.0 (2 hr) |
| 36 | 8.13 | 7.86 | 45.0 (1 hr) | 20.6 (1 hr) |

Clinical Studies

Because of the range of effects attributable to the actions of SP, NKA and NKB, compounds which are capable of blocking their actions may also be useful as tools for further evaluating the biological actions of other neurotransmitters in the tachykinin family. As a result, another feature of the invention is provided by the use of a compound of Formula I or a salt or precursor thereof as a pharmacological standard for the development and standardization of new disease models or assays for use in developing new therapeutic agents for treating diseases in which SP or NKA are implicated or for assays for their diagnosis.

EXAMPLES

The invention will now be illustrated by the following non-limiting examples, in which, where applicable and unless stated otherwise:

(i) temperatures are given in degrees Celsius (° C.); unless otherwise stated, operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(viii) solvent ratios are given in volume:volume (v/v) terms; and (ix) Mass spectra (MS) were run using an automated system with atmospheric pressure chemical ionization (APCI). Where indicated, the following alternative methods of ionization were used; a) desorption chemical ionization (CI) using methane reagent gas and a direct exposure probe; or b) electron impact (EI). Masses corresponding to the major isotopic component or the lowest mass for compounds with multiple masses with nearly equivalent abundance (isotope splitting) are reported.

Terms and abbreviations: Solvent mixture compositions are given as volume percentages or volume ratios. In cases where the NMR spectra are complex, only diagnostic signals are reported. atm; atmospheric pressure, Boc; t-butoxycarbonyl, Cbz; benzyloxyarbonyl, DCM; methylene chloride, DMF; N;N-dimethyl formamide, DMSO; dimethyl sulfoxide, $Et_2O$; diethyl ether, EtOAc; ethyl actate, FAB; fast atom bombardment, h; hour(s), HPLC: high pressure liquid chromatography, min; minutes, NMR; nuclear magnetic resonance, psi; pounds per square inch, TFA; trifluoroacetic acid, THF; tetrahydrofuran.

Examples of the compounds of the formula (I) are prepared by either reductive animation [process a); reacting compounds of the formula (III) and (IV)] or acylation [process b); reacting compounds of the formulae (V) and (VI).

Standard reductive amination refers to the typical procedure in which a solution of an amine (1–1.2 equivalents), an aldehyde (1–1.2 equivalents) and acetic acid (2 equivalents) are stirred in methanol for 5 to 60 minutes before adding $NaBH_3CN$ (1.7 equivalents). After 1–16 h the reaction is optionally concentrated, dissolved in DCM, and washed with saturated sodium bicarbonate and then purified by chromatography.

Standard acylation refers to the typical procedure in which an acid chloride (1–1.2 equivalents) is added to a stirred solution of an amine (1–1.2 equivalents) and triethylamine (2 equivalents) in DCM. After 1–16 h the reaction is optionally concentrated, dissolved in DCM, and washed with saturated sodium bicarbonate and then purified by chromatography.

Where noted that a final compound was converted to the citrate salt, the free base was combined with citric acid (1.0 equivalents) in methanol, concentrated under reduced pressure and dried under vacuum (25–70° C.). When indicated that a compound was isolated by filtration from $Et_2O$, the citrate salt of the compound was stirred in $Et_2O$ for 12–18 h, removed by filtration, washed with $Et_2O$, and dried under vacuum at 25–70° C. In a few cases the free base was dissolved in DCM or acetonitrile, combined with citric acid in methanol, and the resultant mixture concentrated and, optionally, washed with $Et_2O$ Where noted that a final compound was converted to the hydrochloride salt, a solution of HCl in $Et_2O$ was added with stirring to a solution of the purified free base in DCM or methanol. The resulting precipitate was collected by filtration and dried under vacuum.

Example 1

N-[(S)-2-(3,4-Dichlorophenyl)-4-[4-[(S)-2-methylsulfinylphenyl]-1-piperidinyl]butyl]-N-methyl-3-cyano-1-naphthamide A stirred solution containing 3-cyano-1-naphthoic acid (0.1 g, 0.5 mmol), N,N-diisopropylethylamine (0.16 g, 1.26 mmol), and dry DCM (2.5 mL) was treated with a solution of tetramethylfluoroformamidinium hexafluorophosphate (TFFH) (0.16 g, 0.60 mmol) in dry DCM (1.0 mL). After 10 min, a solution containing N-[(S)-2-(3,4-dichlorophenyl)-4-[4-[(S)-2-methylsulfinylphenyl]-1-piperidinyl]butyl]-N-methylamine (0.22 g, 0.5 mmol) and dry DCM (0.6 mL) was added, and the solution stirred for 60 h, then diluted with DCM and 1M aqueous acetic acid. After mixing, the layers were allowed to separate, the organic layer was removed, and the aqueous layer was extracted with additional DCM (2×). The organic extracts were combined, washed (saturated $NaHCO_3$), dried ($Na_2SO_4$), filtered, and the DCM evaporated in vacuo. The residue was purified by chromatography (0–10% $CH_3OH$ in DCM) to give the title compound (0.25 g) as a white, foamy residue. MS: m/z 632 (M+H). The product was converted to the citrate salt and isolated by filtration from $Et_2O$ to afford the N-[(S)-2-(3,4-dichlorophenyl)-4-[4-[(S)-2-methylsulfinylphenyl]-1-piperidinyl]butyl]-N-methyl-3-cyano-1-naphthamide citrate hydrate (1:1:0.75) (290 mg) as a white solid. MS: m/z 632 (M+H). Analysis for $C_{35}H_{35}Cl_2N_3O_2S$ $C_6H_8O_7$.0.75 $H_2O$: calculated: C, 58.74; H, 5.35; N, 5.01. found: C, 58.74; H, 5.24; N, 5.02. The title compound could also be converted, in similar maimer, to the citrate hydrate (1.0:1.0:1.0).

Alternately, the above titled compound was prepared by reacting the amine with 3-cyano-1-naphthoyl chloride. The required acid chloride was prepared as follows: a stirred mixture containing 3-cyano-1-naphthoic acid (0.18 g, 0.93 mmol) and dry DCM (7.5 mL) was treated with oxalyl chloride (0.14 g, 1.15 mmol) and dry DMF (10 μL) at ambient temperature. After 4 h, the solvent was evaporated in vacuo. The off-white solid residue was dissolved in dry DCM and used without further purification. Using standard acylation conditions 3-cyano-1-naphthoyl chloride was reacted with N-[(S)-2-(3,4-dichlorophenyl)-4-[4-[(S)-2-methylsulfinylphenyl]-1-piperidinyl]butyl]-N-methylamine. The product was converted to the citrate salt and isolated by filtration from $Et_2O$ to afford the citrate salt (740 mg) as a white solid. MS: m/z 632 (M+H). Analysis for $C_{34}H_{35}Cl_2N_3O_4S.C_6H_8O_7$.0.5 $H_2O$ .0.40 $C_4H_{10}O_4(Et_2O)$: calculated: C, 59.26; H, 5.60; N, 4.87. found: C, 59.14; H, 5.52; N, 4.78. In a similar manner, the title compound could also be converted to the citrate hydrate (1.0:1.0:0.5).

The requisite N-[(S2-(3,4-dichlorophenyl)-4-[4-[(S)-2-methylsulfinylphenyl]-1-piperidinyl]butyl]-N-methylamine was prepared as follows.

(a) N-[(S)-2-(3,4-Dichlorophenyl)-4-[4-[(S)-2-methylsulfinylphenyl]-1-piperidinyl]butyl]-N-methyl-N-Boc-amine.

(S)-N-[2-(3,4-Dichlorophenyl)-4-oxobutyl]-N-methyl-N-Boc-amine (Miller, S C; WO 9505377) (51.7 g, 149.3 mmol), 4-[(S)-2-methylsulfinylphenyl]-piperidine (Shenvi, A B; Jacobs, R T; Miller, S C; Ohnmacht, C J, Jr.; Veale, C A., WO 9516682) (36.7 g, 164.3 mmol), and glacial acetic acid (9.9 g, 165.0 mmol) were dissolved in methanol (1000 mL), and the solution stirred for 15 min. Sodium cyanoborohydride (10.4 g, 165.5 mmol) was added in portions as a solid over 30 min. The mixture was stirred for 20 h, then treated with saturated sodium bicarbonate (500 mL). Methanol was removed in vacuo, and the aqueous residue was extracted with DCM (4×400 mL). The organic layer was washed with brine (300 mL), dried (MgSO$_4$), filtered, and concentrated in vacuo. The residue was purified by chromatography (0–6% methanol in DCM) to provide a white foam (77.2 g, 93%). MS: 553 (M+H). $^1$H-NMR (CDCl$_3$) δ 1.40 (s, 9H, t-C$_4$H$_9$); 1.61–2.04 (m, 9H, CH); 2.14–2.23 (m, 2H, CH); 2.62–2.79 (m 6H, NCH$_3$, SOCH3); 2.91–3.00 (m, 3H, CH); 3.27–3.54 (m,2H, CH); 7.00–7.09 (m, 1H, aromatic); 7.21–7.53 (m, 5H, aromatic); 7.95–8.04 (m, 1H, aromatic).
(b) N-[(S)-2-(3,4-Dichlorophenyl)-4-[4-[(S)-2-methylsulfinylphenyl]-1-piperidinyl]butyl]-N-methylamine.

N-[(S)-2-(3,4-Dichlorophenyl)-4-[4-[(S)-2-methylsulfinylphenyl]-1-piperidinyl]butyl]-N-methylamine-N-Boc-amine (77.0 g, 139.0 mmol) was dissolved in DCM (1200 mL). To the stirred solution was added trifluoroacetic acid (160.0 g, 1.40 mol) dropwise over 15 min. The mixture was stirred for 4 h, then additional trifluoroacetic acid (80.0 g, 0.70 mol) was added, and the mixture stirred an additional 1.5 h. The mixture was washed with aqueous sodium carbonate (225 g, 1500 mL water), water (2×500 mL), then dried (MgSO$_4$). Filtration and concentration left the crude product as a yellow gum. Purification by chromatography (0–20% methanol/DCM) provided a light yellow foam (61.8 g, 98%). MS: 453 (M+H). $^1$H-NMR (CDCl$_3$) δ 1.64–2.09 (m, 7H, CH); 2.27–2.35 (m, 2H, CH); 2.46 (s, 3H, NCH$_3$); 2.68 (s, 3H, SOCH$_3$); 2.74–3.05 (m, 7H, CH); 3.39–3.78 (bs, 1H, NH); 7.07–7.10 (m, 1H, aromatic); 7.23–7.50 (m, 5H, aromatic); 7.95–7.99 (m, 1H, aromatic).

The requisite 3-cyano-1-naphthoic acid (Dewar, J S and Grisdale, P J; J. Amer. Chem. Soc., 84, 3541–3546 (1962) was prepared as follows.

(c) 3-Cyano-1-naphthoic acid.

Using the procedure of Rule, H G and Thompson, S B; J. Chem. Soc. 1764–1767 (1937), 1,8-naphthalic anhydride was brominated and converted to 3-bromo-1-naphthoic acid This was esterified to methyl 3-bromo-1-naphthoate according to the following procedure. 3-Bromo-1-naphthoic acid (103.0 g, 410 mmol) was dissolved in DCM (1250 mL) and the solution cooled to 0° C. Oxalyl chloride (67.5 g, 532 mmol) was added in one portion followed by a catalytic amount of DMF (1.5 mL), and the resulting solution allowed to warm to ambient temperature and stir for 4 hours. The mixture was evaporated in vacuo, and the residue concentrated a second time from toluene. The resultant acid chloride was dissolved in methanol (1250 ml) and stirred at ambient temperature for 18 h. The mixture was evaporated in vacuo, and the residue purified by chromatography (eluent: DCM:hexanes 1:3) to provide methyl 3-bromo-1-naphthoate as a white solid (106.9 g, 98%). $^1$H-NMR (CDCl$_3$) δ 4.01 (s, 3H, CO$_2$CH$_3$); 7.50–7.69 (m, 2H, aromatic); 7.78–7.87 (d, 1H, aromatic); 8.18 (s, 1H, aromatic); 8.25 (s, 1H, aromatic); 8.80–8.94 (d, 1H, aromatic). Using the procedure of Dewar, J S and Grisdale, P J; J. Amer. Chem. Soc., 84, 3541–3546 (1962), methyl-3-bromo-1-naphthoate was converted to methyl 3-cyano-1-naphthoate and then saponified (LiOH) to the title compound.

Example 1A

The title compound of Example 1 may also be prepared in the following manner: a) Anhydrous dimethylsulphoxide (1.69 g) in dichloromethane (5 ml) was added to oxalyl chloride (1.37 g) in dichloromethane (12 ml) at −60° C. to −50° C. N-[(S)-2-(3,4-dichlorophenyl)-4-oxo-butyl]-N-methyl-3-cyano-1-naphthamide (2.31 g) in dichloromethane (14 ml) was added to this solution, with stirring. After 30 minutes triethylamine (2.19 g) was added and the reaction was stirred at a low temperature for a further hour before being allowed to warm to ambient temperature. The reaction was quenched with HCl, and the organic phase was washed with HCl, saturated NaHCO$_3$ and brine. The organic phase was then added, dropwise, to a slurry of 4-[(S)-2-methylsulfinylphenyl]piperidine (1.33 g) in dichloromethane at ambient temperature. After 15 minutes borane-pyridine complex (0.25 g) was added. The reaction was stirred overnight, quenched with water and the dichloromethane phase was washed with brine and concentrated under reduced pressure to give a pale brown foam.

This was treated with an equivalent of fumaric acid in hot ethanol. The solution was stirred at 70° C. and allowed to cool slowly to ambient temperature to form crystals of the hydrogen fumarate of the title product (recrystallised from ethanol/water).

Example 2

N-[(S)-2-(3,4-Dichlorophenyl)-4-[4-{4-methoxy-(S)-2-methylsulfinylphenyl}-1-piperidinyl]butyl]-N-methyl-3-cyano-1-naphthamide Citrate In the same manner as Example 1A, anhydrous dimethylsulphoxide in dichloromethane was added to oxalyl chloride in dichloromethane at −60° C. to −50° C. N-[(S)-2-(3,4-dichlorophenyl)-4-oxo-butyl]-N-methyl-3-cyano-1-naphthamide in dichloromethane was added to this solution, with stirring. After 30 minutes, triethylamine was added and the reaction was stirred at a low temperature for a further 3.5 hours before being allowed to warm to ambient temperature. The reaction was quenched with HCl, and the organic phase was washed with HCl, saturated NaHCO$_3$ and brine. The organic phase was then added to a solution of 4-[4-methoxy-(S)-2-methylsulfinylphenyl]piperidine in methanol at 20° C. After 15 minutes borane-pyridine complex was added over 45 minutes. The reaction was stirred for 20 hours, quenched with HCl and the dichloromethane phase was washed with HCl, NaHCO$_3$ and brine and concentrated under reduced pressure to give a yellow foam.

This was treated with an equivalent of fumaric acid in hot ethanol. The solution was stirred at 70° C. for 1 hour, heated to reflux and water added dropwise. After a further hour at reflux the mixture was allowed to cool slowly to ambient temperature to form crystals of the hydrogen fumarate of the title product (recrystallised from ethanol/water).

In another procedure the title compound was prepared by reductive amination in methanol with acetic acid and sodium cyanoborohydride and was converted to the citrate salt as follows.

To a stirred solution of N-[(S)-2-(3,4-dichlorophenyl)-4-oxo-butyl]-N-methyl-3-cyano-1-naphthamide (0.154 g) and 4-(4-methoxy-2-(S)-methylsulfinylphenyl)piperidine (0.097 g) in 7 ml MeOH was added 35 ml of acetic acid. Mixture was stirred for 30 minutes and 0.045 g of sodium cyanoborohydride was added (as a solution in 2 ml MeOH). The reaction mixture was stirred at room temperature under N$_2$ atmosphere overnight (18 h). At the end of this period the reaction was quenched with 10 ml sat'd NaHCO$_3$, evaporated, dissolved in 10 ml H$_2$O , and extracted with CH$_2$Cl$_2$. The organic layers were combined, dried over Na$_2$SO$_4$, filtered, and concentrated under reduced pressure to give a foam which was purified by chromatography on silica (19:1, $CH_2Cl_2$:MeOH w/0.5% $NH_{3(aq)}$). Purified product was dissolved in 3 ml $CH_2Cl_2$ and treated with 50 ml $Et_2O$ containing 3 ml $HCl_{(g)}$ sat'd $Et_2O$. After stirring for 10 minutes the precipitate was filtered under a steady stream of $N_2$ to give 0.210 g of white powder;

mp 165–170° C.; $^1H$ NMR (DMSO-$d_6$) δ 1.60–2.40 (m,5), 2.55–2.65 (m,3), 2.71 (s,3), 2.71 (s,3), 2.80–3.30 (m,5), 3.36 (s,3), 3.45–3.70 (m,3), 3.82 (s,3), 6.85–7.09 (m,10), 8.10 (8.10 (m,1), 8.63 (m,1), 10.64 (m,1); MS: m/z 662 (M+H).

The requisite 4-(4-methoxy-2-(S)-methylsulfinylphenyl)-piperidine was prepared as follows.

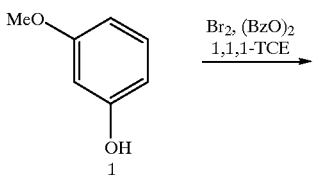

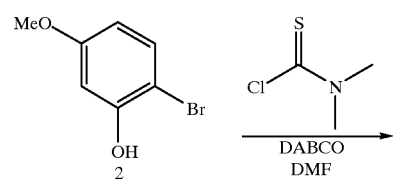

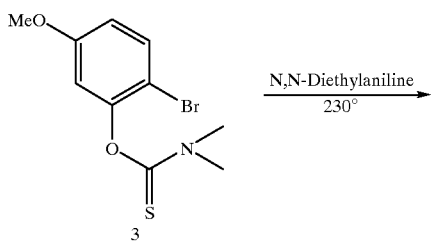

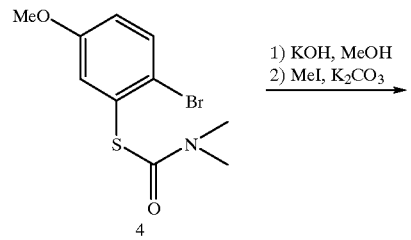

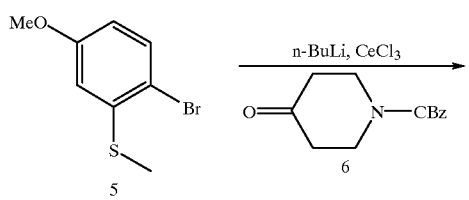

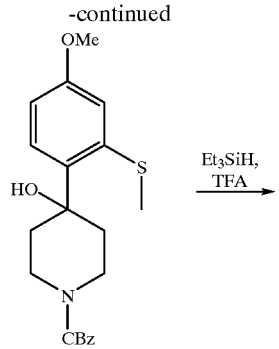

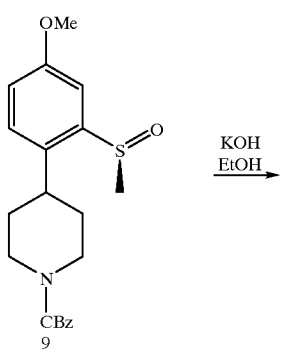

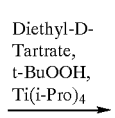

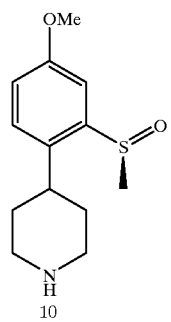

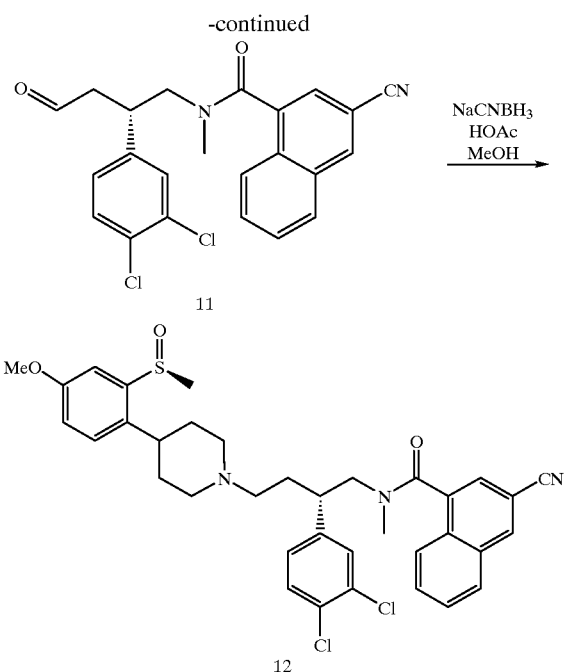

(a) 2-Bromo-5-methoxyphenol (2).

To a solution of 3-methoxyphenol (129.03 g) and benzoyl peroxide (1.00 g) in 500 mL 1,1,1-trichloroethane (TCE) was slowly added a solution of bromine (167.90 g in 150 mL in 1,1,1-TCE) over 1 h. During the addition the reaction flask was irradiated with a GE sunlamp (275 watt, 120 volt) which caused a gentle reflux to occur. The HBr released was trapped in a beaker containing a solution of 126.02 g NaHCO$_3$ and 800 mL H$_2$O. When the addition of bromine was complete the reaction mixture was purged with N$_2$ for 20 minutes. The reaction mixture was extracted with saturated NaHCO$_3$ until the pH of the aqueous extract was neutral.

The organic layer was dried over anhydrous Na$_2$SO$_4$, filtered, and concentrated under reduced pressure to give a reddish oil. The crude product was purified by vacuum distillation (150° C., 150 millitor) to give 161.78 g of a viscous liquid; $^1$H NMR (CDCl$_3$) δ 3.77 (s, 3), 5.57 (s, 1), 6.42 (m, 1), 6.60 (d, 1), 7.30 (d, 1).

(b) 2-Bromo-5-methoxy-(N,N-dimethylthiocarbamoyloxy)phenol (3).

To a stirred solution of 2-bromo-5-methoxyphenol (161.78 g) and 1,4-diazabicyclo-[2.2.2]octane (180.03 g) in 1 L DMF was slowly added 200 g of dimethylthiocarbamoyl chloride in four separate 50 g portions over 30 min. When the addition was complete the mixture was stirred overnight (18 h) under N$_2$ atmosphere. At the end of this period the mixture was poured into 4 L distilled H$_2$O with rapid stirring. The precipitated product was collected by filtration and washed with H$_2$O. The crude product was air-dried for 4 h and crystallized from methanol to give white crystals (139.19 g); $^1$H NMR (300 MHz, CDCl$_3$) δ 3.38 (s, 3), 3.47 (s, 3), 3.79 (s,3), 6.71 (m, 2), 7.45 (m, 1); MS: m/z 290 (M+H).

(c) 4-Bromo-3-(N,N-dimethylcarbamoylthio)methoxybenzene (4).

A solution of 2-bromo-5-methoxy-(N,N-dimethylthiocarbamoyloxy)phenol (139.19 g) and N,N-diethyaniline (350 mL) was degassed (4 cycles) and then heated under reflux under N$_2$ for 3.5 h. The resulting brown solution was concentrated (short path distillation) to approximately 100 mL and the residue was poured into 500 mL of ice cold 6N HCl with rapid stirring. The mixture was cooled to room temperature, 100 mL Et$_2$O was added, and a heavy precipitate formed which was collected by filtration. This tan precipitate (crude product) was briefly air-dried and set aside. The filtrate was extracted with Et$_2$O. Et$_2$O extracts were combined, dried over MgSO$_4$, filtered, and concentrated under reduced pressure to give a brownish solid (additional crude product). The crude product was purified by crystallization from methanol to give off-white crystals (82.04 g). 1H NMR (300 MHz, CDCl$_3$) δ 3.05 (br s, 3), 3.12 (br s, 3), 3.79 (s, 3), 6.82 (dd, 1), 7.19 (d, 1), 7.55 (d, 1); MS: 290 (m+H).

(d) 4-Bromo-3-(methylthio)-methoxybenzene (5).

To a stirred solution of KOH (120.01 g) in 500 mL methanol was added 82.04 g of 4-bromo-3-(N,N-dimethylcarbamoylthio)methoxybenzene. The mixture was heated under reflux under N$_2$ atmosphere for 2 h, then cooled to 0° C. and neutralized with 400 mL of 6N HCl. The mixture was cooled to 0° C. and extracted with DCM. The organic extracts were combined, dried over Na$_2$SO$_4$, filtered, and concentrated under reduced pressure to give a light brown liquid. This liquid was dissolved in 600 mL anhydrous DMF and treated with 80.90 g anhydrous K$_2$CO$_3$. The resulting mixture was stirred for 20 min and then 68.40 g of methyl iodide was slowly added over 15 min. The resulting mixture was stirred at room temperature under N$_2$ atmosphere overnight (18 h). At the end of this period the reaction mixture was poured into 2.8 L distilled H$_2$O and extracted with Et$_2$O. The organic layers were combined, dried over MgSO$_4$, filtered, and concentrated under reduced pressure to give a pale yellow liquid (65.03 g). $^1$H NMR (CDCl$_3$) δ 2.45 (s, 3), 3.80 (s, 3), 6.55 (dd, 1), 6.66 (d, 1), 7.39 (d, 1).

(e) 4-Hydroxy-4-(4-methoxy-2-methylthiophenyl)-N-Cbz-piperidine (7).

Cerium (III) chloride heptahydrate (181.38 g) was heated under high vacuum at 100° C. for 2 days then at 140° C. for two days. This material was transferred to a dry flask equipped with mechanical stirrer, suspended in 700 mL anhydrous THF, and stirred while cooling to −78° C. A solution of 4-bromo-2-(methylthio)methoxybenzene in 500 mL anhydrous THF was cooled to −78° C. and treated dropwise with n-butyllithium (111.5 mL of a 2.5 M solution in hexane) over 1 hour. The temperature of the reaction flask was kept below −70° C. during the addition. This mixture was stirred at −78° C. for 1.5 hours and transferred via wide bore insulated cannula into the flask containing the stirred suspension of CeCl$_3$ at −78° C. The resulting peach colored suspension was stirred for 1.5 h at −78° C. and then a solution of 1-benzyloxycarbonyl-4-piperidone (65.10 g in 200 mL anhydrous THF) was added via cannula over 30 minutes. When the addition was complete the reaction mixture was warmed to room temperature and stirred overnight (18 h). At the end of this period the reaction mixture was quenched with 500 mL saturated NH$_4$Cl and stirred for 30 minutes. The organic layer was decanted, concentrated under reduced pressure, and set aside. The remaining grayish suspension was stirred with 1 L DCM and filtered through Celite. The Celite filter cake was washed with DCM. All organic extracts were combined, dried over Na$_2$SO$_4$, filtered, and concentrated under reduced pressure to give a viscous oil which was purified by chromatography on silica (1:1, EtOAc:hexane) to give 85.00 g of an oil. $^1$H NMR (CDCl$_3$) δ 1.99 (m,2), 2.12 (m, 2), 2.52 (s, 3), 3.39 (m, 2), 3.81 (s, 3), 4.10 (m, 3), 5.15 (s, 2), 6.71 (dd, 1), 6.95 (d, 1), 7.24 (d, 1), 7.37 (m, 5); MS: 387 (M+H).

(f) 4-(4-Methoxy-2-methylthiophenyl)-N-Cbz-piperidine (8).

To an ice-cooled, rapidly stirred slurry of 4-hydroxy-4-(4-methoxy-2-(methylthio)-phenyl)-N-Cbz-piperidine (50.09 g) in triethylsilane (29.12 g) was slowly added trifluoroacetic acid (29.60 g). When addition was complete the mixture was warmed to room temperature and stirred overnight (18 h). At the end of this period the mixture was poured into 300 mL saturated $NaHCO_3$ and extracted with DCM. Extracts were combined, dried over $Na_2SO_4$, filtered, and concentrated under reduced pressure to give an oil. The product was purified by chromatography on silica (40:1 to 20:1 gradient, DCM:EtOAc) to give 42.50 g of an oil. $^1$H NMR ($CDCl_3$) δ 1.57 (m,2), 1.83 (d,2), 2.46 (s,3), 2.91 (m,2), 3.06 (tt,1), 3.80 (s,3), 4.33 (m,2), 5.14 (s,2), 6.68 (dd,1), 6.76 (d,1), 7.04 (d,1), 7.36 (m,5); MS: m/z 394 (m+Na).

(g) 4-(4-Methoxy-2-(S)-methylsulfinylphenyl)-N-Cbz-piperidine (9).

To a 500 mL flask was added 11.56 g diethyl-D-tartrate, 140 mL anhydrous DCM, 7.96 g titanium (IV) isoproproxide, and 0.50 g $H_2O$. The pale yellow solution was stirred for 30 minutes and then treated with 10.78 g of 4-(4-methoxy-2-methylthiophenyl)-N-Cbz-piperidine dissolved in 40 mL DCM. The reaction mixture was then immersed in a water/glycol bath pre-chilled to −30° C. After stirring for 30 min (bath temperature −36° C.) 5.6 mL of a 6M solution of tert-butylhydroperoxide in nonane was slowly added to the reaction mixture and stirred for 6 days under $N_2$ atmosphere (bath temperature −38° C.). At the end of this period the reaction was quenched with 50 mL $H_2O$ and stirred vigorously for 1 hour while warming to room temperature. The mixture was then treated with 100 mL of 2.5 M NaOH and stirred for an additional 20 min, filtered through Celite and the layers were separated.

The filter cake was washed with DCM twice and each portion was used to extract the aqueous layer. The organic extracts were combined, dried over $Na_2SO_4$, filtered, and concentrated under reduced pressure. This gave a light yellow oil which was purified by chromatography on silica (4:1, EtOAc:DCM). $^1$H NMR ($CDCl_3$) δ 1.62 (m, 2), 1.79 (m, 2), 2.86 (m, 3), 2.87 (s, 3), 4.34 (m, 2), 5.16 (s, 2), 7.00 (dd, 1), 7.18 (d, 1), 7.36 (m, 5), 7.52 (d, 1); MS: m/z 410 (m+Na).

(h) 4-(4-Methoxy-2-(S)-methylsulfinylphenyl)piperidine (10).

To a solution of KOH (1.50 g) in 20 mL of 1:1 EtOH:$H_2O$ was added 1.23 g of 4-(4-methoxy-2-(S)-methylsulfinylphenyl)-N-Cbz-piperidine. The resulting mixture was heated reflux under $N_2$ atmosphere for 18 h, evaporated, dissolved in 10 mL H2O, and extracted with $CHCl_3$. The organic extracts were combined, dried over $Na_2SO_4$, filtered, and concentrated under reduced pressure. The resulting residue was purified by chromatography on silica (19:1, DCM:MeOH with 0.5% aqueous $NH_4OH$) to give 0.38 g of white solid. $^1$H NMR ($CDCl_3$) δ 1.69 (m,2), 1.82 (m,2), 2.38 (m,1), 2.70 (s,3), 2.75 (m,2), 3.22 (m,2), 3.88 (s,3), 7.01 (dd,1), 7.28 (d,1), 7.51 (d,1); MS: 254 (M+H).

The intermediate N-[2-(S)-(3,4-dichlorophenyl)-4-oxobutyl]-N-methyl-3-cyano-1-naphthamide was prepared as follows.

(i) 3-Cyano-1-naphthoyl chloride.

3-Cyano-1-naphthoic acid (Example 1) (15.9 g, 80.6 mmol) was suspended in DCM (450 mL). To the stirred suspension was added at ambient temperature oxalyl chloride (12.8 g, 100 mmol) in one portion followed by a catalytic amount (5 drops) of DMF. The mixture was stirred for 5 hours giving a clear solution. The mixture was concentrated in vacuo, and the residue concentrated twice from toluene to provide the crude acid chloride as a light yellow solid (17.4 g, quantitative). $^1$H-NMR (300 MHz, $d_6$ acetone) δ 7.86–7.91 (t, 1H, aromatic); 7.98–8.04 (t, 1H, aromatic); 8.28–8.32 (d, 1H, aromatic); 8.66–8.72 (d, 1H, aromatic); 8.80 (s, 1H, aromatic); 8.93 (s, 1H, aromatic).

(j) N-[(S)-2-(3,4-Dichlorophenyl)-4-hydroxybutyl]-N-methyl-3-cyano-1-naphthamide.

(S)-2-(3,4-Dichlorophenyl)-4-hydroxybutylamine (Miller, S C; WO 9410146) (20.8 g, 83.8 mmol) was dissolved in DCM (700 mL). To the stirred solution was added 10% aqueous sodium bicarbonate (300 mL), and the mixture cooled to 0° C. A solution of 3-cyano-1-naphthoyl chloride (17.4 g, 80.6 mmol), dissolved in DCM (300 mL) was added dropwise over 30 minutes. The mixture was then allowed to warm to ambient temperature and stir for 20 h. The layers were separated, and the aqueous phase washed with DCM (300 mL). The combined organic layers were dried ($Na_2SO_4$), filtered, and evaporated in vacuo to give a white foam. Purification by chromatography (silica gel; 0–25% acetonitrile in DCM) provided the desired product as a white foam (27.0 g, 78%). $^1$H-NMR (DMSO-$d_6$) δ 1.46–1.60 (m, 1H, CH); 1.77–1.91 (m, 3H, CH); 4.38–4.41 (t, 1H, CH); 4.54–4.57 (t, 2H, CH); 6.43 (broad, 1H, OH); 6.84–7.26 (m, 2H, aromatic); 7.44–7.54 (m, 3H, aromatic); 7.57–7.80 (m, 7H, aromatic); 8.04–8.33 (m, 2H, aromatic); 8.61 (s, 1H, aromatic).

In an alternative N-[(S)-2-(3,4-dichlorophenyl)-4-hydroxybutyl]-N-methyl-3-cyano-1-naphthamide may be prepared as follows: To a stirred slurry of 3-cyano-1-naphthoic acid (4.53 g) in acetonitrile (36 ml) at ambient temperature, was added 1-hydroxybenzotriazole (0.31 g) and subsequently (S)-2-(3,4-dichlorophenyl)-4-hydroxybutylamine (8.33 g) in acetonitrile. The mixture was stirred for 15 minutes before 1-(3-dimethylaminopropyl)-3-ethylcarbodiimide hydrochloride (5.26 g) in 1:1 acetonitrile:water was added dropwise over 1 hour. The mixture was stirred at ambient temperature for 18 hours, and HCl (68 ml) and methyl t-butyl ether (68 ml) were added consecutively. The organic phase was treated with NaOH, stirred at 45° C. for 3 hours, cooled, washed and concentrated under reduced pressure to give a foam. This foam was redissolved in acetonitrile, heated to 80° C., water was added and then cooled to give the desired product as a white solid.

(k) N-[(S)-2-(3,4-Dichlorophenyl)-4-oxobutyl]-N-methyl-3-cyano-1-naphthamide.

A solution of oxalyl chloride (15.9 g, 125.4 mmol) dissolved in DCM (350 mL) was cooled to −78° C. DMSO (19.6 g, 251 mmol) was added dropwise over 10 minutes while maintaining the temperature of the reaction mixture below −70° C. The mixture was stirred for 30 min at −78° C. A solution of N-[(S)-2-(3 ,4-dichlorophenyl)-4-hydroxybutyl]-N-methyl-3-cyano-1-naphthamide (26.8 g, 62.7 mmol) was dissolved in DCM (350 mL) and added dropwise over 30 min while maintaining the temperature of the mixture below −70° C. The mixture was allowed to stir for one h at −78° C., then warmed to −50° C. and stirred for another 30 minutes. The mixture was cooled to −78° C. and a solution of triethylamine (25.4 or 251 mmol) dissolved in DCM (70 mL) was added dropwise over 10 min. The mixture was then allowed to warm gradually to ambient temperature and stir for 20 hours. The mixture was then washed with 0.5N hydrochloric acid (2×250 mL), water (250 mL), and saturated sodium bicarbonate (250 mL). The organic layer was dried ($Na_2SO_4$), filtered, and concentrated in vacuo. The residue was purified by chromatography (silica gel; 0–20% Et$_2$O in DCM) to provide the desired product as a light yellow foam (26.0 g, 97%). MS: 425 (M+H). $^1$H-NMR (DMSO-d$_6$) δ 2.63 (bs, 3H, NCH$_3$); 2.99–3.93 (m, 5H, CH); 6.91–7.15 (m, 1H, aromatic); 7.33–7.81 (m, 6H, aromatic); 8.62 (s, 1H, aromatic); 9.45 and 9.73 (singlets, 1H total, CHO).

Example 3

N-[2-(4-Chlorophenyl)-4-[4-[(S)-2-methylsulfinylphenyl]-1-piperidinyl]butyl]-N-methyl-3-nitro-1-naphthamide Citrate Using standard reductive amination conditions 4-[(S)-2-methylsulfinylphenyl]-piperidine (Shenvi, A B; Jacobs, R T; Miller, S C; Ohnmacht, C J, Jr.; Veale, C A. WO 9516682) was reacted with N-[2-(4-chlorophenyl)-4-oxobutyl]-N-methyl-3-nitro-1-naphthamide and converted to the citrate salt. MS m/z 618 (M+H); analysis for C$_{34}$H$_{36}$ClN$_3$O$_4$S.1.08 C$_6$H$_8$O$_7$.1.0 H$_2$O: calculated: C, 57.63; H, 5.57; N, 4.98; found: C, 57.67; H, 5.47; N. 4.78.

The required aldehyde was prepared as follows.

(a) 2-[[3-Cyano-3-(4-chlorophenyl)]propyloxy]-2H-tetrahydropyran.

To a stirred cooled (0° C.) mixture of 60% sodium hydride (3.73 g, 93.3 mmol) in THF (80 mL) was added dropwise a solution of 4-chlorobenzylcyanide (13.0 g, 85.8 mmol) in THF (20 mL) and the solution was stirred at room temperature for 3 h. The solution was cooled (ice bath) and 2-(2-bromoethoxy)-2H-tetrahydropyran (15 g, 71.7 mmol) was added dropwise and the solution stirred at room temperature overnight. Saturated ammonium chloride was added and the mixture was extracted with EtOAc. The combined organic extracts were dried (MgSO$_4$). filtered, and concentrated in vacuo. Purification by chromatography (30%. 50%, 60% and 80% DCM in hexane) provided the title compound (19.7 g, 98% yield) as a yellow oil. $^1$H-NMR (CDCl$_3$): δ 1.53–1.64 (m, 4H, CH) 1.71–1.82 (m, 2H, CH) 2.09–2.16 (m, 2H, CH) 3.52–3.57 (m, 2H, CH) 3.80–3.93 (m, 2H, CH) 4.05–4.10 (t, 1H, CH) 4.55–4.60 (m, 1H, CH) 7.28–7.41 (m, 4H, ArH). MS m/z 284 (M+H).

(b) 2-[[4-Amino-3-(4-chlorophenyl)]butyloxy]-2H-tetrahydropyran.

To a mixture of Raney Nickel (8.0 g) in ethanol (20 mL) was added a solution of 2-[[3-cyano-3-(4-chlorophenyl)] propyloxy]-2H-tetrahydropyran.(25 g, 89.4 mmol) in ethanol (160 mL). Nitrogen was bubbled through the mixture for 5 min and ammonium hydroxide (30%, 120 mL) was added. The mixture was set on Parr apparatus under hydrogen (50 psi) for 5 days and filtered through Celite. The filtrate was concentrated, DCM and water were added and the layers separated. The organic layer was dried (MgSO$_4$), filtered, and concentrated in vacuo. Purification by chromatography (1–5% methanol in DCM) provided the title compound (13.0 g, 51%) as a light yellow oil. $^1$H-NMR (CDCl$_3$): δ 1.51 (m, 4H, CH) 1.65 (m, 1H, CH) 1.74–1.82 (m, 2H, CH) 1.95–2.01 (m, 1H, CH) 2.76–2.97 (m, 3H, CH) 3.16–3.18 (m, 1H, CH) 3.41–3.44 (m, 1H, CH) 3.57–3.80 (m, 2H, CH) 4.41–4.49 (dd. 1H, CH) 7.11–7.16 (m, 2H, ArH) 7.28–7.30 (m, 2H, ArH). MS 284 (M+H).

(c) 4-Amino-3-(4-chlorophenyl)-1-butanol.

To a stirred solution of 2-[[4-amino-3-(4-chlorophenyl)] butyloxy]-2H-tetrahydropyran (13.0 g, 45.7 mmol) in methanol (90 mL) was added 6N HCl (11 mL) and the solution was stirred at room temperature overnight. The solvent was removed in vacuo and the residue dissolved in water. The aqueous solution was extracted with Et$_2$O, the pH was adjusted to 14 with 5N sodium hydroxide and the mixture was extracted with EtOAc. The combined EtOAc extracts were washed with saturated sodium chloride solution, dried (MgSO$_4$), filtered and concentrated in vacuo to provide the title compound (9.0 g, 99%). $^1$H-NMR (CDCl$_3$): δ 1.80–1.96 (m, 2H, CH) 2.53 (s, 3H, OH, NH) 2.71–2.75 (m, 1H, CH) 2.83–3.00 (m, 2H, CH) 3.49–3.57 (m, 1H, CH) 3.63–3.70 (m, 1H, CH) 7.10–7.15 (dd, 2H, ArH) 7.27–7.30 (dd, 2H, ArH). MS m/z 200 (M+H).

(d) 3-(4-Chlorophenyl)-4-(ethoxycarbonylamino)-1-butanol.

Ethyl chloroformate (4.7 mL, 49.5 mmol) was added dropwise to a stirred cooled (−40° C.) solution of 3-(4-chlorophenyl)-4-amino-1-butanol (9.0 g, 45 mmol) and triethylamine (7.2 mL, 51.8 mmol) in DCM (125 mL). The solution was stirred at room temperature for 30 min and poured into 1N HCl (60 mL). The organic layer was washed with 1N HCl (70 mL), saturated sodium bicarbonate (70 mL) and saturated sodium chloride; dried (MgSO$_4$), filtered and the solvent removed to provide the title compound (11.4 g, 93%) as a yellow oil. $^1$H-NMR (CDCl$_3$): δ 1.18–1.23 (t, 3H CH) 1.75–1.84 (m, 1H, CH) 1.90–1.99 (m, 1H, CH) 2.94–2.99 (m, 1H, CH) 3.21–3.30 (m, 1H, CH) 3.47–3.65 (m, 3H, CH) 4.04–4.11 (q, 2H, CH) 4.58 (s, 1H, OH or NH) 7.12–7.15 (d, 2H, ArH) 7.26–7.37 (m 2H, ArH); MS m/z 272 (M+H).

(e) 3-(4-Chlorophenyl)-4-N-methylamino-1-butanol.

This material has been reported (H. Kubota, A. Kafefuda, H. Nagaoka, O. Yamamoto, K. Ikeda, M. Takeuchi, T. Shibanuma, Y. Isomura, Chem. Pharm. Bull., 46(2), 242–254 (1998)); however, the preparation was not exemplified and is therefore presented here. To a stirred cooled (0° C.) mixture of lithium aluminum hydride (3.36 g, 93 mmol) and THF (55 mL) was added dropwise a solution 3-(4-chlorophenyl)-4-(ethoxycarbonylamino)-1-butanol (11.4 g, 42 mmol) in THF (110 mL). The mixture was heated under reflux for 1 h, cooled (ice bath) and saturated sodium sulfate (14 mL) was added. The mixture was stirred at room temperature for 30 min and sodium sulfate (14 g) was added. The mixture was stirred at room temperature for 30 min, filtered through Celite, washed with THF, and the filtrate concentrated in vacuo. Chromatography (1–10% methanol in DCM) provided the title compound (5.85 g, 65%) as a yellow oil. $^1$H-NMR (CDCl$_3$) δ 1.86–1.94 (m, 2H, CH) 2.44 (s, 3H, CH) 2.69–2.86 (m, 5H, CH, OH and NH) 3.51–3.58 (m, 1H, CH) 3.66–3.77 (m, 1H, CH) 7.09–7.12 (d, 2H, CH) 7.25–7.29 (d, 2H, CH). MS m/z 214 (M+H).

(f) N-[2-(4-Chlorophenyl)-4-hydroxybutyl]-N-methyl-3-nitro-1-naphthalenecarboxamide.

To a stirred mixture of 3-nitro-1-naphthoic acid (Kice, J L, Lotey H; J. Org. Chem., 54, 3596 (1989) (0.76 g, 3.5 mmol) in dry DCM (12 mL) was added oxalyl chloride (0.38 mL, 4.38 mmol) and DMF (30 μL). The solution was stirred at room temperature for 3 h and concentrated to provide the acid chloride (0.824 g, quantitative) as a off-white solid which was used without further purification. To a stirred, cooled (0° C.) mixture of 3-(4-chlorophenyl)-4-methylamino-1-butanol (0.745 g, 3.5 mmol), DCM (30 mL) and 1N NaOH (4.37 mL) was added dropwise a solution of 3-nitro-1-naphthoyl chloride (0.824 g, 3.5 mmol) in DCM (12 mL). The mixture was stirred at 0° C. for 2.5 h, water added, the layers separated and the aqueous layer was extracted with DCM. The combined organic extracts were dried (MgSO$_4$). filtered, and concentrated in vacuo. Chromatography (0%, 50%, 100% EtOAc in Et$_2$O,) provided the title compound (1.25 g, 87%) as a light yellow solid. MS m/z 413 (M+H).

(g) N-[2-(4-Chlorophenyl)-4-oxobutyl]-N-methyl-3-nitro-1-naphthamide.

To a stirred cooled (−78° C.) solution of oxalyl chloride (0.4 mL, 4.55 mmol) in DCM (10 mL) was added a solution of DMSO (0.64 mL, 9.10 mmol) in DCM (5 mL). The solution was stirred at −78° C. for 5 min and a solution of N-[2-(4-chlorophenyl)-4-hydroxybutyl]-N-methyl-3-nitro-1-naphthalenecarboxamide (1.25 g, 3.03 mmol) in DCM (6 mL) and DMSO (3.4 mL) was added dropwise. The solution was stirred at −78° C. for 15 min and triethylamine (2.54 mL, 18.2 mmol) was added. The solution was then stirred at −78° C. for 30 min and at room temperature for 2 h. DCM (75 mL) and 1N HCl (75 mL) were added, the layers separated, and the organic layer was dried ($MgSO_4$), filtered, and concentrated in vacuo. Chromatography (silica gel; DCM in $Et_2O$, 1:1) provided the desired compound (1.15 g, 92%) as a light yellow solid. MS m/z 411 (M+H).

Example 4

N-[2-(4-Chlorophenyl)-4-[4-[(S)-2-methylsulfinylphenyl]-1-piperidinyl]butyl]-N-methyl-3-cyano-1-naphthamide Citrate Using standard reductive amination conditions 4-[(S)-2-methylsulfinylphenyl]-piperidine (Shenvi, A B; Jacobs, R T; Miller, S C; Ohnmacht, C J, Jr.; Veale, C A., WO 9516682) was reacted with N-[2-(4-chlorophenyl)-4-oxobutyl]-N-methyl-3-cyano-1-naphthalenecarboxamide and converted to the citrate salt. $^1$H NMR ($CDCl_3$) (amide rotational isomers evident) δ 8.19 (s), 7.92 (m), 7.67–7.32 (br m), 6.98–6.58 (br m), 4.49–3.98 (br m), 3.49–1.25 (br m), 0.87 (t, J=7.5); MS m/z 598.3 (M+H).

The requisite aldehyde was prepared as follows.
(a) N-[2-(4-Chlorophenyl)-4-hydroxybutyl]-N-methyl-3-cyano-1-naphthamide.

Oxalyl chloride (195 μL, 2.23 mmol) was added to a solution of 3-cyano-1-naphthoic acid (Example 1, sub-part (c)) (400 mg, 2.03 mmol) in DCM (10 mL). The solution was stirred for three hours, during which time three portions (30 μL each) of 10% DMF in DCM were added. The solution was concentrated to a white powder under reduced pressure, dried under vacuum, and dissolved in DCM (15 mL). After cooling to 0° C., N-[2-(4-chlorophenyl)-4-hydroxybutyl]-N-methylamine (Example 3) (434 mg, 2.03 mmol, dissolved in 5 mL DCM) and NaOH (1.0 M, 2.54 mL) were added. After warming to room temperature stirring was continued overnight. The mixture was extracted with 30 mL portions of 0.5 M HCl and saturated sodium bicarbonate, dried ($MgSO_4$), filtered, and concentrated under reduced pressure to a light yellow foam (692 mg, 1.76 mmol, 87%). $^1$H NMR ($CDCl_3$) (amide rotational isomers evident) δ 8.09 (s), 7.85 (m), 7.72–7.50 (br in), 7.43–4.35 (br in), 6.92 (d, J=6.3), 6.85 (d, J=7.8), 6.69 (m), 6.65 (m), 4.57 (br m), 3.99 (br m), 3.70 (m). 3.50–3.10 (br m), 2.67 (s), 2.03 (m), 1.89 (m), 1.58 (m); MS m/z 393.0 (M+H).

(b) N-[2-(4-Chlorophenyl)-4-oxobutyl]-N-methyl-3-cyano-1-naphthamide.

A solution of DMSO (356 μL, 5.01 mmol) in DCM (5 mL) was added dropwise over 5 min to a stirred solution of oxalyl chloride (219 μL, 2.51 mmol) in DCM (5 mL) at −70° C.

After stirring for 15 min, N-[2-(4-chlorophenyl)-4-hydroxybutyl]-N-methyl-3-cyano-1-naphthamide (788 mg, 2.01 mmol) was added dropwise as a solution in DCM (5 mL).

Stirring was continued for 45 min at −70° C., warmed to −45° C., and stirred for 30 min.

The solution was cooled to −70° C. and triethylamine (1.41 mL, 10.03 mmol) (dissolved in 5 mL of DCM) was added dropwise. After stirring 15 min, the mixture was allowed to warm to room temperature, diluted with DCM, and extracted with 0.5 M HCl (30 mL), saturated sodium bicarbonate (30 mL), dried ($MgSO_4$), and concentrated to a clear oil which was purified by chromatography (50% EtOAc in hexanes) to afford the product as a clear oil (543 mg, 1.39 mmol, 70%). $^1$H NMR ($CDCl_3$) (amide rotational isomers evident) δ 9.71 (s), 9.60 (s), 8.18 (m), 7.86 (t, J=7.8), 7.68–7.29 (m), 7.51 (m), 6.87, (t, J=7.2), 6.67 (d, J=8.4), 6.57 (m), 4.56 (br m), 3.98, (br m), 3.71, (br m), 3.42 (m), 2.97, (m), 2.67 (m); MS m/z 391.0 (M+H).

Example 5

N-[(S)-2-(3,4-Dichlorophenyl)-4-4-2-methylsulfinyl-6-fluorophenyl]-1-piperidinyl]-butyl]-N-methyl-3-cyano-1-naphthamide Citrate Using standard reductive amination conditions N-[(S)-2-(3,4-dichlorophenyl)-4-oxo-butyl]-N-methyl-3-cyano-1-naphthamide was reacted with 4-(2-methylsulfinyl-6-fluorophenyl)-piperidine and converted to the citrate salt. MS m/z 650 (M+H); analysis for $C_{35}H_{34}Cl_2N_3O_2SF.1.05$ $C_6H_8O_7.1.1$ $H_2O$; calculated; C, 56.87; H; 5.15; N, 4.81; found; C, 59.88; H, 5.16; N, 4.71.

The requisite 4-(2-methylsulfinyl-6-fluorophenyl)-piperidine was prepared as follows.
(a) 4-(2,6-Difluorophenyl)-pyridine.

To a stirred mixture of 4-bromo-pyridine hydrochloride (1.12 g, 5.76 mmol), tetrakis(triphenylphosphine) palladium (0.2 g, 0.173 mmol), benzene (12.5 mL) and sodium carbonate (2.14 g, 20.2 mmol) in water (10 mL) was added 2,6-difluorobenzene boronic acid (1.0 g, 6.33 mmol) in ethanol (3 mL). The mixture was heated under reflux overnight, extracted with EtOAc, dried ($MgSO_4$), filtered, concentrated, and purified by chromatography to afford the product as a white solid (0.19 g, 16%). $^1$H NMR ($CDCl_3$) δ 8.71 (d. 2H), 7.40 (m, 3H), 7.05 (t, 2H). MS m/z 192 (M+H).
(b) 4-(2-Thiomethyl-6-fluorophenyl)-pyridine.

A mixture of 4-(2,6-difluorophenyl)-pyridine (0.45 g, 2.35 mmol), methyl mercaptan sodium salt (0.21 g, 3.00 mmol) in DMF (10 mL) was heated at 100° C. overnight. The mixture was diluted with EtOAC and saturated NaCl, the organic layer was dried, filtered, concentrated, and purified by chromatography to afford the product as a yellow solid (0.44 g, 85%). $^1$H NMR ($CDCl_3$) δ 8.71 (d, 2H), 7.32 (m, 3H), 7.07 (d, 1H), 6.97 t, 1H), 2.39 (s, 3H), MS m/z 220 (M+H).
(c) 4-(2-Thiomethyl-6-fluoro-phenyl)-piperidine.

A mixture of 4-(2-thiomethyl-6-fluorophenyl)-pyridine (0.54 g, 2.46 mmol). HCl (0.5 mL) and $PtO_2$ (0.54 g) in ethanol (20 mL) was shaken under hydrogen (50 psi) for 22 h. The mixture was filtered through Celite, washed with ethanol, concentrated and diluted with EtOAc and saturated $NaHCO_3$. The organic layer was dried, filtered, concentrated, and purified by chromatography to afford the product as pink solid (0.14 g, 25%). $^1$H NMR ($CDCl_3$) δ 7.16 (m, 1H), 7.97 (d, 1H) 6.80 (m, 1H), 3.17 (m, 2H), 2.70 (t, 2H), 2.46 (s, 3H), 2.08 (q, 2H), 1.70 (m, 4H). MS m/z 226 (M+H).
(d) 4-(2-Methylsulfinyl-6-fluoro-phenyl)-piperidine.

A solution of 4-(2-thiomethyl-6-fluoro-phenyl)-piperidine (0.14 g, 0.62 mmol), $Et_2O$ (5 mL), and 1N HCl in $Et_2O$ (0.7 mL, 0.68 mmol) was stirred 5 min at room temperature and evaporated. To the residue in dioxane (3.7 mL) and ethanol (1.8 mL) was added sodium periodate (0.14 g, 0.654 mmol) in water (1 mL) at 0° C. The reaction mixture was stirred at room temperature for 9 days. Solvent was evaporated and the residue was dissolved in methanol (5 mL). KOH (0.035 g, 0.62 mmol) in methanol (2 mL) was added and the solution was filtered. The filtrate was concentrated and redissolved in DCM. The solution was filtered again and the filtrate was concentrated to give the product as light yellow oil (0.15 g, quantitative). $^1$H NMR (CDCl$_3$) δ 7.81 (d, 1H), 7.44 (m, 1H), 7.16 (m, 1H), 3.22 (m, 2H), 2.70 (m, 5H), 2.18 (m, 2H), 1.84 (s, 2H), 1.74 (d, 1H), 1.56 (d, 1H). MS m/z 242 (M+H).

Example 6

N-[2-(S)-(3,4-Dichlorophenyl)-4-[4-[2-methylsulfinyl-5-bromophenyl]-1-piperidinyl]-butyl]-N-methyl-3-cyano-1-naphthamide Citrate Using standard reductive amination conditions N-[2-(S)-(3,4-dichlorophenyl)-4-oxo-butyl]-N-methyl-3-cyano-1-naphthamide was reacted with 4-(2-methylsulfinyl-5-bromo-phenyl)-piperidine and converted to the citrate salt. MS m/z 712 (M+H).

The requisite 4-(2-methylsulfinyl-5-bromophenyl)-piperidine was prepared as follows.
(a) N-Phenylmethoxy-carbonyl-4-(2-methylthio-5-bromophenyl)-piperidine.

A solution containing N-phenyl-methoxy-carbonyl-4-(2-methylthiophenyl)-piperidine (Jacobs, R; Shenvi, A; EP 630887) (100 mg) in glacial acetic acid (0.50 mL) was frozen in a dry-ice/acetone cooling bath. To the frozen mixture was added a solution of bromine (68 mg) in glacial acetic acid (1.00 mL) over 5 min. The reaction was warmed to room temperature over 1 h, heated at 40° C. for 30 min, cooled to 0° C., then poured into crushed ice (25 mL).

The mixture was extracted with EtOAc (30 mL), washed with water (15 mL), saturated NaHCO$_3$ (3×15 mL) and brine (15 mL), dried (MgSO$_4$), filtered, and concentrated under reduced pressure to afford the product as an oil (60 mg). $^1$H NMR (CDCl$_3$) δ 1.51 (m, 2H), 1.75 (m, 2H), 2.82 (br s, 2H), 3.04 (m, 1 H), 4.26 (br s, 2H), 5.08 (s, 2H), 6.99 (dd, J=9.0, 3.0, 1H), 7.18 (d, J=2.1, 1H), 7.23 (dd, J=9.0, 3.0, 1H), 7.29 (m, 5H); MS m/z 442, 444 (M+Na).
(b) N-Phenylmethoxy-carbonyl-4-(2-methylsulfinyl-5-bromophenyl)-piperidine.

To a solution containing N-phenyl-methoxy-carbonyl-4-(2-methylthio-5-bromophenyl)-piperidine (0.202 g) in methanol (0.67 mL), DCM (0.33 mL), and glacial acetic acid (1.0 mL) was added 30% H$_2$O$_2$ (48 μL) dropwise and stirred at room temperature for 18 h, then cooled and poured into ice-cold water (50 mL). The mixture was extracted with EtOAc (3×75 mL), washed with saturated NaHCO$_3$ (2×20 mL), dried (MgSO$_4$), filtered, concentrated, and purified by chromatography (1:1 hexane:EtOAc, then EtOAc) to afford the product (250 mg) as a white solid. $^1$H NMR (CDCl$_3$) δ 1.66 (br m, 2H), 1.87 (m, 2H), 2.70 (s, 3H), 2.90 (br m, 3H), 4.36 (br s, 2H), 5.17 (s, 2H), 7.39 (m, 6H), 7.61 (dd, J=8.7, 2.1, 1H). 7.87 (d, J=8.4, 1H); MS m/z 458, 460 (M+Na).
(c) 4-(2-Methylsulfinyl-5-bromophenyl)-piperidine trifluoroacetate.

A solution containing N-phenyl-methoxy-carbonyl-4-(2-methylsulfinyl-5-bromophenyl)-piperidine (125 mg) in trifluoroacetic acid (7.0 mL) was heated to 80° C. for 45 min.

The reaction was cooled in an ice bath, diluted with DCM (25 mL), and concentrated.

The residue was re-dissolved and concentrated with three portions of DCM (20 mL) to afford the product as a tan oil (140 mg). $^1$H NMR (CDCl$_3$) δ 1.91 (br m, 1H), 2.21 (m, 3H), 2.83 (s, 3H), 3.18 (br m, 3H), 3.52 (br s, 2H), 7.53 (s, 1H), 7.69 (d, J=7.5, 1H), 7.87 (d, J=8.4, 1H), 8.53 (br s, 1H), 8.83 (br s, 1H); MS m/z 302, 304 (M+H).

Example 7

N-[2-(S)-(3,4-Dichlorophenyl)-4-[4-[(R,S)-2-methylsulfinylphenyl]-1-piperidinyl]butyl]-N-methyl-3-cyano-1-naphthamide Citrate Hydrate Using standard reductive amination conditions (except that acetic acid-sodium acetate buffer was substituted for acetic acid) N-[(S)-2-(3,4-dichlorophenyl)-4-oxobutyl]-N-methyl-3-cyano-1-naphthamide (255 mg, 0.60 mmol) was reacted with 4-[(RS)-2-methylsulfinyl-phenyl]piperidine (Shenvi, A B; Jacobs, R T; Miller, S C; Ohnmacht, C J Jr; Veale, C A.: WO 9516682) (201 mg, 0.595 mmol). converted to the citrate salt, and isolated by filtration from Et$_2$O to afford the title compound (290.7 mg) as a white powder. MS m/z 632 (M+H); analysis for C$_{35}$H$_{35}$Cl$_2$N$_3$O$_2$S .C$_6$H$_8$O$_7$.H$_2$O: calculated: C, 58.43; H, 5.38; N, 4.98; found: C, 58.20; H, 5.28; N, 4.95.

Example 8

N-[2-(S)-(3,4-Dichlorophenyl)-4-[4[(R)-2-methylsulfinylphenyl]-1-piperidinyl]butyl]-N-methyl-3-cyano-1-naphthamide Citrate Hydrate Using standard reductive amination conditions (except that acetic acid-sodium acetate buffer was substituted for acetic acid) N-[(S)-2-(3,4-dichlorophenyl)-4-oxobutyl]-N-methyl-3-cyano-1-naphthamide (468 mg, 1.1 mmol) was reacted with 4-[(R)-2-methylsulfinylphenyl]-piperidine (piperidine (Shenvi, A B; Jacobs, R T; Miller, S C; Ohnmacht. C J Jr; Veale, C A.; WO 9516682) (232 mg, 1.04 mmol), converted to the citrate salt, and isolated by filtration from Et$_2$O to afford the title compound (651.2 mg) as a white powder. MS m/z 632 (M+H); analysis for C$_{35}$H$_{35}$Cl$_2$N$_3$O$_2$S .C$_6$H$_8$O$_7$.H$_2$O: calculated: C, 58.43; H, 5.38; N, 4.98; found: C, 58.10; H, 5.20; N. 4.82.

Example 9

N-[(S)-2-(3,4-Dichlorophenyl)-4-[4-[(S)-2-methylsulfinylphenyl]-1-piperidinyl]butyl]-N-methyl-6-cyano-1-naphthamide Citrate Using standard acylation conditions 6-cyano-1-naphthoyl chloride (prepared from 6-cyanonaphthoic acid using oxalyl chloride) was reacted with N-[(S)-2-(3,4-dichlorophenyl)-4-[4-[(S)-2-methylsulfinylphenyl]-1-piperidinyl]butyl]-N-methylamine (Example 1, sub-part (b)) and the product was converted to the citrate salt. Analysis for C$_{35}$H$_{35}$Cl$_2$N$_3$O$_2$S10.C$_6$H$_8$O$_7$0.9.H$_2$O: calculated: C, 58.56; H, 5.37; N, 5.00. found: C, 58.64; H, 5.23; N, 4.81.

The intermediate 6-cyano-1-naphthoic acid was prepared as described below and proved to be advantageous over a previously published method (Dewar, M J S and Grisdale, P J; J. Amer Chem. Soc., 84, 3541 (1962)).
(a) Methyl 6-hydroxy-1-naphthoate.

To a stirred solution of 6-hydroxy-1-naphthoic acid (2.5 g, 13.3 mmol) in DCM (44 mL) was added oxalyl chloride (1.45 mL, 16.6 mmol) and 2 drops of DMF. The solution was stirred at room temperature for 4.5 h and concentrated. Methanol (20 mL) was added to the reaction mixture and the solution was heated under reflux for 15 min. The solution was cooled to room temperature and concentrated in vacuo. Chromatography (silica gel; 1% and 2% methanol in DCM) provided the title compound as a yellow solid (2.22 g, 83%).

¹H-NMR (CDCl₃) δ 4.00 (s, 3H, CH₃) 5.54 (s, 1H, OH) 7.20–7.26 (m, 2H, ArH) 7.41–7.4 (t, 1H, ArH) 7.83–7.86 (dd, 1H, ArH) 8.01–8.04 (dd, 1H, ArH) 8.80–8.85 (d, 1H, ArH). MS m/z 203 (M+H).

(b) Methyl 6-trifluoromethylsulfonyloxy-1-naphthoate.

To a stirred cooled (0° C.) solution of methyl 6-hydroxy-1-naphthoate (2.15 g, 10.6 mmol) in DCM (50 mL) was added triethylamine (1.48 mL, 10.6 mmol) and trifluoromethanesulfonic anhydride (1.79 mL, 10.6 mmol). The solution was poured into saturated sodium bicarbonate, the layers separated and the aqueous layer was extracted with EtOAc.

The combined organic layers were dried (MgSO₄), filtered and concentrated in vacuo to provide the title compound as a yellow oil (4.23 g). ¹H-NMR (CDCl₃) (contains triethylamine) δ 4.00 (s, 3H, CH₃) 7.48–7.52 (dd, 1H, ArH) 7.60–7.65 (t, 1H, ArH) 7.80–7.81 (d, 1H, ArH) 8.04–8.07 (d, 1H, ArH) 8.28–8.32 (d, 1H, ArH) 9.06–9.09 (d, 1H, ArH). MS m/z 335 (M+H).

(c) Methyl 6-cyano-1-naphthoate.

To a stirred solution of methyl 6-trifluoromethylsulfonyloxy-1-naphthoate (3.5 g, 10.5 mmol) in DMF (14 mL) was added zinc cyanide (0.86 g, 7.33 mmol) and tetrakis(triphenylphosphine) palladium (0.48 g, 0.415 mmol). The solution was heated at 80° C. for 45 min and poured into a solution of saturated sodium bicarbonate. The mixture was extracted with EtOAc, the combined organic layers were dried (MgSO₄), filtered, and concentrated in vacuo. Chromatography (silica gel; EtOAc in hexane, 1:9) provided the title compound (1.00 g, 45% over 2 steps) as a white solid. ¹H-NMR (CDCl₃) δ 4.03 (s, 3H, CH) 7.65–7.67 (t, 1H, ArH) 7.73–7.76 (dd, 1H, ArH) 8.07–8.10 (d, 1H, ArH) 8.28 (d, 1H, ArH) 8.35–8.38 (d, 1H, ArH) 9.10 (d, 1H, ArH). MS m/z 212 (M+H).

(d) 6-Cyano-naphthoic acid.

To a stirred solution of methyl 6-cyano-1-naphthoate (1.0 g, 4.73 mmol) in THF (55 mL) and water (22 mL) was added 1N NaOH (10 mL, 9.93 mmol) and enough methanol to clarify the solution. The solution was stir-red at room temperature overnight and concentrated in vacuo. The aqueous residue was acidified to pH 1 with 1N HCl and extracted with EtOAc.

The combined organic layers were dried (MgSO₄), filtered and concentrated in vacuo to provide the desired compound (0.767 g, 82%) as a white solid. ¹H-NMR (DMSO d₆) δ 7.75–7.80 (t, 1H, ArH) 7.91–7.95 (dd, 1H, ArH) 8.25–8.36 (m, 2H, ArH) 8.71 (d, 1H, ArH) 9.02–9.08 (d, 1H, ArH) 13.4 (s, 1H, acid). MS m/z 196 (M-1).

Example 10

N-[(S)-2-(3,4-Dichlorophenyl)-4-[4-[(S)-2-methylsulfinylphenyl]-1-piperidinyl]butyl]-N-methyl-4-cyano-1-naphthamide Citrate A mixture containing 4-cyano-1-naphthoic acid (0.090 g, 0.45 mmol), DCM (3 mL), oxalyl chloride (0.063 g, 0.50 mmol) and DMF (approximately 5 μL) was stirred for 3 h and concentrated to provide 4-cyano-1-naphthoyl chloride as an off-white solid which was used directly. Using standard acylation conditions 4-cyano-1-naphthoyl chloride (0.090 g) was reacted with N-[(S)-2-(3,4-dichlorophenyl)-4-[4-[(S)-2-methylsulfinylphenyl]-1-piperidinyl]butyl]-N-methylamine to afford the free base (0.215 g) which was converted to the citrate salt.

MS m/z 631 (M+H).

The requisite 4-cyano-1-naphthoic acid was prepared as follows.

(a) Methyl 4-bromo-1-naphthoate.

A solution of 4-bromo-1-naphthoic acid (Fischer, A; et al, J. Chem. Soc., 1426 (1958)) oxalyl chloride (2.56 g), and DMF (5 μL) in DCM (100 mL) was stirred for 3 h, concentrated, then redissolved in DCM (5 mL). Methanol was added and stirring continued overnight.

Following concentration and purification by chromatography (DCM) the product was afforded as a white solid (4.85 g). ¹H NMR (DMSO-d₆): δ 8.83–8.77 (m, 1H), 8.31–8.25 (m, 1 H), 8.01 (s, 1 H), 7.82–7.75 (m, 2H), 3.96 (s, 3 H); MS m/z 265 (M+H).

(b) 4-cyano-1-naphthoic acid.

A solution of methyl 4-bromo-1-naphthoate (0.509 g) copper (I) cyanide, (0.174 g), 1 drop of pyridine, and DMF (5 mL) was heated under reflux at 180° C. for 5 h. The hot solution was poured into 10 mL of aqueous concentrated NH₄OH and extracted with DCM.

The organic phase was washed successively with 1N HCl (20 mL) and brine (40 mL), dried (Na₂SO₄), filtered, and concentrated to afford methyl 4-cyano-1-naphthoate a colorless oil (0.213 g). MS m/z 196 (M-1). ¹H NMR (DMSO₆): δ 8.74–8.69 (m, 1 H), 8.29–8.15 (m, 3 H), 7.92–7.83 (m, 2H), 3.99 (s, 3 H). The methyl ester was saponified by stirring a solution of the methyl ester, LiOH.H₂O (1 equivalent), THF (3 mL), water (1 mL) and methanol (1 mL) overnight at room temperature. The solution was diluted with saturated sodium bicarbonate and extracted with Et₂O. The aqueous layer was acidified to pH 2 by addition of 1N HCl and extracted with Et₂O. The organic layer was washed with water (30 mL) and brine (40 mL), dried (sodium sulfate), filtered, and concentrated to afford 4-cyano-1-naphthoic acid as an oil.

Example 11

N-[(S)-2-(3,4-Dichlorophenyl)-4-[4-[(S)-2-methylsulfinylphenyl]-1-piperidinyl]-butyl]-N-methyl-3,6-dicyano-1-naphthamide Citrate Using standard acylation conditions N-[(S)-2-(3,4-dichlorophenyl)-4-[4-[(S)-2-methylsulfinylphenyl]-1-piperidinyl]butyl]-N-methylamine was reacted with 3,6-dicyano-1-naphthoyl chloride (prepared from 3,6-dicyano-1-naphthoic acid using oxalyl chloride) and the product was converted to the citrate salt. MS m/z 657.2 (M+H).

The requisite carboxylic acid was prepared as follows.
(a) 3-Cyano-6-methoxy-1-naphthoic acid.

A solution of ethyl 3-bromo-6-methoxy-1-naphthoate (Wrobel, et al; J. Med. Chem. 34, 2504 (1991) (206 mg, 0.66 mmol), Zn(CN)₂, and tetrakis(triphenylphosphine) palladium (36 mg, 0.031 mmol) in DMF (12 mL) was stirred at 80° C. for 1 h. The mixture was diluted with DCM, washed with water, dried (MgSO₄), filtered and concentrated to a yellow precipitate, and purified by chromatography (5% EtOAc in hexanes) to afford methyl 3-cyano-6-methoxy-1-naphthoate as a white powder (150 mg, 0.588 mmol, 88%). The ester was saponified by stirring in 2% water in THF with 1.5 equivalents of LiOH at 80° C. for 3 h to afford the title compound. ¹H NMR (CDCl₃) δ 8.99 (d, J=9.6, 1H), 8.33 (s, 1H), 7.45 (dd, J=9.3, 2.7, 1H), 7.26 (s, 1H), 7.22 (d, J=2.4, 1H).

(b) 3-Cyano-6-hydroxy-1-naphthoic acid.

A mixture of ethyl 3-cyano-6-methoxy-1-naphthoate (715 mmol, 2.80 mmol) and pyridine hydrochloride (4.0 g) was heated at 200° C. for 3 h. After cooling the solid was dissolved in 1N HCl and extracted into DCM, dried (MgSO₄), filtered and concentrated to a tan precipitate (559 mg, 2.62 mmol, 94%). ¹H NMR (DMSO d₆) δ 10.38 (s, 1H), 8.73 (d, J=9.3, 1H), 8.61 (s, 1H), 8.03 (s, 1H), 7.38 (m, 2H).

(c) Ethyl 3-cyano-6-hydroxy-1-naphthoate.

To a stirred solution 3-cyano-6-hydroxy-1-naphthoic acid (363 mg, 1.70 mmol), oxalyl chloride (1.0 mL) in DCM (15 mL) was added 3 drops of DMF over 2 h. The solvent was removed under reduced pressure, methanol (20 mL) was added, followed by triethylamine (0.5 mL). After stirring for 2 h the solvent was removed under reduced pressure, the residue was dissolved in DCM, washed with 1N HCl, then saturated sodium bicarbonate, dried (MgSO$_4$), and concentrated to a yellow precipitate (346 mg, 1.52 mmol, 89%). $^1$H NMR (CDCl$_3$) δ 88.92 (d, J=9.3, 1H), 8.21 (s, 1H), 8.17 (s, 1H), 7.37 (dd, J=9.3, 2.1, 1H), 7.26 (s, 2H), 4.02 (s, 3H).

(d) Ethyl 3-cyano-6-trifluoromethylsulfonyloxy-1-naphthoate.

To a cooled (0° C.) solution of ethyl 3-cyano-6-hydroxy-1-naphthoate (346 mg, 1.52 mmol) and triethylamine (254 μL) in DCM was added trifluoromethanesulfonic anhydride (307 μL). The mixture was allowed to warm to room temperature with mixing, and after 2 h was quenched by addition of methanol (2 mL), concentrated, and purified by chromatography (20% EtOAc in hexanes) to afford the product as a white precipitate (438 mg, 1.22 mmol, 80%). $^1$H NMR (CDCl$_3$) δ 9.20 (d, J=9.6, 1H), 8.41 (s, 1H), 7.88 (d, J=2.7, 1H), 7.66 (dd, J=9.6, 2.7, 1H), 4.06 (s, 3H).

(e) Ethyl 3,6-dicyano-1-naphthoate.

A solution of ethyl 3-cyano-6-trifluoromethylsulfonyloxy-1-naphthoate (438 mg, 1.22 mmol), Zn(CN)$_2$ (86 mg, 0.732 mmol) and tetrakis (triphenylphosphine) palladium (59 mg, 0.051 mmol) in DMF (8 mL) was stirred at 80° C. for I h. The mixture was diluted with Et$_2$O, washed with water, dried, (MgSO$_4$), filtered, and concentrated. Following chromatographic purification (DCM) the product was recovered as a white powder (267 mg, 1.13 mmol, 93%). $^1$H NMR (CDCl$_3$) δ 9.18 (d, J=9.0, 1H), 8.50 (s, 1H), 8.45 (s, 1H), 8.34 (s, 1H), 7.91 (dd, J=9.0, 1.5, 1H), 4.06 (s, 3H). The ester was saponified by stirring with 1.2 equivalents of LiOH in 3% water in THF at 80° C. for 2 h. The mixture was concentrated under reduced pressure and diluted with DCM resulting in precipitation of the desired product which was isolated as a white powder by filtration.

Example 12

N-[2-(S(3,4-Dichlorophenyl)-4-[4-[(S)-2-methylsulfinylphenyl]-1-piperidinyl]butyl]-N-methyl-3,4-dicyano-1-naphthamide Citrate Hydrate To a stirred solution of 3,4-dicyano-1-naphthoic acid (121 mg, 0.542 mmol) in dry DCM (5 mL) was added oxalyl chloride (80.0 mg, 0.63 mmol) and DMF (10 μL). After 3 h at room temperature DCM was removed in vacuo to afford 3,4-dicyano-1-naphthoyl chloride.

Using standard acylation conditions 3,4-dicyano-1-naphthoyl chloride was reacted with N-[(S)-2-(3,4-dichlorophenyl)-4-[4-[(S)-2-methylsulfinylphenyl]-1-piperidinyl]butyl]-N-methylamine (271 mg, 0.597 mmol), converted to the citrate salt, and isolated by filtration from Et$_2$O to afford the title compound (291.7 mg) as a white powder. MS m/z 657 (M+H); analysis for C$_{36}$H$_{34}$Cl$_2$N$_4$O$_2$S.C$_6$H$_8$O$_7$.H$_2$O: calculated: C, 58.13; H, 5.11; N, 6.46; found: C, 58.20; H, 5.03; N, 6.36.

The required 3,4-dicyano-1-naphthoic acid was prepared as follows.

3,4-Dicyano-]-naphthoic acid.

A mixture containing methyl 3,4-dibromo-1-naphthoate (126 mg, 0.366 mmol), copper (I) cyanide (618 mg, 6.89 mmol), pyridine (0.1 mL), and dry N-methylpyrrolidinone (2.0 mL) was heated at approximately 150° C. for 1 h. cooled to room temperature, diluted with water, NH$_4$OH and EtOAc. The mixture was stirred briefly and filtered. The organic phase was separated and the aqueous phase extracted with additional EtOAc. The combined organic extracts were washed (dilute aqueous NH$_4$OH and saturated NaHCO$_3$). dried (Na$_2$SO$_4$), filtered, and EtOAc was removed in vacuo. The products were separated by chromatography (5–15% EtOAc in hexane and hexane:DCM (2:1)) to afford methyl 3,4-dicyano-1-naphthoate (22 mg; 25%) [$^1$H NMR (CDCl$_3$) δ 9.01 (m, 1H), 8.41 (m, 1H), 8.36 (s, 1H), 7.9 (m, 2H), 4.08 (s, 3H); MS (EI) m/z 236 (M)], methyl 3-bromo-4-cyano-1-naphthoate (21.9 mg; 20.6%) [$^1$H NMR (CDCl$_3$) δ 8.86 (m, 1H), 8.31 (s, 1H), 8.28 (m, 1H). 7.75 (m, 2H), 4.05 (s, 3H); MS (EI) m/z 289 (M).], and methyl 4-bromo-3-cyano-1-naphthoate (28.3 mg; 26.6%) [$^1$H NMR (CDCl$_3$) δ 9.02 (m, 1H), 8.43 (m, 1H), 8.28 (s, 1H), 7.8 (m, 2H) 4.04 (s, 3H); MS (EI) m/z 289 (M)]. The esters were separately saponified by stirring with 1.1–1.2 equivalents of LiOH in THF:water:methanol (20:10:1) at room temperature. The solutions were concentrated in vacuo, diluted with additional water, acidified with 1N HCl, extracted with EtOAc, dried (Na$_2$SO$_4$), filtered, and the EtOAc was removed in vacuo to afford the individual carboxylic acids. Prior to use, the 3,4-dicyano-1-naphthoic acid was further purified by chromatography (10–20% methanol in DCM) to afford the title compound (15.3 mg, 87%) as an off-white solid. MS (EI) m/z 222 (M).

The required 3,4-dibromo-1-naphthoate was prepared as follows.

(a) Methyl 3,4-dibromo-1-naphthoate.

To a stirred mixture of anhydrous cupric bromide (7.95 g, 35.6 mmol) and dry acetonitrile (30 mL) was added a solution of methyl 3-amino-1-naphthoate (Adcock, W; Dewar, M J S; J. Am. Chem. Soc., 89, 386 (1967)) (2.35 g, 11.68 mmol) in dry acetonitrile (10 mL). The dark mixture was stirred at room temperature for 2 h, cooled (ice bath) and tert-butyl nitrite (1.83 g, 17.76 mmol) added dropwise over approximately 10 min. The dark green-black mixture was allowed to warm to room temperature and stirred overnight. The mixture was treated with water (100 mL) and 3N HCl (100 mL), concentrated in vacuo, and extracted with DCM. The DCM extracts were washed (saturated NH$_4$Cl), dried (Na$_2$SO$_4$), filtered, DCM was removed in vacuo, and the residue purified by chromatography (4:1 hexane:DCM) to afford the desired compound (3.72 g; 93%) as an off-white solid. $^1$H NMR (CDCl$_3$) δ 8.89 (m, 1H), 8.41 (m, 1H), 8.34 (s, 1H), 7.66 (m, 2H), 4.01 (s, 3H); MS (EI) m/z 344 (M).

Example 13

N-[2-(3,4-Difluorophenyl)-4-[4-[(S)-2-methylsulfinylphenyl]-1-piperidinyl]butyl]-N-methyl-3-nitro-1-naphthamide Citrate Using standard reductive amination conditions 4-[(S)-2-methylsulfinylphenyl]-piperidine (Shenvi, A B; Jacobs, R T; Miller, S C; Ohnmacht, C J, Jr.; Veale, C A., WO 9516682) was reacted with N-[2-(3,4-difluorophenyl)-4-oxobutyl]-N-methyl-3-nitro-1-naphthamide and converted to the citrate salt. MS m/z 620 (M+H). Analysis for C$_{34}$H$_{35}$F$_2$N$_3$O$_4$S.1.0 C$_6$H$_8$O$_7$.1.0 H$_2$O: calculated: C, 57.89; H, 5.47; N, 5.06. found: C, 57.78; H, 5.32; N, 4.96.

The required aldehyde was prepared as follows.

(a) 2-[[3-Cyano-3-(3,4-difluorophenyl)]propyloxy]-2H-tetrahydropyran.

To a stirred cooled (0° C.) mixture of 60% sodium hydride (4.12 g, 103 mmol) in THF (95 mL) was added dropwise a solution of 3,4-difluorobenzyl cyanide (15.0 g, 98 mmol) in THF (25 mL) and the solution was stirred at room temperature for 3 h. The solution was cooled (ice bath) and 2-(2-bromoethoxy)-2H-tetrahydropyran (20.5 g, 98 mmol) was added dropwise and the solution stirred at room temperature overnight. Saturated ammonium chloride was added and the mixture was extracted with EtOAc. The combined organic extracts were dried (MgSO$_4$), filtered, and concentrated in vacuo. Chromatography (20%, 90% and 95% DCM in hexane) provided the title compound (16.05 g, 58%) as a yellow oil. $^1$H-NMR (CDCl$_3$) δ 1.55–1.63 (m, 4H, CH$_2$) 1.75–1.80 (m, 2H, CH$_2$) 2.10–2.19 (m, 2H, CH$_2$) 3.52–3.58 (m, 2H, CH$_2$) 3.82–4.06 (m, 2H, CH$_2$) 4.08–4.11 (t, 1H, CH) 4.56–4.60 (m, 1H, CH) 7.08–7.27 (m, 3H, ArH).

(b) 2-[[4-Amino-3-(3,4-difluorophenyl)]butyloxy]-2H-tetrahydropyran.

To a mixture of Raney Nickel (5.6 g) in ethanol (20 mL) was added 2-[[3-cyano-3-(3,4-difluorophenyl)]propyloxy]-2H-tetrahydropyran (8.34 g, 89.4 mmol) in ethanol (144 mL). Ammonium hydroxide (30%, 120 mL) was added and the mixture was set on Parr apparatus under hydrogen (50 psi) for 4 days. The hydrogenation reaction was combined with a similar reaction (7.70 g, 27.4 mmol of starting nitrile) and filtered through Celite. The filtrate was concentrated, DCM and water were added and the layers separated. The organic layer was washed twice with water, dried (Na$_2$SO$_4$), filtered, and concentrated in vacuo to yield 15.40 g (95%) of the title compound as a yellow oil. MS m/z 286 (M+H).

(c) 4-Amino-3-(3,4-difluorophenyl)-1-butanol.

To a stirred cooled (5° C.) solution of 2-[[4-amino-3-(3, 4-difluorophenyl)]butyloxy]-2H-tetrahydropyran (14.18 g, 49.7 mmol) in methanol (100 mL) was added dropwise 6N HCl (11 mL) and the solution was stirred at room temperature overnight The reaction mixture was poured into water and DCM, and the layers separated. The aqueous phase was basified with 5N NaOH and extracted with DCM. The combined DCM extracts were dried (Na$_2$SO$_4$), filtered, and concentrated in vacuo to provide the title compound as a white solid (8.45 g, 85%). $^1$H-NMR (300 CDCl$_3$) δ 1.80–1.94 (m, 2H, CH$_2$) 2.28 (br s, 3H, NH$_2$, OH) 2.69–2.76 (m, 1H, CH) 2.81–2.88 (dd, 1H, CH) 2.94–2.99 (dd, 1H, CH) 3.49–3.57 (m, 1H, CH) 3.64–3.71 (m, 1H, CH) 6.88–7.18 (m, 3H, ArH). MS m/z 202 (M+H).

(d) 3-(3,4-Difluorophenyl)-4-(ethoxycarbonylamino)-1-butanol.

Ethyl chloroformate (3.9 mL, 40.8 mmol) was added dropwise to a stirred cooled (−40° C.) solution of 4-amino-3-(3,4-difluorophenyl)-1-butanol (7.45 g, 37 mmol) and triethylamine (5.94 mL, 42.6 mmol) in DCM (180 mL). The solution was stirred at room temperature for 30 min and at room temperature overnight. The material was washed twice with 1N HCl, twice with saturated sodium bicarbonate; dried (Na$_2$SO$_4$), filtered and the solvent removed to provide the title compound (8.85 g, 88%) as a yellow oil. $^1$H-NMR (CDCl$_3$) δ 1.18–1.23 (t, 3H, CH) 1.72–1.98 (m, 3H) 2.96–3.00 (m, 1H, CH) 3.24–3.29 (m, 1H, CH) 3.45–4.04 (m, 3H, CH), 4.06–4.14 (m, 2H, CH) 4.66 (br s, 1H, OH or NH) 6.91–7.37 (m, 3H, ArH). MS m/z 274 (M+H).

(e) 3-(3,4-Difluorophenyl)-N-methyl-4-amino-1-butanol.

To a stirred cooled (−10° C.) mixture of lithium aluminum hydride (2.46 g, 65 mmol) and dry THF (50 mL) was added dropwise a solution of 3-(3,4-difluorophenyl)-4-(ethoxycarbonylamino)-1-butanol (8.85 g, 32.4 mmol) in THF (40 mL). The solution was heated under reflux for 1.25 h, cooled (ice bath) and saturated sodium sulfate (150 mL) solution was added dropwise. The mixture was stirred at room temperature for 1 hr, filtered through Celite, washed with THF and the solvent removed in vacuo. The residue was dissolved in DCM, washed with water, dried (Na$_2$SO$_4$), filtered and the solvent removed in vacuo. Purification by chromatography (2–5% and 10% methanol in DCM) provided the title compound (5.20 g, 75%) as a pale green oil. $^1$H-NMR (CDCl$_3$) δ 1.85–1.96 (m, 2H, CH) 2.45 (s, 3H, CH$_3$) 2.74–2.85 (m, 3H, CH) 3.37 (br s, 2H, NH, OH) 3.50–3.58 (m, 1H, CH) 3.66–3.73, (m, 1H, CH), 6.87–7.35 (m, 3H, ArH). MS m/z 216 (M+H).

(f) N-[2-(3,4-Difluorophenyl)-4-hydroxybutyl]-N-methyl-3-nitro-1-naphthamide.

To a stirred cooled (0° C.) mixture of 3-(3,4-difluorophenyl)-N-methyl-4-amino-1-butanol (0.781 g, 3.63 mmol) in DCM (30 mL) and 1N NaOH (4.53 mL) was added dropwise a solution of 3-nitro-1-naphthoyl chloride (Example 3) (0.855 g, 3.63 mmol) in DCM (12 mL). The mixture was stirred at 0° C. for 2.5 h, water was added and the mixture was extracted with DCM. The combined organic layers were dried (MgSO$_4$), filtered, and concentrated in vacuo. Purification by chromatography (0%, 50%, 100% EtOAc in Et$_2$O) provided the title compound (1.25 g, 83%) as a light yellow solid. MS m/z 415 (M+H).

(g) N-[2-(3,4-Difluorophenyl)-4-oxobutyl]-N-methyl-3-nitro-1-naphthamide.

To a stirred cooled (−78° C.) solution of oxalyl chloride (0.39 mL, 4.52 mmol) in DCM (10 mL) was added DMSO (0.64 mL, 9.05 mmol) in DCM (5 mL). The solution was stirred at −78° C. for 5 min and a solution of N-[2-(3,4-difluorophenyl)-4-hydroxybutyl]-N-methyl-3-nitro-1-naphthamide (1.25 g, 3.02 mmol) in DCM (6 mL) and DMSO (3.4 mL) was added dropwise. The solution was stirred at −78° C. for 15 min and triethylamine (2.52 mL, 18.1 mmol) was added. Stirring was continued at −78° C. for 30 min and then at room temperature for 2 h. DCM (75 mL) and 1N HCl (75 mL) were added, the layers separated, and the organic layer was dried (MgSO$_4$), filtered, and concentrated in vacuo. Purification by chromatography (silica gel; 50% Et$_2$O in DCM (v/v)) provided the desired compound (1.15 g, 93%) as a light yellow solid. MS m/z 413 (M+H).

Example 14

N-[(S)-2-(3,4-Dichlorophenyl)-4-[4-[(S)-2-methylsulfinylphenyl]-1-piperidinyl]butyl]-N-methyl-3-nitro-1-naphthamide Citrate Hydrate (1:1:0.75)

To a stirred solution of 3-nitro-1-naphthoic acid (Kice, J L; Lotey H; J. Org. Chem., 54, 3596 (1989)) (0.36 g 1.66 mmol) in DCM (2 mL) was added oxalyl chloride (0.26 g, 2.06 mmol) dropwise via syringe. DMF (5 μL) was added and the solution was stirred overnight at room temperature. DCM was removed in vacuo, toluene (2 mL) was added and also removed in vacuo. The residue was dried under high vacuum for 2 h and used without further purification. Using standard acylation conditions 3-nitro-1-naphthoyl chloride was reacted with N-[(S)-2-(3,4-dichlorophenyl)-4-[4-[(S)-2-methylsulfinylphenyl]-1-piperidinyl]butyl]-N-methylamine and converted to the citrate salt. MS: 652 (M+H); analysis for C$_{34}$H$_{35}$C$_{12}$N$_3$O$_4$SC$_6$H$_8$O$_7$0.75.H$_2$O: calculated: C, 56.87; H, 5.13; N, 4.97; found: C, 56.01; H, 5.17; N, 4.80. The title compound was also converted to the citrate hydrate etherate (1.0:1.0:0.5:0.15).

Example 15

N-[(S)-2-(3,4-Dichlorophenyl)-4-[4-[(S)-2-methylsulfinylphenyl]-1-piperidinyl]butyl]-N-methyl-6-nitro-1-naphthamide Citrate A solution of 6-nitro-1-naphthoic acid (0.2 g, 0.922 mmol) (Dewar, M J S and Grisdale, P J; J. Amer Chem. Soc., 84, 3541 (1962)) in thionyl chloride (2 mL) was heated under reflux for 3 h. The solution was concentrated in vacuo then residual solvent was coevaporated twice with toluene to yield the acid chloride (0.217 g, quantitative) as a off white solid which was used without further purification. Using standard acylation conditions 6-nitro-1-naphthoyl chloride was reacted with N-[(S)-2-(3,4-dichlorophenyl)-4-[4-[(S)-2-methylsulfinylphenyl]-1-piperidinyl]butyl]-N-methylamine, converted to the citrate salt, and isolated by filtration from $Et_2O$ MS m/z 652 (M+H); analysis for $C_{34}H_{35}Cl_2N_3O_4S \cdot C_6H_8O_7 \cdot H_2O$: calculated: C, 55.68; H, 5.26; N, 4.87; found: C, 55.78; H, 5.20; N, 4.75.

Example 16

N-[2-(S)-(3,4-Dichlorophenyl)-4-[4-[(S)-2-methylsulfinylphenyl]-1-piperidinylpiperidinyl]butyl]-N-methyl-3-methylsulfonyl-1-naphthamide Using standard acylation conditions 0.450 g of N-[(S)-2-(3,4-dichlorophenyl)-4-[4-[(S)-2-methylsulfinylphenyl]-1-piperidinylpiperidinyl]butyl]-N-methylamine (Example 1, sub-part (b)) was reacted with 0.234 g of 3-methylsulfinyl-1-naphthoyl chloride and the resulting product was converted to the hydrochloride salt. The requisite acid chloride was prepared from the corresponding acid using oxalyl chloride; under these conditions the sulfoxide was oxidized to the sulfone. $^1H$ NMR (DMSO-$d_6$) 1.9 (m, 2H), 2.75 (s, 3H), 3.2 (m, 3H), 3.4 (s, 3H), 7.0–8.0 (m, 11H), 8.3 (m, 1H), 8.6 (s, 1H); MS m/z 685 (M+H); mp 175–180° C.

The requisite 3-methylsulfinyl-1-naphthoic acid was prepared as follows.

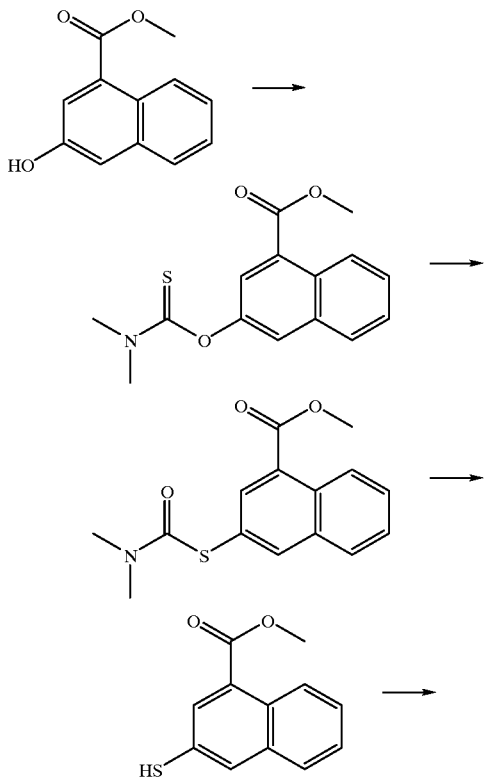

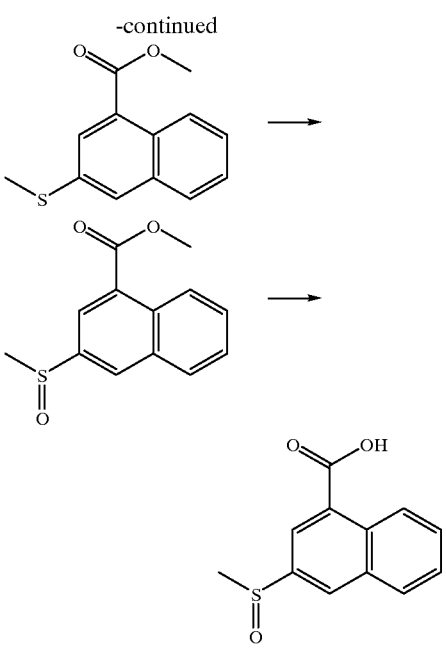

(a) Methyl 3-N,N-dimethylthiocarbamoyloxy-1-naphthoate.

A solution of 3-hydroxy-1-naphthoate in DMF (100 mL) was treated with 1,4-diazabicyclo[2,2,2]octane (2.24 g) and N,N-dimethylthiocarbomoyl chloride (2.48 g). After stirring for 16 h at ambient temperature the mixture was poured into ice cold water (200 mL), stirred for 4 h, and filtered to collect the solid which was washed with water and dried to afford titled material. $^1H$ NMR (CDCl$_3$) δ 3.4 (s, 3H), 3.5 (s, 3H), 3.96 (s, 3H), 7.6 (m, 2H), 7.7 (d, J=5, 1H), 7.8 (m, 1H), 8.0 (d, J=5, 1H), 9.0 (d, J=15, 1H), MS m/z 258 (M-OCH$_3$).

(b) Methyl 3-(N,N-dimethylcarbamoylthio)-1-naphthoate.

A solution of methyl 3-N,N-dimethylthiocarbamoyloxy)-1-naphthoate in N,N-dimethylaniline (30 mL) was heated under reflux for 20 h, cooled, and poured into concentrated hydrochloric acid containing ice. The solid precipitate was collected by filtration, washed with water, and dried to obtain the titled material. $^1H$ NMR (CDCl$_3$) δ 3.0 (s, 3H), 3.2 (s, 3H), 4.0 (s, 3H), 7.6 (m, 1H), 7.7 (m, 1H), 7.8 (d, J=10, 1H), 8.2 (s, 1H), 8.3 (d, J=2, 1H), 9.0 (d, J=10, 1H); MS m/z 258 (M-OMe).

(c) 3-Thio-1-naphthoic acid.

A solution of 0.91 g of methyl 3-N,N-dimethylcarbamoylthio-1-naphthoate in methanol was treated with 1.3 g of potassium hydroxide and the reaction mixture was heated under reflux for 1 h. The mixture was concentrated, dissolved in water and extracted with Et$_2$O. The aqueous layer was acidified with hydrochloric acid and the resulting precipitate was filtered and dried to afford 0.56 g of the titled product.

(d) Methyl 3-thiomethyl-1-naphthoate.

A solution of 3-thio-1-naphthoic acid in DMF was treated with 1.36 g of potassium carbonate followed by 0.62 mL of methyl iodide and heated to 80° C. for 4 h. The mixture was diluted with water and extracted with EtOAc. The organic layer was washed with water, dried, concentrated, and purified by chromatography. Elution with 9:1 hexane:EtOAc afforded 0.545 g of the titled product. $^1H$ NMR (CDCl$_3$) δ 2.6 (s, 3H), 4.0 (s, 3H), 7.5 (m, 2H), 7.8 (m, 2H), 8.1 (s, 1H), 8.8 (m, 1H); MS m/z 233.

(e) Methyl 3-methylsulfinyl-1-naphthoate.

A solution of methyl 3-thiomethyl-1-naphthoate in THF was treated with sodium periodate dissolved in 10 mL of water. After stirring for 1 h the mixture was concentrated, diluted with water, and extracted with EtOAc. The organic layer was dried and concentrated under reduced pressure to afford the titled product. $^1$H NMR (CDCl$_3$) δ 2.9 (s, 3H), 4.0 (s, 3H), 7.7 (m, 2H), 8.0 (d, J=15, 1H), 8.3 (d, J=5, 1H), 8.4 (s, 1H), 9.0 (d, J=15, 1H); MS m/z 249 (M+H).

(f) 3-Methylsulfinyl-1-naphthoic acid.

Methyl 3-methylsulfinyl-1-naphthoate was converted to the desired material by heating a solution of the material in methanol (10 mL) and 1N sodium hydroxide (2 mL) under reflux for 1 h. The reaction mixture was acidified with 5% HCl, extracted with ethyl acetate and the organic layer was dried over magnesium sulfate and concentrated under reduced pressure. $^1$H NMR (CDCl$_3$) δ 3.15 (s, 3H), 7.6 (m, 2H), 8.05 (m, 1H), 8.6 (s, 1H), 9.1 (m, 1H); MS m/z 235 (M+H).

Example 17

N-[2-(3,4-Difluorophenyl)-4-[4-(S)-2-(methylsulfinyl)-phenyl]-1-piperidinyl]-butyl]-N-methyl-3-cyano-1-naphthamide Citrate Using standard reductive amination conditions N-[2-(3,4-difluorophenyl)-4-oxobutyl]-N-methyl-3-cyano-1-naphthamide (0.255 g, 0.65 mmol) was reacted with 4-[(S)-2-methylsulfinyl-phenyl]-piperidine (Shenvi, A B; Jacobs, R T; Miller, S C; Ohnmacht, C J, Jr., Veale, C A., WO 9516682) (0.155 g, 0.65 mmol) and converted to the citrate salt (white solid. 0.25 g, 64%). MS m/z 600 (M+H); analysis for $C_{35}H_{35}F_2N_3O_2S.1.0\ C_6H_8O_7.1.5\ H_2O$: calculated: C, 60.13; H, 5.66; N, 5.13; found: C, 60.16; H, 5.60; N, 5.05.

The required N-[2-(3,4-difluorophenyl)-4-oxobutyl]-N-methyl-3-cyano-1-naphthamide was prepared as follows.

(a) N-[2-(3,4-Difluorophenyl)-4-hydroxybutyl]-N-methyl-3-cyano-1-naphthalenecarboxamide.

To a stirred cooled (0° C.) mixture of 3-(3,4-difluorophenyl)-N-methyl-4-amino-1-butanol (Example 13 subpart (e)) (0.48 g, 2.23 mmol), 14 mL DCM and 10% aqueous NaOH (2.80 mL) was added via cannula a solution of 3-cyano-1-naphthoyl chloride in 10 mL DCM and the mixture stirred overnight while warming to ambient temperature. The reaction was poured into a mixture of water and DCM, the organic phase was collected, washed twice and dried (Na$_2$SO$_4$). The product was purified by chromatography (30% ether in hexane and 50% ether in hexane) to yield the title compound as a white solid (0.65 g, 74%). MS m/z 395 (M+H); $^1$H NMR (CDCl$_3$) δ 1.93–2.06 (m, 1H), 2.61 (s, 3H), 3.17–3.74 (m, 6H), 7.17–7.90 (m, 8H), 8.21 (s, 1H).

(b) N-[2-(3,4-Difluorophenyl)-4-oxobutyl]-N-methyl-3-cyano-1-naphthamide.

To a stirred cooled (−78° C.) solution of oxalyl chloride (0.22 mL, 2.47 mmol) and DCM (8.0 mL) was added via cannula a solution of DMSO (0.35 mL, 4.93 mmol) and DCM (5 mL), and the mixture stirred for 5 min. A solution of N-[2-(3,4-difluorophenyl)-4-hydroxybutyl]-N-methyl-3-cyano-1-naphthalenecarboxamide (0.65 g, 1.65 mmol), DCM (8.0 mL) and DMSO (1.9 mL) was added slowly via cannula followed after 5 min by triethylamine (1.38 mL, 9.87 mmol.). After an additional 15 min the ice bath was removed and reaction stirred at ambient temperature overnight. Purification by chromatography (1:1 hexane in ether) provided the desired compound as a white solid (0.516 g, 80%). MS m/z 393 (M+H); $^1$H NMR (CDCl$_3$) δ 2.68 (s, 3H), 2.95 (t, 2H), 3.24–3.31 (d, 1H), 3.60–3.83 (m, 2H), 7.22–7.91 (m, 8H), 8.22 (s, 1H), 9.80 (s, 1H).

Example 18

N-[(S)-2-(3,4-Dichlorophenyl)-4-[4-[2-(methylsulfonyl)phenyl]-1-piperidinyl]butyl]-N-methyl-3-cyano-1-naphthamide Citrate Using standard reductive amination conditions 4-(2-methylsulfonylphenyl)piperidine (Shenvi, A B; Jacobs, R T; Miller, S C; Ohnmacht, C A; Veale, C A. WO 9516682) was reacted with N-[2-(S)-(3,4-dichlorophenyl)-4-oxobutyl]-N-methyl-3-cyano-1-naphthamide. The product was converted to the citrate salt. MS m/z 648 (M+H); analysis for $C_{35}H_{35}Cl_2N_3O_3S.C_6H_8O_7$: calculated: C, 58.57; H, 5.15; N, 5.00. found: C, 58.92; H, 5.31; N, 5.01.

Example 19

N-[(S)-2-(3,4-Dichlorophenyl)-4-[4-[2-oxoethylphenyl]-1-piperidinyl]butyl]-N-methyl-3-cyano-1-naphthamide Citrate A solution of 4-(2-oxoethylphenyl)-piperidine-N-Boc-amine was stirred in a solution of DCM (3 mL) and trifluoroacetic acid (1 mL) for 1 h, concentrated under reduced pressure, residual solvent was coevaporated twice from methanol, and dried under high vacuum to provide the N-deprotected 4-(2-acetylphenyl)piperidine. Using standard reductive amination conditions 4-(2-acetylphenyl)piperidine was reacted with N-[2-(S)-(3,4-dichlorophenyl)-4-oxobutyl]-N-methyl-3-cyano-1-naphthamide and converted to the citrate salt. MS m/z 612 (M+H).

4-(2-Oxoethylphenyl)-piperidine-N-Boc-amine was prepared as follows.

(a) 4-(2-Oxoethylphenyl)-1,2,5,6-tetrahydropyridine-N-Boc-amine.

Based on the procedure of Laborde, E; Kiely, J S; Lesheski, L E; Schroeder, M C; J. Het. Chem.; 28, 191, (1991), a solution of 4-(tributylstannyl)-1,2,5,6-tetrahydropyridine-N-Boc-amine (2.0 g, 4.04 mmol), 2'-bromoacetophenone (653 μL, 4.85 mmol), and tetrakis (triphenylphosphine) palladium (480 mg) was stirred at 100° C. in toluene (35 mL). After 3 h, a second portion of tetrakis(triphenylphosphine) palladium (450 mg) was added. After a total of 7 h the reaction mixture was allowed to cool and stirring was continued overnight. The reaction mixture was concentrated and partially purified by chromatography (10–30% EtOAc in hexanes) (774 mg, 2.57 mmol, 64%). To remove trace tin-containing impurities, the material was further purified by preparative HPLC (C18, 10–100% CH$_3$CN in water with 0.1% TFA). MS m/z 324 (M+Na). $^1$H NMR (CDCl$_3$) δ 7.56 (d, J=7.5, 1H), 7.45 (t, J=7.5, 1H), 7.35 (t, J=7.5, 1H), 7.22 (t, J=7.5, 1H), 5.54 (br s, 1H), 4.02 (d, J=2.7, 2H), 3.66 (t, J=5.7, 2H), 2.48 (s, 3H), 2.40 (br s, 2H), 1.50 (s, 9H).

(b) 4-(2-Oxoethylphenyl)-piperidine-N-Boc-amine.

A mixture of 4-(2-acetylphenyl)-1,2,5,6-tetrahydropyridine-N-Boc-amine (475 mg, 1.57 mmol) and 10% Pd/C (150 mg) was stirred in methanol (30 mL) under hydrogen (1 atm) for 16 h, filtered through Celite, washed with DCM, and concentrated to afford the product as a yellow oil (397 mg, 1.31 mmol, 83%). MS m/z 204 (M-Boc).

Example 20

N-[(S)-2-(3,4-Dichlorophenyl)-4-[4-[2-methoxycarbonylphenyl]-1-piperidinyl]butyl]-N-methyl-3-cyanonaphthamide Citrate N-[(S)-2-(3,4-Dichlorophenyl)-4-[4-[2-methoxycarbonylphenyl]-1-piperidinyl]butyl]-N-methylamine hydrochloride (0.155 g) was dissolved in DCM (10 mL), triethylamine (0.061 g) was added followed by 3-cyano-1-naphthoyl chloride (0.069 g). The mixture was stirred overnight, diluted with saturated sodium bicarbonate and extracted with EtOAc. The organic phase was dried and evaporated. The residue was purified by chromatography with DCM:methanol (30:1) as the eluent to give the free base (0.170 g) which was converted to the citrate salt. MS: m/z 658 (M+H). $^1$H NMR (DMSO d$_6$) δ 8.80–6.70 (m, 13H), 3.84 (s, 3H, OCH$_3$), 2.55 (m, 3H, N—CH$_3$).

The requisite amine was prepared as follows.

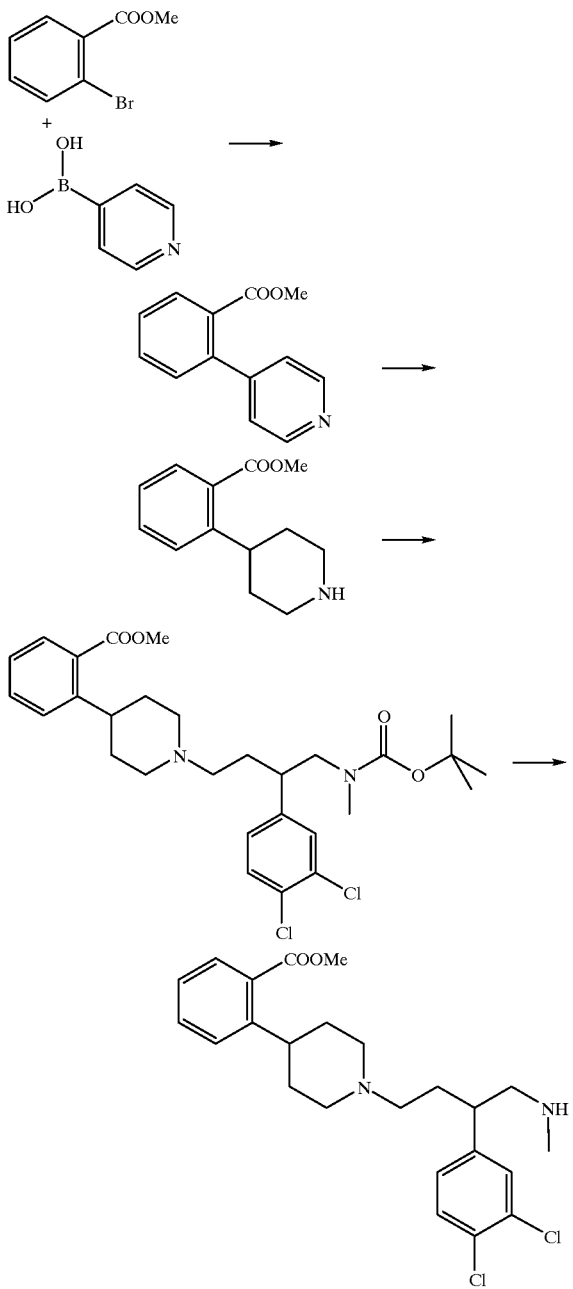

(a) 4-(2-Methoxycarbonylphenyl)pyridine hydrochloride.

Methyl 2-bromobenzoate (1.400 g) and tetrakis (triphenylphosphine) palladium(0) (0.225 g) were combined in dry 1,2-dimethoxyethane (50 mL) under nitrogen. The mixture was stirred for 20 minutes then pyridine-4-boronic acid (0.800 g) (prepared according to the method described by Lamothe, M; Pauwels, P J; Belliard, K; Schambel, P; and Halazy, S; J. Med. Chem., 40, 3542 (1997)) was added followed immediately by a solution of sodium carbonate (1.610 g) in water (15 mL). The mixture was heated under reflux for 5 h, then extracted with EtOAc. The organic extracts were dried, evaporated, and the residue was purified by chromatography with DCM:methanol (20:1) as the eluent to give the pyridine free base. The free base was dissolved in DCM and treated with an excess of ethereal hydrogen chloride to provide the title compound (0.900 g) as a white solid. MS: m/z 214 (M+H). $^1$H NMR (CDCl$_3$) δ 8.63 (d, 2H), 7.93 (m, 1H), 7.55 (m, 3h), 7.30 (m, 2H), 3.67 (s, 3H).

(b) 4-(2-Methoxycarbonylphenyl)piperidine hydrochloride.

4-(2-Methoxycarbonylphenyl)pyridine hydrochloride (0.595 g) was dissolved in acetic acid (30 mL), platinum dioxide (0.240 g) was added and the mixture shaken under hydrogen (50 psi) for 3 h. The solution was filtered, acidified with 4M HCl and evaporated to provide the piperidine hydrochloride (0.243 g) as a white solid. MS: m/z 220 (M+H).

(c) N-[(S)-2-(3,4-Dichlorophenyl)-4-[4-[2-methoxycarbonylphenyl]-1-piperidinyl]butyl]-N-methyl-N-Boc-amine.

N-[(S)-2-(3,4-Dichlorophenyl)-4-oxobutyl]-N-methyl-N-Boc-amine (0.261 g) (Miller, S C; WO 9505377) was added to a solution of 4-(2-methoxycarbonylphenyl)piperidine hydrochloride (0.600 g) and triethylamine (0.282 g) in methanol (30 mL). The mixture was stirred for 5 minutes then a methanol (3 mL) solution of sodium cyanoborohydride (0.250 g) was added. The reaction was stirred overnight at ambient temperature. Methanol was evaporated and the residue partitioned between EtOAc (20 mL) and aqueous sodium bicarbonate (10 mL). The organic phase was dried and evaporated. The residue was purified by chromatography, with EtOAc as the eluent, to give the desired compound (0.600 g). MS: m/z 549 (M+H). $^1$H NMR (CDCl$_3$) δ 7.81–7.05 (m, 7H), 3.88 (s, 3H), 3.60–1.85 (m, 19H), 1.41 (s, 9H).

(d) N-[(S)-2-(3,4-Dichlorophenyl)-4-[4-[2-methoxycarbonylphenyl)]-1-piperidinyl]butyl]-N-methylamine hydrochloride.

N-[(S)-2-(3,4-Dichlorophenyl)-4-[4-[2-carboxymethylphenyl]-1-piperidinyl]butyl]-N-methyl-N-Boc-amine (0.085 g) was dissolved in EtOAc (5 mL), cooled to 0° C. and hydrogen chloride was bubbled through the solution for 5 min. The solution was stirred an additional 5 min then evaporated and used directly in the subsequent reaction.

Example 21

N-[2-(S)-(3,4-Dichlorophenyl)-4-[4-[2-methylsulfonylaminophenyl]-1-piperidinyl]butyl]-N-methyl-3-cyano-1-naphthamide Citrate 4-(2-Methylsulfonylaminophenyl)piperidine hydrochloride (0.076 g) was reacted with N-[2-(S)-(3,4-dichlorophenyl)-4-oxobutyl]-N-methyl-3-cyano-1-naphthalenecarboxamide (0.123 g) using the method described in Example 20, subpart c. The product was converted to the citrate salt to give the title compound (0.122 g) as a white solid. MS m/z 663 (M+H). $^1$H NMR (DMSO-d$_6$) δ 9.14 (m, 1H), 8.62 (m, 1H), 8.05 (m, 1H), 7.95–6.90 (m, 10H), 3.17 (s, 3H, S, CH$_3$), 2.97 (s, 3H, N—CH$_3$).

The requisite amine was prepared as follows.

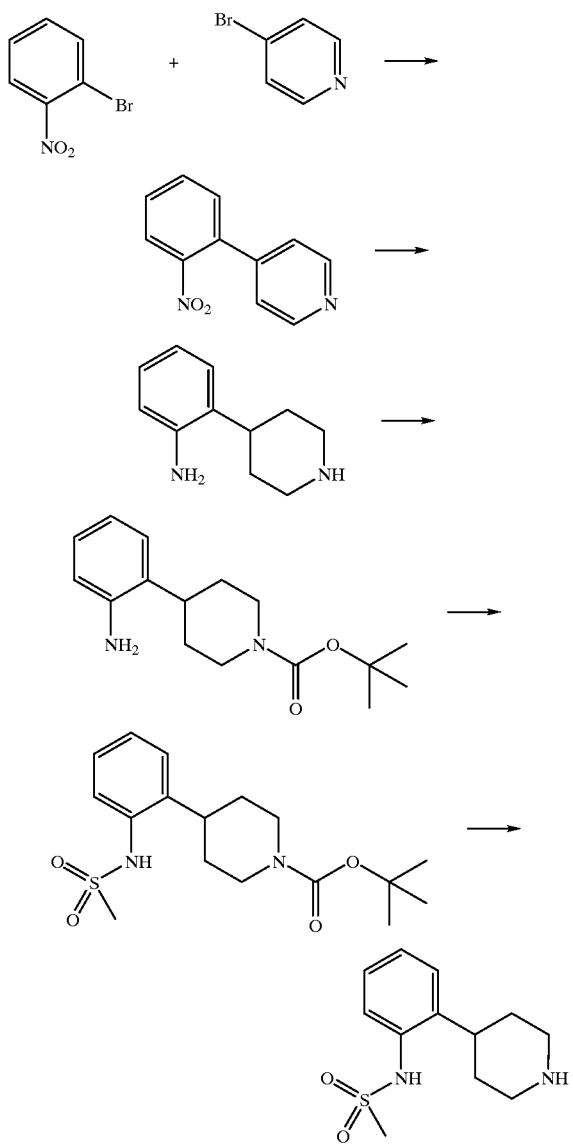

(a) 4-(2-Aminophenyl)piperidine.

Following Ullmann coupling of 2-nitrobromobenzene and 4-bromopyridine (Shimizu, N.; Kitamura, T.; Watanabe, K; Yamaguchi, T.; Shigyo, H.; Ohta, T.; Tetrahedron Lett. 34, 3421 (1993), the title compound was prepared by hydrogenation of 4-(2-nitrophenyl)pyridine using the general method described in Example 20 sub-part (b). MS m/z 177 (M+H).

(b) 4-(2-Aminophenyl)-N-Boc-piperidine.

A solution of 4-(2-aminophenyl)piperidine (4.04 g) in water (200 mL) was adjusted to pH 9 by addition of potassium carbonate and cooled in an ice-water bath. A solution of di-tert-butyl dicarbonate (5.20 g) in 1,4-dioxane (80 mL) was added dropwise. The stirred mixture was allowed to warm gradually to room temperature over 3 h. Additional potassium carbonate was added as necessary to maintain pH 9. The reaction was extracted with $Et_2O$.

The organic extracts were dried and evaporated. The residue was purified by chromatography, with 3:1 hexanes:EtOAc as the eluent, to give the title compound (3.26 g). MS m/z 177 (M-Boc), 299 (M+Na). $^1$H NMR (DMSO-$d_6$) δ 6.87 (m, 2H), 6.65 (d, 1H), 6.52 (m, 1H), 4.91 (s, 2H, NH2), 4.04 (m, 2H), 2.76 (m, 3H), 1.70 (m, 2H), 1.42 (s, 9H), 1.34 (m, 2H).

(c) 4-(2-Methylsulfonylaminophenyl)-N-Boc-piperidine.

Methanesulfonyl chloride (0.035 g) was added to a solution of 4-(2-aminophenyl)-N-Boc-piperidine (0.070 g) and pyridine (0.027 g) in DCM (3 mL) and stirred overnight. The reaction was diluted with aqueous sodium bicarbonate and extracted with EtOAc. The organic extracts were dried and evaporated to give the title compound (0.093 g) as a colorless oil. MS m/z 255 (M-Boc), 377 (M+Na).

(d) 4-(2-Methylsulfonylaminophenyl)piperidine hydrochloride.

A solution of 4-(2-methylsulfonamidophenyl)-N-Boc-piperidine (0.093 g) was dissolved in EtOAc (5 mL) and cooled in an ice-water bath. Hydrogen chloride was bubbled through the solution for 5 min and stirring continued for an additional 5 min, then evaporated to give the desired compound (0.076 g) as a white solid. MS m/z 255 (M+H). $^1$H NMR (DMSO-$d_6$) δ 7.30 (m, 4H), 3.29 (m, 5H), 2.99 (s, 3H, S—$CH_3$), 1.82 (m, 4H).

Example 22

N-[2-(S)-(3,4-Dichlorophenyl)-4-(4-[2-acetamidophenyl]-1-piperidinyl)butyl]-N-methyl-3-cyano-1-naphthamide Citrate 4-(2-Acetamidophenyl)-piperidine hydrochloride (0.070 g) was reacted with N-[2-(S)-(3,4-dichlorophenyl)-4-oxobutyl]-N-methyl-3-cyano-1-naphthamide (0.130 g) using the method described in Example 20 sub-part c. The product was converted to the citrate salt to give the title compound (0.102 g) as a white solid. MS m/z 627 (M+H). $^1$H NMR (DMSO-$d_6$) δ 8.0 (m, 1H), 8.6 (m, 1H), 8.1 (m, 1H), 7.90–6.80 (m, 10H), 2.60 (s, 3H, N—$CH_3$), 2.04 (s, 3H, CO—$CH_3$).

The requisite amine was prepared as follows.

(a) 4-(2-Acetamidophenyl)-N-Boc-piperidine.

Acetyl chloride (0.060 g) was added to a solution of 4-(2-aminophenyl)-N-Boc-piperidine (0.070 g) (Example 21 sub-part (b)) and triethylamine (0.090 g) in DCM (2 mL) and stirred overnight. The reaction was diluted with $Et_2O$ and extracted sequentially with aqueous sodium bicarbonate and 1N HCl. The organic extract was dried and evaporated to give the title compound (0.070 g) as a colorless oil. MS m/z 341 (M+Na). $^1$H NMR ($CDCl_3$) δ 7.26 (m, 4H), 7.69 (br, 1H), 4.15 (m, 2H), 2.67 (m, 3H), 2.23 (s, 3H), 1.75 (m, 4H), 1.48 (s, 9H).

(b) 4-(2-Acetamidophenyl)piperidine hydrochloride.

4-(2-Acetamidophenyl)-N-Boc-piperidine (0.070 g) was deprotected using the method described in Example 21 sub-part (d) to give the desired compound (0.057 g). MS m/z 627 (M+H); $^1$H NMR (DMSO-$d_6$) δ 9.47 (s, 1H), 8.80 (br, 2H), 7.22 (m, 4H), 3.35 (m, 2H), 2.95 (m, 3H), 2.07 (s, 3H), 1.82 (m, 4H).

Example 23

N-[2-(S)-(3,4-Dichlorophenyl)-4-(4-[2-(1-pyrrolidine-2,5-dione)phenyl]-1-piperidinyl)-butyl]-N-methyl-3-cyano-1-naphthamide Citrate 4-[2-(1-Pyrrolidine-2,5-dione)phenyl]piperidine hydrochloride (0.073 g) was reacted with N-[2-(S)-(3,4-dichlorophenyl)-4-oxobutyl]-N-methyl-3-cyano-1-naphthanide (0.116 g) using the method described in Example 20 sub-part c. The product was converted to the citrate salt to give the title compound (0.081 g) as a white solid. MS m/z 667 (M+H); $^1$H NMR (DMSO-d$_6$) δ 9.51 (br, 1H), 8.63 (br, 1H), 8.09 (m, 1H), 7.9–7.0 (m, 10H), 2.61 (m, 3H, N—CH$_3$).

The requisite 4-[2-(1-pyrrolidine-2,5-dione)phenyl] piperidine was prepared as follows.
(a) 4-(2-(1-Pyrrolidine-2,5-dione)phenyl)-N-Boc-piperidine.

Succinic anhydride (0.032 g) and 4-(2-aminophenyl)-N-Boc-piperidine (0.070 g) (Example 21, sub-part (b)) were combined in m-xylene containing a catalytic amount of triethylamine and heated under reflux overnight. The reaction was diluted with aqueous sodium bicarbonate and extracted with EtOAc. The organic extracts were dried and evaporated to give the title compound (0.080 g) as a white solid. MS m/z 259 (M-Boc).
b) 4-(2-(1-Pyrrolidine-2,5-dione)phenyl)piperidine.

4-(2-(1-Pyrrolidine-2,5-dione)phenyl)-N-Boc-piperidine (0.080 g) was deprotected using the method described in Example 21 subpart (d) to give the desired compound (0.061 g) as a white solid. MS m/z 259 (M+H); $^1$H NMR (DMSO-d$_6$) δ 7.50 (m, 1H), 7.37 (m, 2H), 7.14 (m, 1H), 3.32 (m, 2H), 2.83 (m, 6H), 1.85 (m, 3H), 1.68 (m, 2H).

Example 24

N-[2-(S)-(3,4-Dichlorophenyl)-4-(4-[2-{3-Methylureido}phenyl]-1-piperidinyl)butyl]-N-methyl-3-cyano-1-naphthamide Citrate 4-[2-{3-Methylureido}phenyl]piperidine hydrochloride (0.052 g) was reacted with N-[2-(S)-(3,4-dichlorophenyl)-4-oxobutyl]-N-methyl-3-cyano-1-naphthamide (0.100 g) using the method described in Example 20 sub-part c. The product was converted to the citrate salt to give the title compound (0.125 g) as a white solid. MS m/z 642 (M+H); $^1$H NMR (DMSO-d$_6$) δ 8.63 (br, 1H), 8.08 (m, 1H), 7.95–6.90 (m, 11H), 6.19 (br, 1H), 2.65 (m, 3H).

The requisite amine was prepared as follows.
(a) 4-[2-(3-Methylureido)phenyl]-N-Boc-piperidine.

Triphosgene (0.062 g) was added to a solution of 4-(2-aminophenyl)-N-Boc-piperidine (0.055 g) (Example 21 sub-part (b)) in DCM (5 mL). Triethylamine (0.025 g) was added rapidly with vigorous stirring. After 15 min 2M methylamine in THF (2 mL) was added and the mixture stirred for 1 h. The reaction was diluted with 1N HCl and extracted with DCM.

The organic extracts were dried and evaporated to give the title compound (0.076 g) as a colorless oil. MS m/z 234 (M-Boc); $^1$H NMR (CDCl$_3$) δ 7.28 (m, 5H), 6.00 (s, 1H), 4.44 (m, 1H), 4.23 (br, 2H), 3.75 (m, 1H), 3.00 (m, 1H), 2.81 (d, 3H), 1.85 (m, 1H), 1.69 (m, 3H), 1.48 (s, 9H).
(b) 4-[2-(3-Methylureido)phenyl]piperidine hydrochloride.

4-[3-Methylureidophenyl]-N-Boc-piperidine (0.074 g) was deprotected using the method described in Example 21 sub-part (d) to give the desired compound (0.052 g) as a waxy solid. MS m/z 234 (M+H).

Example 25

N-[2-(S)-(3,4-Dichlorophenyl)-4-(4-[2-{3-dimethylureido}phenyl]-1-piperidinyl)butyl]-N-methyl-3-cyano-1-naphthamide Citrate This compound was prepared according to the method described in Example 24 substituting dimethylamine for methylamine in sub-part (a). MS m/z 656 (M+H). $^1$H NMR (DMSO-d$_6$) δ 8.63 (br, 1H), 8.08 (m, 1H), 7.95–6.90 (m, 11H), 2.91 (s, 6H), 2.60 (s, 3H).

Example 26

N-[2-(S)-(3,4-Dichlorophenyl)-4-(4-[2-dimethylaminophenyl]-1-piperidinyl)butyl]-N-methyl-3-cyano-1-naphthamide Citrate 4-(2-Dimethylaminophenyl)piperidine dihydrochloride (0.063 g) was reacted with N-[2-(S)-(3,4-dichlorophenyl)-4-oxobutyl]-N-methyl-3-cyano-1-naphthamide (0.100 g) using the method described in Example 20 sub-part c. The product was converted to the citrate salt to give the title compound (0.105 g) as a white solid. MS m/z 613 (M+H). $^1$H NMR (DMSO-d$_6$) δ 8.63 (s, 1H), 8.06 (m, 1H), 7.95–7.0 (m, 11H), 2.59 (s, 6H), 2.55 (m, 3H).

The requisite amine was prepared as follows.
(a) 4-(2-Dimethylaminophenyl)-N-Boc-piperidine.

Formaldehyde (37 wt. % in water, 0.50 mL) was added to a solution of 4-(2-amino-phenyl)-N-Boc-piperidine (0.065 g) (Example 21 sub-part (b)) and acetic acid (10 µL) in methanol (2 mL). The mixture was stirred for 5 min. A solution of sodium cyanoborohydride (0.100 g) in methanol (2 mL) was added and the mixture stirred overnight. The reaction was concentrated, the residue mixed with aqueous sodium bicarbonate and extracted with Et$_2$O.

The organic extracts were dried and concentrated to give the title compound (0.071 g) as a waxy solid. MS m/z 305 (M+H).
(b) 4-(2-Dimethylaminophenyl)piperidine dihydrochloride.

4-(2-Dimethylaminophenyl)-N-Boc-piperidine (0.070 g) was deprotected using the method described in (Example 21 sub-part (d)) to give the title compound (0.063 g) as a waxy solid. MS m/z 205 (M+H).

Example 27

N-[2-(S)-(3,4-Dichlorophenyl)-4-[4-[2-trifluoromethylsulfinylphenyl]-1-piperidinyl]-butyl]-N-methyl-3-cyano-1-naphthamide Citrate Using standard reductive amination conditions N-[2-(S)-(3,4-dichlorophenyl)-4-oxobutyl]-N-methyl-3-cyano-1-naphthamide was reacted with 4-[2-trifluoromethylsulfinylphenyl]piperidine and converted to the citrate salt. $^1$H NMR (DMSO-d$_6$) δ 8.62 (d, 1H), 8.08 (br m, 1H), 7.92 (m, 1H), 7.65–6.41 (m, 10H), 4.54 (m, 1H), 4.11–1.60 (18H); MS m/z 686 (M+H).

The requisite 4-[2-trifluoromethylsulfinylphenyl] piperidine was prepared as follows.
(a) N-Phenylmethoxycarbonyl-4-[2-thiophenyl]piperidine.

Based on the procedure by Young, R N; Gauthier, J Y; Coombs, W; Tetrahedron Lett., 25, 1753, (1984) a solution of N-phenylmethoxycarbonyl-4-(2-methylsulfinylphenyl) piperidine (2.80 mmol) in trifluoroacetic anhydride (50 mL) was heated under reflux at 40° C. for 1 h. The mixture was concentrated and the residue stirred with a 1:1 mixture of methanol:triethylamine (50 mL) for 15 min. The mixture was concentrated again and purified by chromatography (15% EtOAc in hexane) to provide the product as a white precipitate (76%). $^1$H NMR (DMSO-d$_6$) δ 7.39 (m, 4H), 7.20 (d, 1H), 7.19 (d, 1H), 7.10 (m, 3H), 5.29 (s, 1H), 5.09 (s, 2H), 4.10 (br d, 2H), 2.89 (m, 3H), 1.77 (br d, 2H), 1.57 (m, 2H); MS m/z 326 (M–H).
(b) N-Phenylmethoxycarbonyl-4-(2-trifluoromethylthiophenyl)piperidine.

Based on the procedure by Koshechko, V G; Kiprianova, L A; Fileleeva. L I; Tetrahedron Lett, 33 6677 (1992) a 3-neck flask fitted with a jacketed dropping funnel and a dry-ice condenser under nitrogen was charged with DMF (9.5 mL) and triethylamine (0.5 mL). The solution was stirred at room temperature and purged with a stream of nitrogen for 20 min. Trifluoromethyliodide (0.6 mL) was condensed into the dropping funnel and N-phenylmethoxycarbonyl-4-(2-thiophenyl)piperidine (780 mg) was added to the stirring DMF solution followed by addition of methyl viologen dichloride hydrate (43 mg). Stirring was continued for 5 min then trifluoromethyliodide was rapidly added to the dark blue solution and the mixture was stirred for 1 h. The mixture was then poured into ice water and stirred until all bubbling ceased (20 min). The mixture was extracted into $Et_2O$, washed with brine, dried ($MgSO_4$), concentrated, and purified by chromatography (25% EtOAc in hexane) to afford the product (650 mg, 70%) as a colorless oil. $^1H$ NMR (DMSO-$d_6$) δ 7.95 (d, 1H), 7.55 (m, 3H), 7.36 (m, 5H), 5.10 (s, 2H), 4.16 (br d, 2H), 3.46 (m, 1H), 2.93 (br s, 2H), 1.53 (m, 4H); MS m/z 396 (M+H).

(c) N-Phenylmethoxycarbonyl-4-(2-trifluoromethylsulfinylphenyl)piperidine.

To a solution of N-phenylmethoxycarbonyl-4-(2-trifluoromethylthiophenyl)piperidine (650 mg) in DCM (20 mL) at 0° C. was added 3-chloroperoxybenzoic acid (0.57 g) in small portions. The ice bath was removed and stirring was continued overnight. The white slurry was diluted with saturated $NaHCO_3$ (10 mL) and water, extracted into DCM, washed with brine, dried ($MgSO_4$), concentrated, and purified by chromatography (25% EtOAc in hexane) to afford the product as a white solid (500 mg, 74%). $^1H$ NMR (DMSO-$d_6$) δ 8.12 (d, 1H), 7.62 (m, 3H), 7.37 (m, 5H), 5.10 (s, 2H), 4.14 (m, 2H), 3.12 (m, 3H), 1.79 (m, 4H); MS m/z 412 (M+H).

(d) 4-(2-Trifluoromethylsulfinylphenyl)piperidine.

A solution of N-phenylmethoxycarbonyl-4-[2-trifluoromethylsulfinylphenyl]piperidine (230 mg) was dissolved in trifluoroacetic acid (5 mL) and the mixture was heated under reflux at 80° C. for 10 min. The mixture was concentrated, neutralized by addition of 2N NaOH (5 mL), extracted into chloroform, dried ($MgSO_4$), concentrated, and purified by chromatography (15% methanol in DCM with 1% $NH_4OH$) to afford the product (100 mg, 65%). $^1H$ NMR (DMSO-$d_6$) δ 8.10 (d, 1H), 7.83 (m, 1H), 7.61 (m, 2H), 2.91 (m, 2H), 2.5 (m, 3H), 1.74 (m, 2H), 1.54 (m, 2H); MS m/z 278 (M+H).

Example 28

N-[2-(S)-(3,4-Dichlorophenyl)-4-[4-[2-trifluoromethylthiophenyl]-1-piperidinyl]butyl]-N-methyl-3-cyano-1-naphthamide Citrate Using standard reductive amination conditions N-[2-(S)-(3,4-dichlorophenyl)-4-oxobutyl]-N-methyl-3-cyano-1-naphthamide was reacted with 4-(2-trifluoromethylthiophenyl)piperidine except NaOAc (2.0 eq.) was added in place of acetic acid. The product was converted to the citrate salt. $^1H$ NMR (DMSO-$d_6$) δ 8.62 (d, 1H), 8.08 (m, 1H), 7.75 (m, 5H), 7.53–6.44(br m, 6H), 4.49 (m, 1H), 3.45–0.85 (18H); MS m/z 670 (M+H).

The requisite 4-(2-trifluoromethylthiophenyl)piperidine was prepared as follows.

4-(2-Trifluoromethylthiophenyl)piperidine.

A solution of N-phenylmethoxycarbonyl-4-[2-trifluoromethylthiophenyl]piperidine in trifluoroacetic acid was Cbz-deprotected by heating under reflux (at 80° C.) for 10 min. The mixture was concentrated to provide the product as an oil. $^1H$ NMR (DMSO-$d_6$) δ 7.69 (d, 1H), 7.59 (m, 1H), 7.50 (d, 1H), 7.32 (m, 1H), 3.32 (m, 2H), 3.00 (br d, 2H), 2.57 (m, 3H), 1.56 (m, 4H); MS m/z 262 (M+H).

Example 29

N-[2-(S)-(3,4-Dichlorophenyl)-4-[4-[2-ethylsulfinylphenyl]-1-piperidinyl]butyl]-N-methyl-3-cyano-1-naphthamide Citrate Using standard reductive amination conditions N-[2-(S)-(3,4-dichlorophenyl)-4-oxobutyl]-N-methyl-3-cyano-1-naphthamide was reacted with 4-[2-ethylsulfinylphenyl]piperidine and converted to the citrate salt. $^1H$ NMR (DMSO-$d_6$) δ 8.62 (d 1H), 8.08 (m, 1H), 7.73 (m, 5H), 7.53–6.43 (m, 6H), 4.54 (m, 1H), 3.34–1.78 (21H), 1.08 (t, 3H); MS m/z 646 (M+H).

The requisite 4-[2-ethylsulfinylphenyl]piperidine was prepared as follows.

(a) N-Phenylmethoxycarbonyl-4-(2-ethylthiophenyl)piperidine.

Iodoethane (0.24 mL) was added to a mixture of N-phenylmethoxycarbonyl-4-(2-thiophenyl)piperidine (Example 27) (1.0 g) and $K_2CO_3$ (0.42 g) in DMF (10 mL). After 2 hours the solution was diluted with water and extracted into EtOAc. The organic layer was washed with brine (3×), dried ($MgSO_4$), concentrated, and purified by chromatography (10% EtOAc/hexane as the eluent to give the product as an oil (1.04 g, 95%). $^1H$ NMR (DMSO-$d_6$) δ 7.37 (m, 5H), 7.19 (m, 4H), 5.09 (s, 2H), 4.13 (br d, 2H), 3.16 (m, 1H), 3.02 (m, 4H), 1.70 (br d, 2H), 1.54 (m, 2H), 1.24 (t, 3H); MS m/z 356 (M+H).

(b) N-Phenylmethoxycarbonyl-4-(2-ethylsulfinylphenyl)piperidine.

To a solution of N-phenylmethoxycarbonyl-4-(2-ethylthiophenyl)piperidine (1.04 g) in a 1:1 mixture of THF:methanol (30 mL) was added sodium periodate (1.88 g) and the mixture was allowed to stir overnight. The white slurry was diluted with $NaHCO_3$ and water. The mixture was extracted into DCM, washed with brine, dried ($MgSO_4$), concentrated, and purified by chromatography (25% EtOAc in hexane) as the eluent to give the product (1.0 g, 92%). $^1H$ NMR (DMSO-$d_6$) δ 7.55 (m, 1H), 7.48 (m, 3H), 7.35 (m, 5H), 5.15 (s, 2H), 4.11 (br d, 2H), 2.93 (m, 4H), 2.66 (m, 1H), 1.64 (m, 4H), 1.11 (t, 3H); MS m/z 372 (M+H).

(c) 4-[2-Ethylsulfinylphenyl]piperidine.

N-Phenylmethoxycarbonyl-4-[2-ethylsulfinylphenyl]piperidine was deprotected according to the method described for the deprotection of 4-[2-trifluoromethylsulfinylphenyl]piperidine (Example 27, step (d)). $^1H$ NMR (DMSO-$d_6$) δ 7.74 (d, 1H), 7.46 (m, 3H), 3.0 (m, 2H), 2.92 (m, 2H), 2.75 (m, 1H), 2.60 (m, 2H), 1.66 (m, 2H), 1.56 (m, 2H), 1.10 (t, 3H); MS m/z 238 (M+H).

Example 30

N-[2-(S)-(3,4-Dichlorophenyl)-4-[4-[2-(1-methyl)ethylsulfinylphenyl]-1-piperidinyl]-butyl]-N-methyl-3-cyano-1-naphthamide Citrate N-[2-(S)-(3,4-Dichlorophenyl)-4-[4-[2-(1-methyl)ethylsulfinylphenyl]-1-piperidinyl]-butyl]-N-methyl-3-cyano-1-naphthamide was prepared using the procedure described for N-[2-(S)-(3,4-Dichlorophenyl)-4-[4-[2-ethylsulfinylphenyl]-1-piperidinyl]butyl]-N-methyl-3-cyano-1-naphthamide (Example 29) except 2-iodopropane was used in place of iodoethane. $^1H$ NMR (DMSO-$d_6$) δ 8.64 (d, 1H), 8.08 (m, 1H), 7.69 (m, 5H), 7.45–6.43 (m, 6H), 4.54 (m, 1H), 3.67–1.71 (19H), 1.19 (d, 3H), 0.94 (d, 3H); MS m/z 660 (M+H).

Example 31

N-[2-(S)-(3,4-Dichlorophenyl)-4-[4-[2-(N-methyl-N-methoxyaminocarbonyl)phenyl]-1-piperidinyl]butyl]-N-methyl-3-cyano-1-naphthamide Citrate Using standard reductive amination conditions 4-(2-N-methyl-N-methoxycarboxamidophenyl)piperidine was reacted with N-[2-(S)-(3,4-dichlorophenyl)-4-oxobutyl]-N-methyl-3-cyano-1-naphthamide and converted to the citrate salt. MS m/z 657 (M+H).

The requisite 4-(2-N-methyl-N-methoxycarboxamidophenyl)piperidine was prepared as follows.

(a) 2-(N-Methyl-N-methoxycarboxamido)phenylpiperidine trifluoroacetate.

A mixture of 4-(2-carboxyphenyl)-1-N-Boc-piperidine (prepared by amine-protection and LiOH-mediated saponification of the methyl ester from the material obtained from Example 20, sub-part (b)) (176 mg), oxalyl chloride (76 μL), potassium carbonate (10 mg) and DMF (10 μL) was stirred in DCM (5 mL) for 2 h. The mixture was concentrated to afford the acid chloride which was used without purification. To a solution of the acid chloride in DCM (10 mL) was added N,O-dimethylhydroxylamine hydrochloride (62 mg), and triethylamine (176 μL). The mixture was stirred for 2 h, diluted with DCM (50 mL), washed with 1N HCl and saturated sodium bicarbonate, dried (MgSO$_4$), filtered, and concentrated to provide 2-(N-methyl-N-methoxycarboxamido)phenyl-1-N-Boc-piperidine- as a clear oil (205 mg). The material was N-deprotected by stirring for 1 h in a mixture of 5:1 DCM:trifluoroacetic acid to afford the product as the trifluoroacetate salt.

Example 32

N-[2-(S)-(3,4-Dichlorophenyl)-4-[4-[2-(N-methylaminocarbonyl)phenyl]-1-piperidinyl]-butyl]-N-methyl-3-cyano-1-naphthamide Citrate Using standard reductive amination conditions 4-(2-N-methylaminocarbonylphenyl)piperidine (prepared according to the procedure described in Example 31, except N,O-dimethylhydroxylamine hydrochloride was replaced with methyl amine (2M solution in THF)) was reacted with N-[2-(S)-(3,4-dichlorophenyl)-4-oxobutyl]-N-methyl-3-cyano- 1-naphthamide and converted to the citrate salt. MS m/z 627 (M+H).

Example 33

N-[2-(S)-(3,4-Dichlorophenyl)-4-[4-[2-(N,N-dimethylaminocarbonyl)phenyl]piperidinyl]butyl]-N-methyl-3-cyano-1-naphthamide Citrate Using standard reductive amination conditions 4-(2-N,N-dimethylaminocarbonylphenyl)piperidine (prepared according to the procedure described in Example 31, except N,O-dimethylhydroxylamine hydrochloride was replaced with dimethyl amine (2M solution in THF)) was reacted with N-[2-(S)-(3,4-dichlorophenyl)-4-oxobutyl]-N-methyl-3-cyano-1-naphthamide and converted to the citrate salt. MS m/z 641 (M+H).

Example 34

N-[(S)-2-(3,4-Dichlorophenyl)-4-[4-[2-trifluoromethylphenyl]-1-piperidinyl]butyl]-N-methyl-3-nitronaphthamide Citrate N-[(S)-2-(3,4-Dichlorophenyl)-4-[4-[2-trifluoromethylphenyl]-1-piperidinyl]butyl]-N-methylamine hydrochloride (0.155 g) was dissolved in DCM (10 mL). Triethylamine (0.061 g) was added followed by 3-nitro-1-naphthoyl chloride (0.069 g) (prepared from 3-nitro-1-naphthoic acid (Kice, J L, Lotey H; J. Org. Chem., 54, 3596 (1989)) and oxalyl chloride). The mixture was stirred overnight, diluted with saturated sodium bicarbonate and extracted with ethyl acetate. The organic phase was dried and evaporated. The residue was purified by chromatography, with DCM:methanol (30:1) as the eluent to give the free base (0.170 g) which was converted to the citrate salt. MS: m/z 658 (M+H). $^1$H NMR (DMSO d$_6$) δ 9.05 (m, 1H), 8.40–6.00 (m, 12H), 3.60–0.90 (m, 16H), 2.55 (m, 3H, N—CH$_3$).

The requisite amine was prepared as follows.

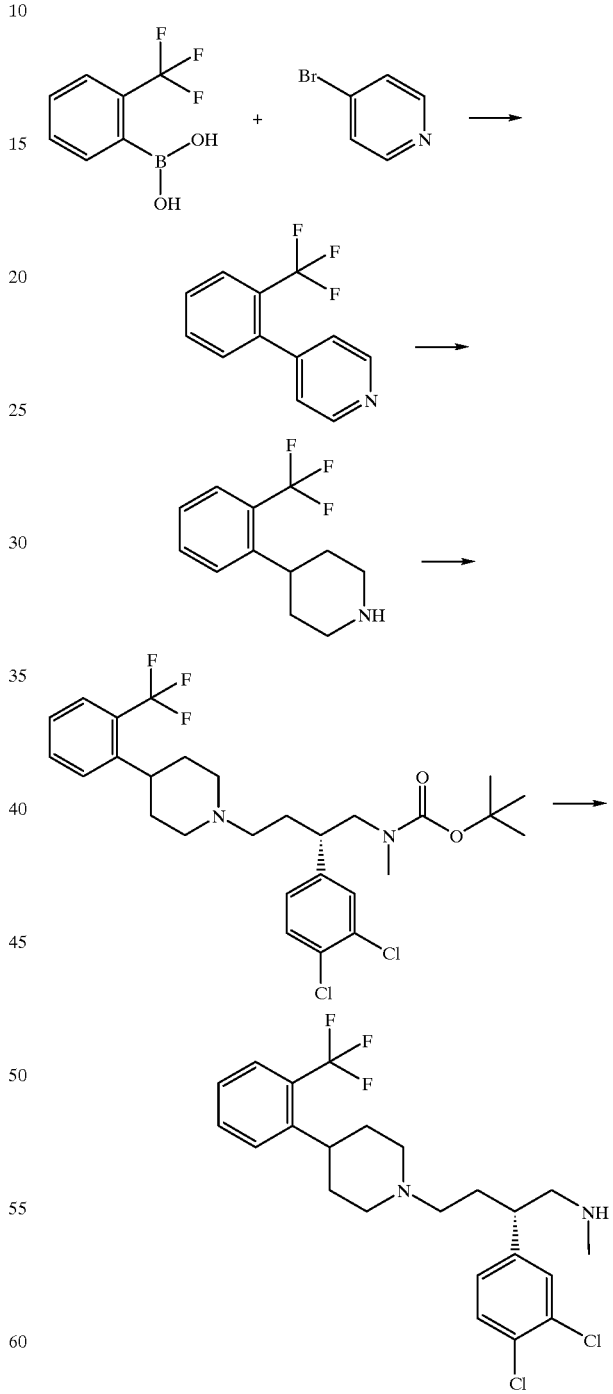

(a) 4-(2-Trifluoromethylphenyl)pyridine hydrochloride.

4-Bromopyridine hydrochloride (1.94 g) and tetrakis (triphenylphosphine) palladium(0) (0.36 g) were combined in dry 1,2-dimethoxyethane (50 mL) under nitrogen.

The mixture was stirred for 20 min then 2-trifluoromethylphenylboronic acid (1.94 g) was added followed immediately by a solution of sodium carbonate (2.48 g) in water (15 mL).

The mixture was heated under reflux for 5 h, then extracted with EtOAc. The organic extracts were dried and evaporated. The residue was purified by chromatography, with DCM:methanol (20:1) as the eluent to give the pyridine free base. The free base was dissolved in DCM and treated with an excess of ethereal hydrogen chloride to provide the title compound (1.96 g) as a white solid. MS: m/z 224(M+H). $^1$H NMR (CDCl$_3$) δ 8.88 (d, 2H), 7.90 (m, 3H), 7.76 (m, 2H), 7.38 (m, 1H).

(b) 4-(2-Trifluoromethylphenyl)piperidine hydrochloride.

4-(2-Trifluoromethylphenyl)pyridine hydrochloride (0.250 g) was dissolved in acetic acid (15 mL), platinum dioxide (0.100 g) was added and the mixture was shaken under hydrogen (50 psi) for 4 h. The solution was filtered, acidified with 4N HCl and evaporated to provide the piperidine hydrochloride (0.243 g) as a white solid. MS: m/z 230 (M+H). $^1$H NMR (DMSO d$_6$) δ 7.71 (m, 2H), 7.57 (d, J=9, 1H), 7.44 (m, 1H), 3.38 (m, 2H), 3.10 (m, 3H), 2.11 (m, 2H), 1.82 (m, 2H).

(c) N-[(S)-2-(3,4-Dichlorophenyl)-4-[2-trifluoromethylphenyl]-1-piperidinyl]butyl]-N-methyl-N-Boc-amine.

N-[(S)-2-(3,4-Dichlorophenyl)-4-oxobutyl]-N-methyl-N-Boc-amine (0.261 g) (Miller, S C; WO 9505377) was added to a solution of 4-(2-trifluoromethylphenyl)piperidine hydrochloride (0.180 g) and triethylamine (0.076 g) in methanol (15 mL). The mixture was stirred for 5 minutes then a methanol (4 mL) solution of sodium cyanoborohydride (0.060 g) was added dropwise and the reaction was stirred overnight at ambient temperature. Methanol was evaporated and the residue partitioned between EtOAc (20 mL) and aqueous sodium bicarbonate (10 mL). The organic phase was dried and evaporated. The residue was purified by chromatography with DCM:methanol (40:1) as the eluent, to give the title compound (0.328 g). MS: m/z 559 (M+H).

(d) N-[(S)-2-(3,4-Dichlorophenyl)-4-[4-[2-trifluoromethylphenyl]-1-piperidinyl]butyl]-N-methylamine hydrochloride.

N-[(S)-2-(3,4-Dichlorophenyl)-4-[4-[2-trifluoromethylphenyl]- 1-piperidinyl]butyl]-N-methyl-N-Boc-amine (0.328 g) was dissolved in EtOAc (20 mL), cooled to 0° C. and hydrogen chloride was bubbled through the solution for 10 minutes. The solution was evaporated to give desired title compound (0.311 g) as a white solid. MS: m/z 559 (M+H).

Example 35

N-[2-(S)-(3,4-Dichlorophenyl)-4-[4-[2-(methylsulfonyl)-4-methoxyphenyl]-1-piperidinyl]-butyl]-N-methyl-3-cyano-1-naphthamide Hydrochloride Using standard reductive amination conditions N-[2-(S)-(3,4-dichlorophenyl)-4-oxobutyl]-N-methyl-3-cyano-1-naphthamide (0.130 g) was reacted with 4-(2-methylsulfonyl-4-methoxyphenyl)piperidine (0.082 g) and the product (0.074 g) was converted to the hydrochloride salt. MS m/z 678 (M+H). $^1$H NMR (DMSO-d$_6$) δ 10.57 (m, 1H), 8.62 (m, 1H), 8.10 (m, 1H), 7.95–7.00 (m, 10H), 3.83 (s, 3H), 3.32 (s, 3H), 3.64–1.65 (m, 19H).

The requisite 4-(2-methylsulfonyl-4-methoxyphenyl) piperidine was prepared as follows.
(a) 4-(4-Methoxy-2-methylsulfonylphenyl)-N-Cbz-piperidine To a stirred solution of sodium periodate (0.267 g) dissolved in 20 mL 1:1 THF:H$_2$O was added 4-(4-methoxy-2-methylthiophenyl)-N-Cbz-piperidine (0.45g) [Example 2(f)] followed by 100 μL of a 4% w/w solution of OsO$_4$. The mixture was stirred at room temperature for 18 h, poured into 20 mL of saturated NaHCO$_3$, and extracted with DCM (3×30 mL). The organic extracts were combined, dried over Na$_2$SO$_4$, and evaporated to give 0.319 g of 4-(4-methoxy-2-(methylsulfonyl)phenyl)-N-Cbz-piperidine as an oil after chromatography (4:1 DCM:EtOAc). $^1$H NMR (CDCl$_3$) δ 7.56 (d, 1H), 7.47–7.30 (m, 5H), 7.12 (dd, 1H), 5.17 (s, 2H), 4.45–4.20 (m, 2H), 3.01–3.85 (s, 3H), 3.61 (tt, 1H), 3.11 (s, 3H), 2.78 (m, 2H), 1.85–1.5 (m, 4H).

(b) 4-(4-Methoxy-2-methylsulfonylphenyl)piperidine

To a solution of KOH (1.50 g) in 20 mL of 1:1 EtOH:H$_2$0 was added 1.23 g of 4-(4-methoxy-2-methylsulfonylphenyl)-N-Cbz-piperidine. The resulting mixture was heated reflux under N$_2$ atmosphere for 18 h, evaporated, dissolved in 10 mL H$_2$O, and extracted with CHCl$_3$. The organic extracts were combined, dried over Na$_2$SO$_4$, filtered, and concentrated under reduced pressure. The resulting residue was purified by chromatography (20:1 DCM in methanol containing 0.5% aqueous NH$_4$OH). MS m/z 270 (M+H).

Example 36

N-[(S)-2-(3,4-Dichlorophenyl)-4-[4-[tetrahydro-2-oxo-1(2H)-pyrimidinyl]-1-piperidinyl]-butyl]-N-methyl-3-cyano-1-naphthamide Citrate Hydrate (1:1:1.5)

A stirred solution containing 3-cyano-1-naphthoic acid (0.1 g, 0.5 mmol) [Example 1], N,N-diisopropylethylamine (0.16 g, 1.27 mmol), and dry DCM (2.5 mL) was treated with a solution of tetramethylfluoroformamidinium hexafluorophosphate (TFFH) (0.16 g, 0.61 mmol) and dry DCM (1.0 mL). After 10 min, a solution containing N-[(S)-2-(3,4-dichlorophenyl)-4-[4-[tetrahydro-2-oxo-1(2H)-pyrimidinyl]-1-piperidinyl]butyl]-N-methylamine (Miller, S C. WO 9505377) (0.21 g, 0.51 mmol) and dry DCM (1.0 mL) was added, and the solution stirred for 60 h. Additional DCM and 1M aqueous acetic acid were added. After mixing, the layers were allowed to separate, the organic layer was removed, and the aqueous HOAc layer was extracted with additional DCM (2×). The organic extracts were combined, washed (saturated NaHCO$_3$), dried (Na$_2$SO$_4$), filtered, and the DCM evaporated in vacuo. The residue was purified by chromatography (0–10% methanol in DCM), converted to the citrate salt and isolated by filtration from Et$_2$O to afford the title compound (210 mg) as a white solid. MS: m/z 592 (M+H). Analysis for C$_{32}$H$_{35}$Cl$_2$N$_5$O$_2$.C$_6$H$_8$O$_7$.1.5 H$_2$O: calculated: C, 56.23; H, 5.71; N, 8.63. found: C, 56.31; H, 5.34; N, 8.34.

Example 37

N-[(S)-2-(3,4-Dichlorophenyl)-4-[4-(2-oxo-1-piperidinyl)-1-piperidinyl]butyl]-N-methyl-3-cyano-1-naphthamide Citrate Hydrate (1:1:0.75)

Using standard acylation conditions 3-cyano-1-naphthoyl chloride (prepared from 3-cyano-1-naphthoic acid and oxalyl chloride) was reacted with N-[(S)-2-(3,4-dichlorophenyl)-4-[4-(2-oxo-1-piperidinyl)-1-piperidinyl] butyl]-N-methylamine (Miller, S C; WO 9410146).

A portion of the product was converted to the citrate salt and isolated by filtration from Et2O to afford the title compound as a white solid. MS: m/z 591 (M+H). Analysis for C33H36Cl2N4O2.C6H8O7.0.75 H2O: calculated: C, 58.76; H, 5.75; N, 7.03. found: C, 58.80; H, 5.63; N, 6.88.

Example 38

N-[2(S)-(3,4-Dichlorophenyl)-4-[4-(tetrahydro-2-oxo-1(2H)-pyrimidinyl)-1-piperidinyl]-butyl]-N-methyl-4-cyano-1-naphthalenecarboxamide Citrate Using standard acylation conditions 4-cyano-1-naphthoyl chloride (prepared from 4-cyano-1-naphthoic acid and oxalyl chloride) was reacted with (S)-2-(3,4-dichlorophenyl)-N-methyl-4-[(tetrahydro-2-oxo-1(2H)-pyrimidinyl)piperidinyl]butanamine (Miller, S. C. WO 9505377). The product was converted to the citrate salt. MS: m/z 592 (M+H).

The requisite 4-cyano-1-naphthoic acid was prepared as follows.
(a) Methyl 4-bromo-1-naphthoate.
A solution of 4-bromo-1-naphthoic acid (Fischer, A; et al, J. Chem. Soc., 1426 (1958)) oxalyl chloride (2.56 g), and DMF (5 μL) in DCM (100 mL) was stirred for 3 h, concentrated, then redissolved in DCM (5 mL). Methanol was added and stirring continued overnight.

Following concentration and purification by chromatography (DCM) the product was afforded as a white solid (4.85 g). $^1$H NMR (DMSO-$d_6$): δ 8.83–8.77 (m, 1H), 8.31–8.25 (m, 1 H), 8.01 (s, 1 H), 7.82–7.75 (m, 2H), 3.96 (s, 3 H); MS m/z 265 (M+H).
(b) 4-cyano-1-naphthoic acid.

A solution of methyl 4-bromo-1-naphthoate (0.509 g) copper (I) cyanide, (0.174 g), 1 drop of pyridine, and DMF (5 mL) was heated under reflux at 180° C. for 5 h. The hot solution was poured into 10 mL of aqueous concentrated NH$_4$OH and extracted with DCM.

The organic phase was washed successively with 1N HCl (20 mL) and brine (40 mL), dried (Na$_2$SO$_4$), filtered, and concentrated to afford methyl 4-cyano-1-naphthoate a colorless oil (0.213 g). MS m/z 196 (M−1). $^1$H NMR (DMSO-$d_6$): δ 8.74–8.69 (m, 1 H), 8.29–8.15 (m, 3 H), 7.92–7.83 (m, 2H), 3.99 (s, 3 H). The methyl ester was saponified by stirring a solution of the methyl ester, LiOH.H$_2$O (1 equivalent), THF (3 mL), water (1 mL) and methanol (1 mL) overnight at room temperature. The solution was diluted with saturated sodium bicarbonate and extracted with Et$_2$O. The aqueous layer was acidified to pH 2 by addition of 1N HCl and extracted with Et$_2$O. The organic layer was washed with water (30 mL) and brine (40 mL), dried (sodium sulfate), filtered, and concentrated to afford 4-cyano-1-naphthoic acid as an oil.

Example 39

N-[(S)-2-(3,4-Dichlorophenyl)-4-[4-[tetrahydro-2-oxo-1(2H)-pyrimidinyl]-1-piperidinyl]butyl]-N-methyl-6-cyano-1-naphthamide Citrate To a stirred solution of 6-cyano-1-naphthoic acid (0.2 g, 1.01 mmol) in dry DCM (5 mL) was added oxalyl chloride (0.11 mL, 1.26 mmol) and 2 drops of DMF. The solution was stirred at room temperature for 3 h and concentrated to provide the acid chloride; 6-cyano-1-naphthoyl chloride (0.219 g), as a off-white solid which was used without further purification.

Using standard acylation conditions (S)-2-(3,4-dichlorophenyl)-N-methyl-4-[(tetrahydro-2-oxo-1(2H)-pyrimidinyl)piperidinyl]butanamine (Miller, S C.; WO 9505377) was reacted with 6-cyano-1-naphthoyl chloride and converted to the citrate salt. MS m/z 592 (M+H). Analysis for $C_{32}H_{35}Cl_2N_5O_2$.1.0 $C_6H_8O_7$.1.0 $H_2O$: calculated: C, 56.86; H, 5.65; N, 8.72. found: C, 56.81; H, 5.51; N, 8.54.

Example 40

N-[2-(4-Chlorophenyl)-4-[4-[tetrahydro-2-oxo-1(2H)-pyrimidinyl]-1-piperidinyl]butyl]-N-methyl-3-nitro-1-naphthamide Citrate Using standard reductive amination conditions 4-(tetrahydro-2-oxo-1(2H)-pyrimidinyl)piperidine (Miller, S C; Jacobs, R T; Shenvi, A B. EP 739891) was reacted with N-[2-(4-chlorophenyl)-4-oxobutyl]-N-methyl-3-nitro-1-naphthamide [Example 3] and converted to the citrate salt. MS m/z 578 (M+H). Analysis for $C_{31}H_{36}ClN_5O_4$.1.0 $C_6H_8O_7$.0.8 $H_2O$: calculated: C, 56.64; H, 5.86; N, 8.92; found: C, 56.60; H, 5.74; N, 8.69.

Example 41

N-[2-(3,4-Difluorophenyl)-4-[4-[tetrahydro-2-oxo-1(2H)-pyrimidinyl]-1-piperidinyl]butyl]-N-methyl-3-nitro-1-naphthamide Citrate Using standard reductive amination conditions 4-(tetrahydro-2-oxo-1(2H)-pyrimidinyl)piperidine (Miller, S C; Jacobs, R T; Shenvi, A B. EP 739891) was reacted with N-[2-(3,4-difluorophenyl)-4-oxobutyl]-N-methyl-3-nitro-1-naphthamide [Example 13] and converted to the citrate salt. MS m/z 580 (M+H); analysis for $C_{31}H_{35}F_2N_5O_4$.1.07 $C_6H_8O_7$.1.06 $H_2O$: calculated: C, 55.88; H, 5.72; N, 8.71. found: C, 55.94; H, 5.54; N 8.51.

Example 42

N-[(S)-2-(3,4-Dichlorophenyl)-4-[4-[tetrahydro-2-oxo-1(2H)-pyrimidinyl]-1-piperidinyl]-butyl]-N-methyl-3-nitro-1-naphthamide Citrate Using standard reductive amination conditions N-[(S)-2-(3,4-dichlorophenyl)-4-oxobutyl]-N-methyl-3-nitro-1-naphthalenecarboxamide (0.250 g) was treated with 4-(tetrahydro-2-oxo-1(2H)-pyrimidinyl)piperidine (Miller, S C; Jacobs, R T; Shenvi, A B. EP 739891) (0.102 g). The free base (0.102 g) was converted to the citrate salt. MS m/z: 612 (M+H).

Example 43

N-[(S)-2-(3,4-Dichlorophenyl)-4-[4-[tetrahydro-2-oxo-1(2H)-pyrimidinyl]-1-piperidinyl]butyl]-N-methyl-6-nitro-1-naphthamide Citrate Using standard acylation conditions N-[(S)-2-(3,4-dichlorophenyl)-4-[4-[tetrahydro-2-oxo-1(2H)-pyrimidinyl]-1-piperidinyl]butyl]-N-methylamine (Miller, S C; WO 9505377) was reacted with 6-nitro-1-naphthoyl chloride (Dewar, M J S and Grisdale, P J; J. Amer Chem. Soc., 84, 3541 (1962)) and converted to the citrate salt. MS m/z 612 (M+H); analysis for $C_{31}H_{35}Cl_2N_5O_4$.1.05 $C_6H_8O_7$.0.7 $H_2O$: calculated: C, 54.18; H, 5.46; N, 8.47; found: C, 54.31; H, 5.53; N, 8.18.

Example 44

N-[(S)-2-(3,4-Dichlorophenyl)-4-[4-(2-oxo-1-piperidinyl)-4-(N-methylaminocarbonyl)]-1-piperidinyl]butyl]-N-methyl-3-cyano-1-naphthamide Citrate Hydrate (1:1:0.5)

Using standard reductive amination conditions N-[2-(S)-(3,4-dichlorophenyl)-4-oxobutyl]-N-methyl-3-cyano-1- naphthamide was reacted with 4-(2-oxo-1-piperidinyl)-4-(N-methylaminocarbonyl)piperidine (Miller, S C; Jacobs, R T; Shenvi, A B. EP 739891). The product was converted to the citrate salt. MS: m/z 648 (M+H). Analysis for $C_{35}H_{39}Cl_2N_5O_3 \cdot C_6H_8O_7$ 0.5 .$H_2O$: calculated: C, 57.95; H, 5.69; N, 8.24. found: C, 57.95; H, 5.63; N, 8.29.

The title compound was also converted to the citrate monohydrate (1.0:1.0:1.0).

The intermediate N-[2-(S)-(3,4-dichlorophenyl)-4-oxobutyl]-N-methyl-3-cyano-1-naphthamide was prepared according to Example 2.

Example 45

N-[(S)-2-(3,4-Dichlorophenyl)-4-[4-(2-oxo-1-piperidinyl)-4-(N,N-dimethylaminocarbonyl)]-1-piperidinyl]butyl]-N-methyl-3-cyano-1-naphthamide Citrate Hydrate (1:1:0.7)

Using standard reductive amination conditions 4-(2-oxo-1-piperidinyl)-4-(N,N-dimethylaminocarbonyl)piperidine (Miller, S C; Jacobs, R T; Shenvi, A B. EP 739891) was reacted with N-[2-(S)-(3,4-dichlorophenyl)-4-oxobutyl]-N-methyl-3-cyano-1-naphthamide (Example 2). The product was converted to the citrate salt. MS m/z 662 (M+H); analysis for $C_{36}H_{41}Cl_2N_5O_3 \cdot C_6H_8O_7 \cdot 0.7\ H_2O$: calculated: C, 58.16; H, 5.85; N, 8.07. found: C, 58.18; H, 5.74; N, 7.97.

Example 46

N-(4-[4-(Tetrahydro-2-oxo-1(2H)-pyrimidinyl)-4-(methylaminocarbonyl)-1-piperidinyl]-2-(4-chlorophenyl)-butyl)-N-methyl-3-cyano-1-naphthamide Citrate Using standard reductive amination conditions N-(4-[4-(tetrahydro-2-oxo-1(2H)-pyrimidinyl)-4-(methylaminocarbonyl)piperidine (Miller, S C; WO 9512577) was reacted with N-[2-(4-chlorophenyl)-4-oxobutyl]-N-methyl-3-cyano-1-naphthamide and converted to the citrate salt. $^1$H NMR (CDCl$_3$) (amide rotational isomers evident) δ 8.20 (m), 7.92 (m), 7.69–7.57 (br m), 7.47–7.20 (br m), 6.93 (d, J=8.4), 6.82 (d, J=8.4), 6.67 (d, J=7.8), 6.51 (m) 4.62 (m) 3.49–3.21 (br m) 2.58 (s) 2.39–2.17 (br m) 1.95–1.79 (m); MS m/z 615.0 (M+H).

The requisite aldehyde was prepared as follows.
(a) N-[2-(4-Chlorophenyl)-4-hydroxybutyl]-N-methyl-3-cyano-1-naphthamide.

Oxalyl chloride (195 μL, 2.23 mmol) was added to a solution of 3-cyano-1-naphthoic acid (400 mg, 2.03 mmol) in DCM (10 mL). The solution was stirred for three hours, during which time three portions (30 μL each) of 10% DMF in DCM were added. The solution was concentrated to a white powder under reduced pressure, dried under vacuum, and dissolved in DCM (15 mL). After cooling to 0° C., N-[2-(4-chlorophenyl)-4-hydroxybutyl]-N-methylamine (434 mg, 2.03 mmol, dissolved in 5 mL DCM) and NaOH (1.0 M, 2.54 mL) were added. After warming to room temperature stirring was continued overnight. The mixture was extracted with 30 mL portions of 0.5 M HCl and saturated sodium bicarbonate, dried (MgSO$_4$), filtered, and concentrated under reduced pressure to a light yellow foam (692 mg, 1.76 mmol, 87%). $^1$H NMR (CDCl$_3$) (amide rotational isomers evident) δ 8.09 (s), 7.85 (m), 7.72–7.50 (br m), 7.43–4.35 (br m), 6.92 (d, J=6.3), 6.85 (d, J=7.8), 6.69 (m), 6.65 (m), 4.57 (br m), 3.99 (br m), 3.70 (m), 3.50–3.10 (br m), 2.67 (s), 2.03 (m), 1.89 (m), 1.58 (m); MS m/z 393.0 (M+H).

(b) N-[2-(4-Chlorophenyl)-4-oxobutyl]-N-methyl-3-cyano-1-naphthamide.

A solution of DMSO (356 μL, 5.01 mmol) in DCM (5 mL) was added dropwise over 5 min to a stirred solution of oxalyl chloride (219 μL, 2.51 mmol) in DCM (5 mL) at −70° C.

After stirring for 15 min, N-[2-(4-chlorophenyl)-4-hydroxybutyl]-N-methyl-3-cyano-1-naphthamide (788 mg, 2.01 mmol) was added dropwise as a solution in DCM (5 mL).

Stirring was continued for 45 min at −70° C., warmed to −45° C., and stirred for 30 min.

The solution was cooled to −70° C. and triethylamine (1.41 mL, 10.03 mmol) (dissolved in 5 mL of DCM) was added dropwise. After stirring 15 min, the mixture was allowed to warm to room temperature, diluted with DCM, and extracted with 0.5 M HCl (30 mL), saturated sodium bicarbonate (30 mL), dried (MgSO$_4$), and concentrated to a clear oil which was purified by chromatography (50% EtOAc in hexanes) to afford the product as a clear oil (543 mg, 1.39 mmol, 70%). $^1$H NMR (CDCl$_3$) (amide rotational isomers evident) δ 9.71 (s), 9.60 (s), 8.18 (m), 7.86 (t, J=7.8), 7.68–7.29 (m), 7.51 (m), 6.87, (t, J=7.2), 6.67 (d, J=8.4), 6.57 (m), 4.56 (br m), 3.98, (br m), 3.71, (br m), 3.42 (m), 2.97, (m), 2.67 (m); MS m/z 391.0 (M+H).

Example 47

N-[(S)-2-(3,4-Dichlorophenyl)-4-[4-(tetrahydro-2-oxo-1(2H)-pyrimidinyl)-4-(methylaminocarbonyl)]-1-piperidinyl]butyl]-N-methyl-3-cyano-1-naphthamide Citrate Hydrate (1:1:2)

Using standard reductive amination conditions (except that acetic acid-sodium acetate buffer was substituted for acetic acid) N-[(S)-2-(3,4-dichlorophenyl)-4-oxobutyl]-N-methyl-3-cyano-1-naphthamide (145 mg, 0.34 mmol) was reacted with 4-(tetrahydro-2-oxo-1(2H)-pyrimidinyl)-4-(methylaminocarbonyl)piperidine (Miller, S C; WO 9512577) (79.1 mg, 0.329 mmol), converted to the citrate salt, and isolated by filtration from Et$_2$O to afford the title compound (162.5 mg) as a white powder. MS m/z 649 (M+H); analysis for $C_{34}H_{38}Cl_2N_6O_3 \cdot C_6H_8O_7 \cdot 2.0\ H_2O$: calculated: C, 54.73; H, 5.74; N, 9.57; found: C, 54.92; H, 5.41; N, 9.29.

Example 48

N-[2-(4-Chlorophenyl)-4-[4-(tetrahydro-2-oxo-1(2H)-pyrimidinyl)-4-(methylaminocarbonyl)]-1-piperidinyl]butyl]-N-methyl-3-nitro-1-naphthamide Citrate Using standard reductive animation conditions 4-(tetrahydro-2-oxo-1(2H)-pyrimidinyl)-4-(methylaminocarbonyl)piperidine (Miller, S C., WO 9512577) was reacted with N-[2-(4-chlorophenyl)-4-oxobutyl]-N-methyl-3-nitro-1-naphthamide and converted to the citrate salt. MS m/z 635 (M+H). Analysis for $C_{33}H_{39}ClN_6O_5 \cdot 1.0\ C_6H_8O_7 \cdot 1.3\ H_2O$: calculated: C, 56.06; H, 5.88; N, 9.88. found: C, 55.04; H, 5.74; N, 9.74.

Example 49

N-[2-(3,4-Difluorophenyl)-4-[4-(tetrahydro-2-oxo-1(2H)-pyrimidinyl)-4-(methylaminocarbonyl)]-1-piperidinyl]butyl]-N-methyl-3-nitro-1-naphthamide Citrate Using standard reductive amination conditions 4-(tetrahydro-2-oxo-1(2H)-pyrimidinyl)-4-

(methylaminocarbonyl)piperidine (Miller, S C.; WO 9512577) was reacted with N-[2-(3,4-difluorophenyl)-4-oxobutyl]-N-methyl-3-nitro-1-naphthamide and converted to the citrate salt. MS m/z 637 (M+H); analysis for $C_{33}H_{38}F_2N_6O_5.1.1.C_6H_8O_7.1.2.H_2O$: calculated: C, 54.69; H, 5.70; N, 9.66. found: C, 54.62; H, 5.52; N, 9.46.

Example 50

N-[(S)-2-(3,4-Dichlorophenyl)-4-{4-(2-oxo-1-piperidinyl)-4-N,N-dimethylaminocarbonyl)}-1-piperidinyl]butyl]-N-methyl-3-nitro-1-naphthamide Using standard reductive animation conditions N-[(S)-2-(3,4-dichlorophenyl)-4-oxobutyl]-N-methyl-3-nitro-1-naphthamide (0.10 g) was reacted with 4-(2-oxo-1-piperidinyl)-4-(dimethylaminocarbonyl)piperidine (Miller, S C; Jacobs, R T; Shenvi, A B. EP 739891) (0.060 g). The free base (0.093 g) was converted to the citrate salt. MS: m/z 682 (M+H).

Example 51

N-[(S)-2-(3,4-Dichlorophenyl)-4-[4-(tetrahydro-2-oxo-1(2H)-pyrimidinyl)-4-(methylaminocarbonyl)]-1-piperidinyl]butyl]-N-methyl-3-nitro-1-naphthamide Using standard reductive amination conditions N-[(S)-2-(3,4-dichlorophenyl)-4-oxobutyl]-N-methyl-3-nitro-1-naphthamide (0.150 g) was treated with 4-(tetrahydro-2-oxo-1(2H)-pyrimidinyl)- 4-(methylaminocarbonyl)-1-piperidine (Miller, S C. WO 9512577) (0.089 g). The free base (0.123 g) was converted to the citrate salt. MS m/z 669 (M+H).

Example 52

N-[(S)-2-(3,4-Dichlorophenyl)-4-{4-(2-oxo-1-piperidinyl)-4-(N-methylaminocarbonyl)}-1-piperidinyl]butyl]-N-methyl-3-nitro-1-naphthamide Citrate Using standard reductive amination conditions, N-[(S)-2-(3,4-dichlorophenyl)-4-oxobutyl]-N-methyl-3-nitro-1-naphthamide (0.300 g) was treated with 4-(2-oxo-1-piperidinyl)-4-(methylaminocarbonyl)piperidine (Miller, S C; Jacobs, R T; Shenvi, A B. EP 739891) (0.1773 g). The free base (0.296 g) was converted to the citrate salt. MS m/z 668 (M+H).

Example 53

N-[(S)-2-(3,4-Dichlorophenyl)-4-oxobutyl]-N-methyl-3-nitro-1-naphthamide

By the method of Example 3f, 3-nitro-1-naphthoyl chloride was reacted with (S)-2-(3,4-dichlorophenyl)-4-hydroxybutyl-N-methylamine to give N-[(S)-2-(3,4-dichlorophenyl)-4-hydroxybutyl]-N-methyl-3-nitro-1-naphthamide. This was reacted by the method of Example 3g to give the title compound: $^1$H NMR (300 MHz, CDCl$_3$) δ 9.65 (s), 9.44 (s), 9.07–9.02 (m), 8.38–6.04 (m), 4.44–1.18 (m); MS APCI, m/z=445 (M$^+$).

Example 54

N-[2-(S)-(3,4-Dichlorophenyl)-4-[4-[4-carbamoyl-(R,S)-2-methylsulfinylphenyl]-1-piperidinyl]butyl]-N-methyl-3-cyano-1-naphthamide Citrate Using standard reductive alkylation conditions N-[2-(S)-(3,4-dichlorophenyl)]-4-oxobutyl-N-methyl-3-cyano-1-naphthamide (0.115 g) was reacted with 4-(4-carbamoyl-2-(R,S)-methylsulfinylphenyl)piperidine (0.071 g) and converted to the citrate salt. MS m/z 675 (M+); $^1$H NMR (DMSO d$_6$) δ 8.70–8.58 (m, 1H), 8.25–6.40 (m, 13H), 3.60–1.50 (m, 26H); analysis for $C_{36}H_{36}Cl_2N_4O_3S.1.0$ citric acid.1.0 $H_2O.0.25$ $Et_2O$: calculated; C, 57.11; H, 5.41; N, 6.20; found; C, 57.06; H, 5.18; N, 6.28.

The requisite 4-(4-carbamoyl-2-(R,S)-methylsulfinylphenyl)piperidine was prepared as follows:

a) 4-[2-Methylsulfinyl-4-bromophenyl]piperidine.

To a stirred solution of 4-(2-sulfinylphenyl)piperidine (Jacobs, R; Shenvi, A; EP 630887) (0.496 g) dissolved in 5 mL of acetic acid was added a solution of bromine (0.715 g in 15 mL of acetic acid). The mixture was heated at 75° C. for 80 min. The cooled mixture was quenched with 3 mL H$_2$O, the solvent was evaporated, and the residue was dissolved in H$_2$O. The aqueous mixture was basified to pH 14 by addition of KOH and extracted with CHCl$_3$ (3×15 mL). The organic extracts were combined, dried over Na$_2$SO$_4$, evaporated, and purified by chromatography (19:1 DCM:methanol containing 0.5% aqueous NH$_4$OH) to afford the product (0.421 g) as a light yellow solid. MS m/z 302 (M+H). $^1$H NMR (CDCl$_3$) δ 7.86 (d, 1H), 7.61 (dd, 1H), 7.52 (d, 1H), 3.25–3.35 (m, 2H), 3.08–2.60 (m, 7H), 2.04–1.61 (m, 4H).

b) 4-[2-Methylsulfinyl-4-bromophenyl]-N-Cbz-piperidine.

To a stirred solution of 4-[2-methylsulfinyl-4-bromophenyl]piperidine (2.70 g) dissolved in 140 mL THF was added 2.60 mL triethylamine followed by 1.74 g of benzylchloroformate. After 18 h THF was evaporated, the residue was dissolved in 100 mL DCM, extracted with 0.5 M HCl (3×40 mL), and saturated NaHCO$_3$ (2×50 mL). The organic extract was dried over Na$_2$SO$_4$ and evaporated to give an oil which was purified by chromatography (4:1 EtOAc:DCM) to give 3.39 g of product. $^1$H NMR (CDCl$_3$) δ 7.87 (d, 1H), 7.61 (dd, 1H), 7.49–7.32 (m, 6H), 5.17 (s, 2H), 4.30–4.21 (m, 2H), 2.99–2.75 (m, 3H), 2.70 (s, 3H), 1.95–1.55 (m, 4H).

c) 4-[2-Methylsulfinyl-4-methoxycarbonylphenyl]-N-Cbz-piperidine.

To a mixture of DMSO (75 mL) and MeOH (75 mL) was added 1,3-bis(diphenylphosphino)propane (0.536 g), palladium acetate (0.331 g), 4-[2-methylsulfinyl-4-bromophenyl]-N-Cbz-piperidine (2.840 g), and 2.00 mL triethyl amine. The mixture was purged with carbon monoxide for 20 min then heated at 70° C. under carbon monoxide (1 atm) for 18 h. The mixture was poured into 250 mL of H$_2$O and extracted with 1:1 EtOAc:Et$_2$O (2×75 mL). The organic layer was extracted with H$_2$O (5×75 mL), dried over Na$_2$SO$_4$, and evaporated. The residue was purified by chromatography (4:1 EtOAc:DCM) to give 2.39 g of product. MS m/z 416 (M+H). $^1$H NMR (CDCl$_3$) δ 8.17–8.07 (m, 2H), 7.96 (d, 1H), 7.42–7.28 (m, 5H), 5.18 (s, 2H), 4.50–4.32 (m, 2H), 3.95 (s, 3H), 2.99–2.80 (m, 3H), 2.73 (s, 3H), 1.95–1.55 (m, 4H).

d) 1-Benzyloxycarbonyl-4-(4-carboxy-2-(R,S)-sulfinylphenyl)piperidine

To a solution of 4-[2-methylsulfinyl-4-methoxycarbonylphenyl]-N-Cbz-piperidine (0.120 g) dissolved in 10 mL 1:1 THF:H$_2$O was added 0.038 g LiOH. After heating the mixture at 60° C. for 18 h, 2 mL of 1M HCl was added and the mixture was extracted with DCM (3×10 mL). The organic extracts were combined, dried over Na$_2$SO$_4$, evaporated, and purified by chromatography (10:1 DCM:methanol containing 1.5% aqueous NH$_4$OH) to give a solid (0.107 g). MS m/z 402 (M+H). $^1$H NMR (CDCl$_3$) δ 8.05–7.72 (m, 3H), 7.48–7.15 (m, 5H), 6.61 (br s, 1H), 5.11

(s, 2H), 4.50–4.05 (m, 2H), 2.95–2.50 (m, 3H), 3.60 (s, 3H), 1.93–1.38 (m, 4H).

e) 4-(4-Carbamoyl-2-(R,S)-sulfinylphenyl)piperidine.

To a solution of 1-benzyloxycarbonyl-4-(4-carboxy-2-(R,S)-sulfinylphenyl)piperidine (1.28 g) dissolved in 45 mL DCM was added 1.45 mL of N,N-diisopropylethylamine. Mixture was stirred for 10 min and then 1.017 g tetramethylfluoroformamidiniumhexafluorophosphate was added and stirring was continued for 1 h. At this point $NH_3$ was bubbled through the solution for 30 min. Then 20 mL of saturated $NaHCO_3$ was added and the result was extracted with DCM (3×10 mL). Extracts were combined, dried over $Na_2SO_4$, and evaporated. The material was recrystallized from EtOAc:MeOH (3:1). $^1$H NMR ($CDCl_3$) δ 8.09 (d, 1H), 7.85–7.78 (d, 2H), 7.42–7.30 (m, 5H), 6.16 (br s, 1H), 5.72 (br s, 1H), 5.17 (s, 2H), 4.50–4.2 (m, 2H), 2.99–2.78 (m, 3H), 2.73 (s, 3H), 1.95–1.60 (m, 4H); MS m/z 423 (M+Na). N-deprotection of 1-benzyloxycarbonyl-4-(4-carboxamide-2-(R,S)-sulfinylphenyl)piperidine was accomplished using trifluoroacetic acid under standard conditions. $^1$H NMR ($CDCl_3$, TFA-$d_4$) δ 8.17 (d, 1H), 8.04 (dd, 1H), 7.98 (d, 1H), 3.79–3.61 (m, 2H), 3.45–3.20 (m, 3H), 2.97 (s, 3H), 2.42–1.95 (m, 4H); MS m/z 267 (M+H).

Example 55

N-[2-(S)-(3,4-Dichlorophenyl)-4-[4-[2-(R,S)-methylsulfinyl-4-methoxycarbonylphenyl]-1-piperidinyl]butyl]-N-methyl-3-cyano-1-naphthamide Citrate Using standard reductive alkylation conditions N-[2-(S)-(3,4-dichlorophenyl)]-4-oxobutyl-N-methyl-3-cyano-1-naphthamide (0.250 g) was reacted with 4-[2-(R,S)-methylsulfinyl-4-methoxycarbonylphenyl]piperidine (0.164 g) and converted to the citrate salt. MS m/z 690 (M+); $^1$H NMR (DMSO $d_6$) δ 8.70–8.58 (m, 1H), 8.20–7.40 (m, 11H), 3.89 (s, 3H), 3.55–2.30 (m, 19H), 2.20–1.50 (m, 7H).

The requisite 4-(2-(R,S)-sulfinyl-4-methoxycarbonylphenyl)piperidine was prepared as follows.

N-tert-Butylcarbamate-4-[2-(R,S)-methylsulfinyl-4-methoxycarbonylphenyl)piperidine was prepared from 4-(2-(R,S)-sulfinyl-4-bromophenyl)piperidine in an analogous fashion to that described for N-benzyloxycarbonyl-4-[2-(R,S)-methylsulfinyl-4-methoxycarbonylphenyl]piperidine (Example 54). N-protection was achieved using di(tert-butyl)dicarbonate in dioxane solvent using aq. NaOH as the base. Carbonylation of N-tert-butylcarbamate-4-(2-(R,S)-sulfinyl-4-bromophenyl)piperidine was performed using a procedure like that described in Example 54 to give N-tert-butylcarbamate-4-(2-(R,S)-sulfinyl-4-methoxycarbonylphenyl)piperidine. $^1$H NMR ($CDCl_3$) δ 8.15–8.05 (m, 2H), 7.99–7.95 (m, 1H), 4.40–4.15 (m, 2H), 3.95 (s, 3H), 2.95–2.65 (m, 3H), 2.73 (s, 3H), 1.95–1.45 (m, 4H), 1.50 (s, 9H). N-deprotection of N-tert-butylcarbamate-4-(2-(R,S)-sulfinyl-4-methoxycarbonylphenyl)piperidine was accomplished using trifluoroacetic acid under standard conditions to give 4-(2-(R,S)-sulfinyl-4-methoxycarbonylphenyl)piperidine. $^1$H NMR ($CDCl_3$) δ 8.15–8.03 (m, 3H), 3.94 (s, 3H), 3.30–3.15 (m, 2H), 2.90–2.65 (m, 4H), 2.72 (s, 3H), 1.95–1.50 (m, 4H); MS m/z 282 (M+H).

Example 56

N-[2-(S)-(3,4-Dichlorophenyl)-4-[4-[4-hydroxy-(R,S)-2-(methylsulfinyl)phenyl]-1-piperidinyl]butyl]-N-methyl-3-cyano-1-naphthamide Citrate Using standard reductive alkylation conditions N-[2-(S)-(3,4-dichlorophenyl)]-4-oxobutyl-N-methyl-3-cyano-1-naphthamide (0.429 g) was reacted with 4-(4-hydroxy-2-(R,S)-methylsulfinyl)phenyl)piperidine (0.239 g) and converted to the citrate salt. MS m/z 648 (M+); $^1$H NMR (DMSO $d_6$) δ 9.93–9.78 (m, 1H), 8.70–8.58 (m, 1H), 8.20–8.00 (m, 1H), 7.85–6.40 (m, 10H), 3.55–2.30 (m, 19H), 2.20–1.50 (m, 7H); analysis for $C_{35}H_{35}Cl_2N_3O_3S.1.0$ Citric Acid.1.5 $H_2O.0.25$ $Et_2O$: calculated; C, 56.92; H, 5.52; N, 4.74; found; C, 57.03; H, 5.26; N, 4.90.

The piperidine was prepared as follows:

a) 4-[4-Methoxy-2-methylthiophenyl]piperidine.

1-Benzyloxycarbonyl-4-[4-methoxy-2-methylthiophenyl]piperidine (Example 2) was N-deprotected using trifluoroacetic acid under standard conditions to give 4-[4-methoxy-2-methylthiophenyl]piperidine; $^1$H NMR ($CDCl_3$) δ 7.15 (d, 1H), 6.76 (d, 1H), 6.69 (dd, 1H), 3.80 (s, 3H), 3.18 (dm, 2H), 3.01 (tt, 1H), 2.78 (td, 2H), 2.45 (s, 3H), 1.82 (dm, 2H), 1.66 (s, 1H), 1.58 (qd, 2H); MS m/z 238 (M+H).

b) 4-[4-Hydroxy-2-methylthiophenyl]piperidine.

A mixture of pyridinium hydrobromide (20.76 g) and 4-[4-methoxy-2-methylthiophenyl]piperidine (6.16 g) was heated at 225° C. for 18 h. The reaction mixture was cooled, dissolved in 200 mL $H_2O$, adjusted to pH 7 with 1N KOH, and extracted with hexane (4×50 mL). The aqueous layer was concentrated under reduced pressure to give an oil which was dissolved in 200 mL EtOH and stirred for 0.5 h. The precipitate was filtered and washed with EtOH (2×40 mL). The filtrate and all washes were combined and concentrated under reduced pressure. The crude product was purified by chromatography (9:1 DCM:MeOH) to give 6.06 g of 4-[4-hydroxy-2-methylthiophenyl]piperidine as the hydrobromide salt. $^1$H NMR (DMSO $d_6$) δ 9.44 (s, 1H), 8.49 (m, 2H), 6.97 (d, 1H), 6.66 (d, 1H), 6.58 (dd, 1H), 3.43–3.30 (dm, 2H), 3.13–2.95 (m, 3H), 2.42 (s, 3H), 1.91–1.61 (m, 4H); MS m/z 225 (M+H).

c) 4-[4-Hydroxy-2-(R,S)-methylsulfinylphenyl]piperidine.

To a rapidly stirring slurry of 4-[4-hydroxy-2-methylthiophenyl]piperidine hyrdobromide (2.57 g) and triethylamine (4.00 mL) in 200 mL THF was slowly added 2.50 mL of benzyl chloroformate over 10 min. The mixture was stirred for 18 h, quenched with 20 mL saturated $NaHCO_3$, and THF was concentrated under reduced pressure. Residue was stirred with 50 mL saturated $NaHCO_3$ and extracted with DCM (3×50 mL). Extracts were combined, dried over $Na_2SO_4$, and concentrated under reduced pressure to give an oil which was dissolved in 160 mL 1:1 THF:$H_2O$. To this was added 0.26 g LiOH and mixture was stirred for 18 h. THF was evaporated under reduced pressure, aqueous residue was acidified with 15 mL 1N HCl, and this was extracted with DCM (4×40 mL). Extracts were combined, dried over $Na_2SO_4$, and concentrated under reduced pressure to give an oil which was purified by chromatography (2:3 EtOAc:hexane) to give 1.71 g of solid product; $^1$H NMR ($CDCl_3$) δ 7.45–7.25 (m, 5H), 6.99 (d, 1H), 6.70 (d, 1H), 6.59 (dd, 1H), 5.16 (s, 2H), 5.03 (s, 1H), 4.41–4.25 (m, 2H), 3.04 (tt, 1H), 3.00–2.83 (m, 2H), 2.44 (s, 3H), 1.90–1.45 (m, 4H); MS m/z 358 (M+H). 1-Benzyloxycarbonyl-4-[4-hydroxy-2-methylthiophenyl]piperidine was oxidized with $NaIO_4$ in 1:1 THF:$H_2O$ using standard conditions to give 1-benzyloxycarbonyl-4-[4-hydroxy-2-(R,S)-methylsulfinylphenyl]piperidine; $^1$H NMR ($CDCl_3$) δ 8.50 (s, 1H), 7.79 (d, 1H), 7.42–7.30 (m, 5H), 7.12 (d, 1H), 6.95 (dd, 1H), 5.16 (s, 2H), 4.42–4.20 (m, 2H), 2.95–2.65 (m, 3H), 2.74 (s, 3H), 1.90–1.50 (m, 4H); MS m/z 374 (M+H). 1-Benzyloxycarbonyl-4-[4-hydroxy-2-(R,S)-methylsulfinylphenyl]piperidine was N-deprotected using trifluoroacetic acid under standard conditions to give 4-[4- hydroxy-2-(R,S)-methylsulfinylphenyl]piperidine and used without purification. MS m/z 240 (M+H).

Example 57

N-[2-(S)-(3,4-Dichlorophenyl)-4-[4-[4-chloro-(R,S)-2-methylsulfinylphenyl]-1-piperidinyl]butyl]-N-methyl-3-cyano-1-naphthamide Citrate

Using standard reductive alkylation conditions N-[2-(S)-(3,4-dichlorophenyl)]-4-oxobutyl-N-methyl-3-cyano-1-naphthamide (0.302 g) was reacted with 4-(4-chloro-2-(R,S)-methylsulfinyl)phenyl)piperidine (0.181 g) and converted to the citrate salt. MS m/z 666 (M+); $^1$H NMR (DMSO $d_6$) δ 8.70–8.58 (m, 1H), 8.20–8.00 (m, 1H), 7.85–6.40 (m, 11H), 3.50–1.50 (m, 26H); analysis for $C_{35}H_{34}Cl_3N_3O_2S.1.0$ citric acid.1.5 $H_2O$.0.25 $Et_2O$: calculated; C, 56.03; H, 5.26; N, 4.67; found; C, 55.98; H, 5.02; N, 4.67.

The requisite 4-(4-chloro-2-(R,S)-methylsulfinylphenyl) piperidine was prepared according to the procedures described in Example 2 except 3-chlorophenol was used in place of 3-methoxyphenol. The oxidation of the thiomethyl adduct was carried out according to the procedure described in Example 16, sub-part (e). 3-Chlorophenol (24.28 g) was reacted with bromine (29.78 g) to give 6.15 g of 2-bromo-5-chlorophenol (minor isomer) and 24.60 g 4-bromo-3-chlorophenol (major isomer) after purification by column chromatography (10:1 hexane:EtOAc); minor isomer-$^1$H NMR (CDCl$_3$) δ 7.37 (d, 1H), 7.04 (d, 1H), 6.82 (dd, 1H), 5.55 (s, 1H). Major isomer: $^1$H NMR (CDCl$_3$) δ 7.36 (d, 1H), 6.91 (d, 1H), 6.57 (dd, 1H), 5.75 (s, 1H). Analytical data for all other intermediates follows. 2-Bromo-5-chloro-(N,N-dimethylthiocarbamoyl)phenol; $^1$H NMR (CDCl$_3$) δ 7.52 (d, 1H), 7.18 (d, 1H), 7.13 (dd, 1H), 3.47 (s, 3H), 3.39 (s, 3H); MS m/z 296 (M+). 4-Chloro-2-N,N-dimethylthiocarbamoyl)bromobenzene; $^1$H NMR (CDCl$_3$) δ 7.68–7.55 (m, 2H), 7.23 (dd, 1H), 3.12 (s, 3H), 3.05 (s, 3H); MS m/z 296 (M+). 4-Chloro-2-(thiomethyl)bromobenzene; $^1$H NMR (CDCl$_3$) δ 7.43 (d, 1H), 7.06 (d, 1H), 6.97 (dd, 1H), 2.48 (s, 3H). 1-Benzyloxycarbonyl-4-hydroxy-4-(4-chloro-2-methylthiophenyl)piperidine; $^1$H NMR (CDCl$_3$) δ 7.43–7.30 (m, 6H), 7.26 (d, 1H), 7.15 (dd, 1H) 5.15 (s, 2H), 4.25–4.00 (m, 2H), 3.84 (s, 1H), 3.50–3.25 (m, 2H), 2.52 (s, 3H), 2.15–1.90 (m, 4H); MS m/z 414 (M+Na). 1-Benzyloxycarbonyl-4-(4-chloro-2-methylthiophenyl) piperidine; $^1$H NMR (CDCl$_3$) δ 7.43–7.30 (m, 5H), 7.18–7.10 (m, 3H), 5.16 (s, 2H), 4.42–4.20 (m, 2H), 3.07 (tt, 1H), 3.00–2.80 (m, 2H), 2.47 (s, 3H), 1.91–1.45 (m, 4H); MS m/z 398 (M+Na). 1-Benzyloxycarbonyl-4-(4-chloro-2-(R,S)-methylsulfinylphenyl)piperidine; $^1$H NMR (CDCl$_3$) δ 7.98 (d, 1H), 7.42 (dd, 1H), 7.41–7.30 (m, 5H), 7.21 (d, 1H), 5.16 (s, 2H), 4.43–4.21 (m, 2H), 2.96–2.78 (m, 3H), 2.71 (s, 3H), 1.92–1.51 (m, 4H). 4-(4-Chloro-2-(R,S)-methylsulfinylphenyl)piperidine; $^1$H NMR (CDCl$_3$) δ 7.97 (d, 1H), 7.43 (dd, 1H), 7.28 (d, 1H), 3.30–3.10 (m, 2H), 2.71 (s, 3H), 2.83–2.61 (m, 3H), 1.92–1.51 (m, 5H); MS m/z 258 (M+H).

Example 58

N-[(S)-2-(3,4-Dichlorophenyl)-4-[4-[(S)-2-methylsulfinylphenyl]-1-piperidinyl]butyl]-N-methyl-3-trifluoromethyl-1-naphthamide Citrate Hydrate

Using standard acylation conditions, 3-trifluoromethyl-1-naphthoyl chloride (0.11 g) was reacted with N-[(S)-2-(3,4-dichlorophenyl)-4-[4-[(S)-2-methylsulfinylphenyl]-1-piperidinyl]butyl]-N-methylamine (0.19 g), converted to the citrate salt and isolated by filtration from diethyl ether to afford the title compound (0.3 g) as an off-white powder. MS APCI, m/z=675 (M+H); $^1$H NMR (300 MHz, DMSO-$d_6$) δ 11.0 (broad), 8.55–8.40 (m), 8.30–8.10 (m), 7.91–7.63 (m), 7.62–7.45 (m), 7.44–7.12 (m), 7.05–6.85 (m), 3.20–2.76 (m), 2.75–2.55 (m), 2.20–1.65 (m); analysis calculated for $C_{35}H_{35}Cl_2F_3N_2O_2S$, 1 $C_6H_8O_7$, 1 $H_2O$, C 55.60, H 5.12, N 3.16, found C 55.42, H 5.02, N 3.12.

The requisite 3-trifluoromethyl-1-naphthoyl chloride was prepared as follows.

a) 4-Bromo-2-naphthoic acid.

A solution of 4-bromo-2-naphthoic acid, methyl ester (Adcock, W; Wells, PR; Aust. J.Chem.; 18, 1965; 1351–1364) (2.23 g) in THF (50 mL) was treated with a solution of LiOH (hydrate) (0.39 g) and $H_2O$ (25 mL). Methanol (5 mL) was added, and the mixture was stirred at 25° C. for several days. The mixture was concentrated in vacuo, treated with additional $H_2O$, washed with diethyl ether, acidified (10% aq. HCl), and extracted with a mixture of EtOAc and DCM (1:2). The extracts were dried $Na_2SO_4$), filtered, and the solvent removed in vacuo. The off-white solid residue was triturated with diethyl ether, the solids recovered by filtration, washed with minimum diethyl ether, and dried under reduced pressure to afford the product (1.6 g, 76%) as an off-white solid. MS EI, m/z=250 (M); $^1$H NMR (300 MHz DMSO-$d_6$) δ 13.44 (bs, 1H), 8.68 (s, 1H), 8.25 (s, 1H), 8.23–8.18 (m, 2H), 7.87–7.83 (t, 1H), 7.76–7.71 (t, 1H).

b) 4-Bromo-2-thionaphthoic acid, S-ethyl ester.

A mixture containing 4-bromo-2-naphthoic acid (1.34 g) and dry DCM (15 mL) was treated with oxalyl chloride (0.83 g) at 25° C. A catalytic amount of DMF was added, the mixture stirred for 4 hours, then the DCM removed in vacuo. The solid residue was redissolved in dry DCM (15 mL), cooled (ice bath), and ethanethiol (0.85 mL) was added dropwise. After 10 minutes, TEA (1.6 mL) was added, and the mixture was allowed to warm to 25° C. After stirring for 16 hrs., the mixture was diluted with 10% aq. NaHCO$_3$ and extracted with DCM. The extracts were dried ($Na_2SO_4$), filtered, and the solvent removed in vacuo. The dark, red-orange residue was purified by chromatography (10% $CH_2Cl_2$ in hexane) to afford the product (1.51 g, 96.2%) as an off-white solid. MS EI, m/z=294/296 (M); $^1$H NMR (300 MHz, CDCl$_3$) δ 8.48 (s, 1H), 8.30 (s, 1H), 8.28–8.25 (d, 1H), 7.99–7.96 (d, 1H), 7.75–7.70 (t, 1H), 7.64–7.59 (t, 1H), 3.18–3.11 (q, 2H), 1.42–1.37 (t, 3H).

c) 4-Bromo-2-dithionaphthoic acid, ethyl ester.

A mixture containing 4-bromo-2-thionaphthoic acid, S-ethyl ester (1.49 g), 2,4-bis(4-methoxyphenyl)-1,3-dithia-2,4-diphosphetane-2,4-disulfide (Lawesson's reagent) (1.43 g), and dry toluene (25 mL) was heated under reflux for 20 hours, allowed to cool, then diluted with diethyl ether. The solution was washed [aq. NaHCO$_3$ and $H_2O$], dried ($Na_2SO_4$), filtered, and the solvent removed in vacuo. The dark-red residue was purified by chromatography (10% $CH_2Cl_2$ in hexane) to afford the product (1.35 g) (85.6%) as a red solid. MS EI, m/z=310/312 (M); $^1$H NMR (300 MHz, CDCl$_3$) δ 8.47 (s, 1H), 8.44 (s, 1H), 8.24–8.22 (d, 1H), 7.97–7.95 (d, 1H), 7.71–7.67 (t, 1H), 7.61–7.57 (t, 1H), 3.46–3.39 (q, 2H), 1.48–1.43 (t, 3H).

d) 1-Bromo-3-trifluoromethylnaphthalene.

Based on the procedure of Kuroboshi, M and Hiyama, T (Chemistry Letters, 827–830 (1992), a solution containing 4-bromo-2-dithionaphthoic acid, ethyl ester (0.18 g) and dry DCM (4 mL) was cooled (0° C.) and treated with HF/pyridine (70:30 wt %) (0.6 mL). After several minutes, 1,3-dibromo-5,5-dimethylhydantoin (0.68 g) was added in one portion. The reaction was allowed to warm to 25° C., stirred for 1.5 hours, poured into a solution of sat. aq. NaHCO$_3$ and NaHSO$_3$, and extracted with diethyl ether. The diethyl ether extracts were dried (Na$_2$SO$_4$), filtered, the solvent removed in vacuo. The residue was purified by chromatography (hexane) to afford the product (0.08 g, 50%) as a colorless liquid. MS EI, m/z=274/276 (M); $^1$H NMR (300 MHz, CDCl$_3$) δ 8.31 –8.28 (d, 1H), 8.13 (s, 1H), 7.96–7.93 (s,d, 2H), 7.77–7.72 (t, 1H), 7.68–7.63 (t, 1H); $^{19}$F NMR (282 MHz, CDCl$_3$) δ –62.91 (s).

e) 3-Trifluoromethyl-1-naphthoic acid, methyl ester

A mixture containing 1-bromo-3-trifluoromethylnaphthalene (0.44 g), 1,3-bis(diphenylphosphino)propane (0.13 g), palladium acetate (0.08 g), and TEA (0.45 mL) in DMSO (10 mL) and MeOH (10 mL) was placed under an atmosphere of carbon monoxide. The mixture was heated at 70° C. for 22 hours, cooled, diluted with MeOH, filtered through celite, and rinsed with MeOH. The combined filtrates and washings were evaporated in vacuo. The residue was dissolved in EtOAc, washed (with water and brine), dried (Na$_2$SO$_4$), filtered, and the solvent removed in vacuo. The residue was purified by chromatography (10% DCM in hexane) to afford the product (0.24 g) (58.6%) as a colorless liquid. MS EI, m/z=254 (M); $^1$H NMR (300 MHz, CDCl$_3$) δ 8.99–8.97 (d, 1H), 8.36 (s, 1H), 8.32 (s, 1H), 8.00–9–7.97 (d, 1H), 7.78–7.72 (t, 1H), 7.67–7.63 (t, 1H), 4.04 (s, 3H); $^{19}$F NMR (282 MHz, CDCl$_3$) δ –60.42 (s).

f) 3-Trifluoromethyl-1-naphthoic acid

A solution of 3-trifluoromethyl-1-naphthoic acid, methyl ester (0.23 g) in THF (5 mL) was treated with a solution of LiOH (hydrate) (0.044 g) and H$_2$O (1.5 mL). Methanol (0.5 mL) was added, and the mixture was stirred at 25° C. for 3.5 hours. The mixture was concentrated in vacuo, treated with additional H$_2$O, acidified (1N aq. HCl), and extracted with DCM. The extracts were dried (anhyd. Na$_2$SO$_4$), filtered, and the solvent removed in vacuo to afford the product (0.21 g) (95.8%) as an off-white solid. MS EI, m/z=240 (M); $^1$H NMR (300 MHz, CDCl$_3$) δ 9.14–9.12 (d, 1H), 8.58 (s, 1H), 8.40 (s, 1H), 8.05–8.02 (d, 1H), 7.83–7.78 (t, 1H), 7.71–7.66 (t, 1H); $^{19}$F NMR (376 MHz, CDCl$_3$) δ –61.53 (s).

g) 3-Trifluoromethyl-1-naphthoyl chloride

A mixture containing 3-trifluoromethyl-1-naphthoic acid (0.10 g) and dry DCM (5 mL) was treated with oxalyl chloride (0.065 g) at 25° C. A catalytic amount of DMF was added, the mixture stirred for 4 hours, then the DCM was removed in vacuo. The solid residue was re-dissolved in dry DCM and used without further purification.

Example 59

N-[2-(S)-(3,4-Dichlorophenyl)-4-[4-[4-(R,S)-(methylsulfinyl)phenyl]-1-piperidinyl]butyl]-N-methyl-3-cyano-1-naphthamide Hydrochloride Using standard reductive amination conditions N-[2-(S)-(3,4-dichlorophenyl)]-4-oxobutyl-N-methyl-3-cyano-1-naphthamide (0.150 g) was reacted with 4-(4-(R,S)-methylsulfinylphenyl)piperidine (0.079 g) and converted to the hydrochloride salt. MS m/z 632 (M+). $^1$H NMR (DMSO d$_6$) δ 10.49 (m, 1H), 8.63 (m, 1H), 8.10 (m, 1H), 7.90–6.50 (m, 10H), 2.73 (s, 3H), 3.77–1.70 (m, 19H).

Example 60

N-[(S)-2-(3,4-Dichlorophenyl)-4-[4-[3-fluoro-4-methylsulfinylphenyl]-1-piperidinyl]butyl]-N-methyl-3-cyano-1-naphthamide Using standard reductive amination conditions N-[2-(S)-(3,4-dichlorophenyl)]-4-oxobutyl-N-methyl-3-cyano-1-naphthamide (0.213 g) was reacted with 4-(3-fluoro-4-methylsulfinylphenyl)piperidine (0.120 g) and converted to the hydrochloride salt (0.276 g). mp 175–180° C.; $^1$H NMR (300 MHz, CDCl$_3$) δ 10.76 (m, 1H), 8.63 (s, 1H), 8.25 (m, 1H), 7.9–6.9 (m, 9H), 6.5 (br., 1H), 4.5 (br., 1H), 2.82 (two peaks, 3H), 2.5 (two peaks, 3H), 2.4–1.8 (m, 6H); MS APCI, m/z=650 (M$^+$).

The requisite N-[(S)-2-(3,4-dichlorophenyl)-4-[4-[3-fluoro-4-methylsulfinylphenyl]-1-piperidinyl]butyl]-N-methylamine was prepared from 4-bromo-2-fluorophenol using procedures according to those described in Example 2a-h for 4-(4-methoxy-2-methylsulfinylphenyl)piperidine except for the oxidation (step g) of the intermediate 4-(3-fluoro-4-methylthiophenyl)-N-Cbz-piperidine; this was carried out as described in Example 16e and the cleavage of the Cbz-group (step h) which was carried out as described in Example 6c. $^1$H NMR (300 MHz, CDCl$_3$) δ 8.8 (t, J=10 Hz, 1H) 7.3 (m, 1H), 6.97 (m, 1H), 3.3 (m, 2H), 1.85 (m, 2H), 1.65 (m, 2H); MS APCI, m/z=242 (M$^+$);

Example 61

N-[(S)-2-(3,4-Dichlorophenyl)-4-[4-[4-methylsulfonyloxyphenyl]-1-piperidinyl]butyl]-N-methyl-3-cyano-1-naphthamide To a stirred solution of N-[(S)-2-(3,4-dichlorophenyl)-4-[4-[2-hydroxyphenyl]-1-piperidinyl]butyl]-N-methyl-3-cyano-1-naphthamide (100 mg) in DCM (2 mL) at 0° C. was added triethylamine (0.030 mL) and methanesulfonyl chloride (0.016 ml). The stirred solution was warmed to room temperature over 2 h. additional triethylamine (two drops) and methanesulfonyl chloride (1 drop) were added, stirring continued for 30 min, and the mixture was concentrated and purified by chromatography (5–10% MeOH in DCM (110 mg). $^1$H NMR (300 MHz, DMSO-d$_6$) δ 8.64 (d,1H); 8.10 (m,1H); 6.40–7.90 (m); 4.10 (bs); 3.50 (d,3H); 2.40–3.45 (m); 2.13 (m); 1.60–2.00 (m); MS APCI, m/z=664 (M$^+$).

The requisite N-[(S)-2-(3,4-dichlorophenyl)-4-[4-[2-hydroxyphenyl]-1-piperidinyl]butyl]-N-methyl-3-cyano-1-naphthamide was prepared as follows.

2-Benzyloxybromobenzene (242.3 g) was reacted with 1-benzyloxycarbonyl-4-piperidone (214.7 g) according to the method described for Example 2e to afford 4-hydroxy-4-(2-benzyloxyphenyl)-N-Cbz-piperidine (226.75 g) after extraction and chromatography using 10–30% ethyl acetate in hexanes. $^1$H NMR (300 MHz, CDCl$_3$) δ 7.40–7.21 (m, 12H), 6.98 (m, 2H), 5.12 (s, 4H), 4.11 (br s, 3H), 3.35 (br s, 2H), 2.03 (br s, 4H). A sample of this material (235 g) was reacted with triethylsilane (405 mL) and trifluoroacetic acid (195 mL) according to the method described for Example 2f. Following extraction and chromatography (10–25% ethyl acetate in hexane), residual triethylsilane was removed by distillation (50–60° C., 800–900 millitorr) to afford 4-(2-benzyloxyphenyl)-N-Cbz-piperidine (179.3 g). A solution of this material (4.01 g) in ethanol (60 mL) was shaken for 24 h with palladium hydroxide on carbon [Pearlman's catalyst] (2.2 g) under hydrogen (50 psi). The catalyst was removed by filtration, the filtrate was concentrated and triturated with acetone to afford 4-(2-hydroxyphenyl)-piperidine (0.75 g) as a white powder. $^1$H NMR (300 MHz, DMSO-d$_6$) δ 8.49 (s, 1H), 7.02 (m, 2H), 6.82 (d, 1H), 6.72 (t, 1H), 3.20 (br d, 2H), 3.02 (m, 1H), 2.85 (tt, 2H), 1.74 (m, 4H). Using standard reductive amination conditions N-[2-(S)-(3,4-dichlorophenyl)]-4-oxobutyl-N-methyl-3-cyano-1-naphthamide (0.213 g) was reacted with 4-(2-hydroxyphenyl)-piperidine to afford N-[(S)-2-(3,4- dichlorophenyl)-4-[4-[2-hydroxyphenyl]-1-piperidinyl]butyl]-N-methyl-3-cyano-1-naphthamide.

Example 62

N-[2-(S)-(3,4-Dichlorophenyl)-4-[4-[3-methoxy-4-(R,S)-methylsulfinylphenyl]-1-piperidinyl]butyl]-N-methyl-3-cyano-1-naphthamide Hydrochloride Using standard reductive alkylation conditions N-[2-(S)-(3,4-dichlorophenyl)]-4-oxobutyl-N-methyl-3-cyano-1-naphthamide (0.128 g) was reacted with 4-(3-methoxy-4-(R,S)-methylsulfinylphenyl)piperidine (0.080 g) and converted to the hydrochloride salt. MS m/z 662 (M+). $^1$H NMR (DMSO d$_6$) δ 10.30 (m, 1H), 8.63 (m, 1H), 8.10 (m, 1H), 7.90–6.85 (m, 10H), 3.86 (s, 3H), 3.35 (s, 3H), 2.68 (s, 3H), 3.77–1.78 (m, 16H).

The requisite 4-(3-methoxy-4-(R,S)-(methylsulfinylphenyl)piperidine was prepared according to the procedures described for Example 2, except 2-methoxyphenol was used in place of 3-methoxyphenol. Abbreviated protocols and analytical data follow.

4-Bromo-2-methoxyphenol: 2-methoxyphenol (129.03 g) (used in place of 3-methoxyphenol according to Example 2) was reacted with bromine (167.94 g) to give 161.78 g of product after purification by vacuum distillation. $^1$H NMR (CDCl$_3$) δ 7.10–6.90 (m, 2H), 6.78 (d, 1H), 5.66 (s, 1H), 3.84 (s, 3H). 4-Bromo-2-methoxy-(N,N-dimethylthiocarbamoyl)phenol: 4-bromo-2-methoxyphenol (20.45 g) was reacted with N,N-dimethylthiocarbamoyl chloride (15.75 g) to give 18.28 g of product after recrystallization from MeOH. MS m/z 290 (M+). $^1$H NMR (CDCl$_3$) δ 7.18–7.09 (m, 2H), 6.90 (d, 1H), 3.82 (s, 3H), 3.45 (s, 3H), 3.35 (s, 3H). 5-Bromo-2-(N,N-dimethylthiocarbamoyl)methoxybenzene: 4-bromo-2-methoxy-(N,N-dimethylthiocarbamoyl)phenol (18.28 g) was rearranged to give 13.81 g of product after recrystallization from MeOH. MS m/z 290 (M+). $^1$H NMR (CDCl$_3$) δ 7.31 (d, 1H), 7.19–7.05 (m, 2H), 3.87 (s, 3H), 3.12 (br s, 3H), 3.01 (br s, 3H). 5-Bromo-2-(thiomethyl)methoxybenzene: 5-bromo-2-(N,N-dimethylthiocarbamoyl)methoxybenzene (13.81 g) was hydrolyzed and methylated to give 10.71 g of product. $^1$H NMR (CDCl$_3$) δ 7.09 (dd, 1H), 6.99 (d, 1H), 6.95 (d, 1H), 3.89 (s, 3H), 2.41 (s, 3H). 1-Benzyloxycarbonyl-4-hydroxy-4-(3-methoxy-4-methylthiophenyl)piperidine: 5-bromo-2-(thiomethyl)methoxybenzene (5.49 g) was reacted with 1-benzyloxycarbonyl-4-piperidone (5.72 g) to give 4.50 g of an oil after chromatography (1:1 EtOAc:hexane). MS m/z 410 (M+Na). $^1$H NMR (CDCl$_3$) δ 7.43–7.30 (m, 5H), 7.21–6.92 (m, 3H), 5.16 (s, 2H), 4.30–4.10 (m, 2H), 3.90 (s, 3H), 3.31–3.20 (m, 2H), 2.44 (s, 3H), 2.13–1.60 (m, 4H). 1-Benzyloxycarbonyl-4-(3-methoxy-4-methylthiophenyl)piperidine: 1-benzyloxycarbonyl-4-hydroxy- 4-(3-methoxy-4-methylthiophenyl)piperidine (4.50 g) was reduced to yield 3.22 g of an oil after chromatography (20:1 DCM:EtOAc). $^1$H NMR (CDCl$_3$) δ 7.43–7.30 (m, 5H), 7.13 (d, 1H), 6.79 (dd, 1H), 6.67 (d, 1H), 5.16 (s, 2H), 4.35–4.20 (m, 2H), 3.88 (s, 3H), 2.96–2.72 (m, 2H), 2.62 (tt, 1H), 2.42 (s, 3H), 1.91–1.50 (m, 4H). 1-Benzyloxycarbonyl-4-(3-methoxy-4-(R,S)-methylsulfinylphenyl)piperidine: To a stirred solution of NaIO$_4$ (2.06 g) dissolved in 40 mL 1:1 THF:H$_2$O was added 1-benzyloxycarbonyl-4-(3-methoxy-4-methylthiophenyl)piperidine (1.23 g). The mixture was stirred at room temperature for 18 h, poured into 60 mL H$_2$O, and extracted with DCM (3×40 mL). Organic extracts were combined, dried over Na$_2$SO4, and evaporated to give 0.94 g of an oil after chromatography (20:1 DCM:EtOAc). $^1$H NMR (CDCl$_3$) δ 7.74 (d, 1H), 7.47–7.30 (m, 5H), 7.02 (dd, 1H), 6.73 (d, 1H), 5.16 (s, 2H), 4.35–4.20 (m, 2H), 3.88 (s, 3H), 2.98–2.78 (m, 2H), 2.76 (s, 3H), 2.73 (tt, 1H), 1.95–1.55 (m, 4H). 4-(3-methoxy-4-(R,S)-methylsulfinylphenyl)piperidine: 1-benzyloxycarbonyl-4-(3-methoxy-4-(R,S)-methylsulfinylphenyl)piperidine (0.94 g) was hydrolyzed to give 0.52 g of a white solid after chromatography (10:1 DCM:MeOH w/0.5% aq. NH$_3$). MS m/z 254 (M+H). $^1$H NMR (CDCl$_3$) δ 7.73 (d, 1H), 7.05 (dd, 1H), 6.79 (d, 1H), 3.88 (s, 3H), 3.35–3.20 (m, 2H), 2.90–2.60 (m, 3H), 2.77 (s, 3H), 1.95–1.61 (m, 4H).

Example 63

N-[(S)-2-(3,4-Dichlorophenyl)-4-[4-[2-[2-oxopyrrolidinylphenyl]-1-piperidinyl]butyl]-N-methyl-3-cyano-1-naphthamide Citrate Using the reductive amination conditions described in Example 20c, 4-(2-oxopyrrolidinylphenyl)piperidine was reacted with N-[2-(S)-(3,4-dichlorophenyl)]-4-oxobutyl-N-methyl-3-cyano-1-naphthamide, the product was converted to the citrate salt and recovered as a white powder. MS: m/z=653 (M+H). $^1$H NMR (DMSO d$_6$, selected resonances) δ 8.6 (m, 1H), 8.1 (m, 1H), 7.90–6.80 (m, 11H), 2.50 (s, 3H, CO—N—CH$_3$). Analysis calculated for $C_{38}H_{38}N_4O_2Cl_2$, 2.8 H$_2$O, 1.0 citric acid, C 58.97, H 5.80, N 6.25, found C 58.89, H 5.50, N 6.16.

The requisite 4-(2-oxopyrrolidinylphenyl)piperidine was prepared as follows.

a) Methyl 3-[N-(2-{1-[tert-butyloxycarbonyl]-4-piperidyl}phenyl)carbamoyl]propanoate.

3-Carbomethoxypropionyl chloride (0.120 g) was added to a solution of tert-butyl 4-(2-aminophenyl)piperidinecarboxylate (0.211 g) (Example 21) and triethylamine (0.081 g) in DCM (10 mL) and stirred at ambient temperature overnight. The reaction was diluted with 1N aqueous HCl. The organic phase was dried and evaporated to give the title compound (0.310 g)as a yellow oil. MS: m/z=291 (M-Boc). $^1$H NMR (CDCl$_3$) δ 7.53 (m, 1H), 7.19 (m, 3H), 4.25 (br, 1H, NH), 3.72 (s, 3H), 2.82–2.64 (m, 6H), 1.78–1.39 (m, 7H), 1.54 (s, 9H).

b) Methyl 4-[(2-{1-[tert-butyloxycarbonyl]-4-piperidyl}phenyl)amino]butanoate.

A solution of borane in tetrahydrofuran (1M, 3 mL) was added to methyl 3-[N-(2-{1-[tert-butyloxycarbonyl]-4-piperidyl}phenyl)carbamoyl]propanoate (0.298 g) dissolved in tetrahydrofuran (12 mL) under nitrogen. The mixture was heated at reflux for 2 h. cooled to room temperature, 1N aqueous HCl (5 mL) added and stirred for an additional 15 min. The solution was partially concentrated, diluted with aqueous potassium carbonate and extracted with ethyl acetate. The organic extracts were dried and evaporated and the residue purified by chromatography, (4:1 hexanes:ethyl acetate) to give the title compound (0.110 g) as a yellow oil. MS: m/z=277 (M-Boc). $^1$H NMR (CDCl$_3$) δ 7.11 (m, 3H), 6.72 (m, 2H), 4.27 (br, 1H, NH), 3.69 (s, 3H, OCH$_3$), 3.20 (m, 2H), 2.83 (m, 2H), 2.46 (m, 3H), 2.05 (m, 2H), 1.84 (m, 3H), 1.69 (m, 2H), 1.54 (s, 9H).

c) 4-[(2-{1-[tert-Butyloxycarbonyl]-4-piperidyl}phenyl)amino]butanoic acid.

1N aqueous sodium hydroxide (0.5 mL) and methanol (0.5 mL) were added to a solution of methyl 4-[(2-{1-[tert-butyloxycarbonyl]-4-piperidyl}phenyl)amino]butanoate (0.110 g) in tetrahydrofuran (3 mL) and the mixture stirred for 3 hours. The reaction was diluted with 1N aqueous HCl and extracted with DCM. The organic extracts were dried and evaporated to give the title compound (0.100 g) as a yellow oil. MS: m/z=363 (M+H).

d) 1-(2-(4-Piperidyl)phenyl)pyrrolidin-2-one hydrochloride.

Diisopropylethyl amine (0.065 g), 1-hydroxybenzotriazole (0.040 g) and N-(3-dimethylaminopropyl)-N'-ethylcarbodiimide hydrochloride (0.096 g) were added to 4-[(2-{1-[tert-butyloxycarbonyl]-4-piperidyl}phenyl)amino]butanoic acid hydrochloride (0.100 g) in DCM (6 mL) and the mixture stirred overnight. The reaction was diluted with 1N aqueous HCl and extracted with DCM. The organic extracts were dried and evaporated to give the title compound (0.100 g) as a yellow oil. MS: m/z=367 (M+Na), 245 (M-Boc). This material was N-deprotected with HCl using the conditions described for Example 21d to afford 1-(2-(4-piperidyl)phenyl)pyrrolidin-2-one hydrochloride. MS: m/z=245 (M+H).

Example 64

N-[(S)-2-(3,4-Dichlorophenyl)-4-[4-[2-(N-oxo-N,N-dimethylamino)phenyl]-1-piperidinyl]butyl]-N-methyl-3-cyano-1-naphthamide Citrate Using the reductive amination conditions described in Example 20c, 4-(2-(N-oxo-N,N-dimethylamino)phenylpiperidine was reacted with N-[2-(S)-(3,4-dichlorophenyl)]-4-oxobutyl-N-methyl-3-cyano-1-naphthamide, the product was converted to the citrate salt and recovered as a white powder. MS: m/z=629 (M+H). $^1$H NMR (DMSO $d_6$, selected resonances) δ 8.6 (m, 1H), 8.1 (m, 1H), 7.90–6.80 (m, 11H), 3.83 (s, 6H, Ar—N(O)CH$_3$), 2.50 (s, 3H, CO—N—CH$_3$).

The requisite 4-(2-(N-oxo-N,N-dimethylamino)phenyl)piperidine was prepared as follows.
a) 4-[2-(N-oxo-N,N-dimethylamino)phenyl]piperidine hydrochloride.

3-Chloroperoxybenzoic acid (0.125 g) in DCM (2 mL) was added to tert-butyl 4-[2-N,N-dimethylaminophenyl]piperidinecarboxylate (0.220 g) in DCM (10 mL) and stirred for 1 hour. The reaction mixture was extracted sequentially with aqueous sodium sulfite and aqueous sodium bicarbonate. The organic phase was dried and evaporated to give tert-butyl 4-[2-(N-oxo-N,N-dimethylamino)phenyl]piperidinecarboxylate (0.206 g) as a foamy white solid. MS: m/z=321 (M+H). This material was N-deprotected with HCl according to the conditions described for Example 21d, to afford 4-[2-(N-oxo-N,N-dimethylamino)phenyl]piperidine hydrochloride which was used without purification.

Example 65

N-[(S)-2-(3,4-Dichlorophenyl)-4-[4-[2-methoxycarbonylaminophenyl]-1-piperidinyl]butyl]-N-methyl-3-cyano-1-naphthamide Citrate Using the reductive amination conditions described in Example 20c, 4-(2-methoxycarbonylaminophenyl)piperidine was reacted with N-[2-(S)-(3,4-dichlorophenyl)]-4-oxobutyl-N-methyl-3-cyano-1-naphthamide, the product was converted to the citrate salt and recovered as a white powder. MS: m/z=643 (M+H). $^1$H NMR (DMSO $d_6$, selected resonances) δ 8.91 (m, 1H), 8.64 (m, 1H), 8.12 (m, 1H), 7.90–6.80 (m, 10H), 6.30 (br, 1H, NH), 3.77 (s, 3H, OCH$_3$), 2.50 (s, 3H, CO—N—CH$_3$).

The requisite 4-(2-methoxycarbonylaminophenyl)piperidine was prepared as follows.

Methyl chloroformate (0.065 g) was added to a solution of tert-butyl 4-(2-aminophenyl)piperidine carboxylate (0.172 g) (Example 21) and triethylamine in DCM (4 mL) and stirred overnight then diluted with 1N aqueous HCl. The organic phase was dried and evaporated to give tert-butyl 4-(2-methoxycarbonylaminophenyl)piperidinecarboxylate (0.207 g) as an oil. MS: m/z=235 (M-Boc). $^1$H NMR (CDCl$_3$) δ 7.21 (m, 4H), 6.30 (br, 1H, NH), 4.24 (m, 2H), 3.72 (s, 3H, OCH$_3$), 2.77 (m, 3H), 1.67 (m, 4h), 1.49 (s, 9H). This material was N-deprotected with HCl according to the procedure of Example 21d, to afford 4-(2-methoxycarbonylaminophenyl)piperidine hydrochloride.

Example 66

N-[(S)-2-(3,4-Dichlorophenyl)-4-[4-[2-(methoxy-1,2-dioxoethylamino)phenyl]-1-piperidinyl]butyl]-N-methyl-3-cyano-1-naphthamide Citrate Using the reductive amination conditions described in Example 20c, 4-(2-(methoxy-1,2-dioxoethylamino)phenyl)piperidine was reacted with N-[2-(S)-(3,4-dichlorophenyl)]-4-oxobutyl-N-methyl-3-cyano-1-naphthamide, the product was converted to the citrate salt and recovered as a white powder. MS: m/z=671 (M+H). $^1$H NMR (DMSO $d_6$, selected resonances) δ 8.62 (m, 1H), 8.10 (m, 1H), 7.90–6.80 (m, 11H), 6.45 (br, 1H, NH), 3.84 (s, 3H, OCH$_3$), 2.50 (s, 3H, CO—N—CH$_3$).

The requisite 4-(2-(methoxy-1,2-dioxoethylamino)phenyl)piperidine was prepared as follows. According to the procedure described for Example 65, tert-butyl 4-(2-aminophenyl)-piperidine carboxylate was reacted with methyl oxalylchloride (in place of methyl chloroformate) to afford tert-butyl 4-(2-(methoxy-1,2-dioxoethylamino)phenyl)piperidine. MS: m/z=362 (M+H). $^1$H NMR (CDCl$_3$) δ 7.83 (m, 1H), 7.21 (m, 3H), 6.30 (br, 1H, NH), 4.24 (m, 2H), 3.72 (s, 3H, OCH$_3$), 2.77 (m, 3H), 1.67 (m, 4h), 1.51 (s, 9H). This material was N-deprotected using HCl according to the procedure described for Example 21d to afford 4-(2-(methoxy-1,2-dioxoethylamino)phenyl)piperidine.

Example 67

N-[(S)-2-(3,4-Dichlorophenyl)-4-[2-(N,N-dimethylcarbamoylmethoxy)phenyl]-1-piperidinyl]butyl]-N-methyl-3-cyano-1-naphthamide Citrate Using the reductive amination conditions described in Example 20c, 4-[2-(N,N-dimethylcarbamoylmethoxy)phenyl]piperidine was reacted with N-[2-(S)-(3,4-dichlorophenyl)]-4-oxobutyl-N-methyl-3-cyano-1-naphthamide the product was converted to the citrate salt and recovered as a white powder. MS: m/z=671 (M+H). $^1$H NMR (DMSO $d_6$, selected resonances) δ 8.62 (m, 1H), 8.10 (m, 1H), 7.90–6.80 (m, 11H), 4.83 (s, 2H), 4.10 (m, 1H), 2.50 (s, 3H, CO—N—CH$_3$).

The requisite 4-[2-(N,N-dimethylcarbamoylmethoxy)phenyl]piperidine was prepared as follows.
a) Benzyl 4-[2-(methoxycarbonylmethoxy)phenyl]piperidinecarbamate.

Potassium carbonate (0.300 g) and methyl bromoacetate (0.300 g) were added to a solution of 1-benzyloxycarbonyl-4-(2-hydroxyphenyl)piperidine (0.544 g) in acetone (15 mL) and the mixture was heated under reflux for 48 h. The reaction was filtered, evaporated and the residue purified by chromatography, (3:1 hexanes:ethyl acetate) to give benzyl 4-[2-(methoxycarbonylmethoxy)phenyl]piperidinecarbamate (0.825 g) as a yellow oil. MS: m/z=384 (M+H). $^1$H NMR (CDCl$_3$) δ 7.62–6.70 (m, 9H, Ar—H), 5.22 (s, 2H, Ph—CH$_2$), 4.70 (s, 2H, O—CH$_2$—CO), 3.79 (s, 3H, OCH$_3$), 3.25 (m,1H), 2.93 (m, 3H), 1.89 (m, 2H), 1.62 (m, 3H).

b) Benzyl 4-[2-(hydroxycarbonylmethoxy)phenyl]piperidinecarbamate.

Benzyl 4-[2-(methoxycarbonylmethoxy)phenyl]piperidinecarbamate (0.825 g) was dissolved in a mixture of tetrahydrofuran (10 mL), methanol (3 mL), and 1N aqueous sodium hydroxide (10 mL) and stirred for 90 min. The reaction was acidified with 1N aqueous HCl and extracted with diethyl ether. The organic phase was dried and evaporated to give the title compound (0.462 g) as a colorless oil. $^1$H NMR (CDCl$_3$) δ 7.62–6.70 (m, 9H, Ar—H), 5.22 (s, 2H, Ph—CH$_2$), 4.70 (s, 2H, O—CH$_2$—CO), 3.25 (m,1H), 2.93 (m, 3H), 1.89 (m, 2H), 1.62 (m, 3H).

c) Benzyl 4-[2-(N,N-dimethylcarbamoylmethoxy)phenyl]piperidinecarbamate.

A 2M solution of oxalyl chloride (1.25 mL) and a catalytic amount of DMF were added to benzyl 4-[2-(hydroxycarbonylmethoxy)phenyl]piperidinecarbamate (0.462 g) in DCM (20 mL) at 0° C. The mixture was warmed to ambient temperature and stirred for 3 h. The reaction was concentrated, the residue re-dissolved in DCM (20 mL). A 1M solution of dimethylamine in tetrahydrofuran (10 mL) was added and stirred 1 h. The reaction was extracted sequentially with 1N aqueous HCl, aqueous sodium bicarbonate and brine. The organic phase was dried and evaporated to give the title compound (0.433 g) as a colorless oil. MS: m/z=397 (M+H). $^1$H NMR (CDCl$_3$) δ 7.62–6.70 (m, 9H, Ar—H), 5.22 (s, 2H, Ph—CH$_2$), 4.70 (s, 2H, O—CH$_2$—CO), 3.25 (m, 1H), 3.10 (s, 3H, N—CH$_3$), 3.03 (s, 3H, N—CH$_3$), 2.94 (m, 3H), 1.89 (m, 2H), 1.62 (m, 3H).

d) 4-[2-(N,N-dimethylcarbamoylmethoxy)phenyl]piperidine hydrochloride.

An ethanol (20 mL) solution of benzyl 4-[2-(N,N-dimethylcarbamoylmethoxy)phenyl]piperidinecarbamate (0.425 g) was N-deprotected by hydrogenation at 1 atm in the presence of 5% palladium on carbon catalyst (0.200 g) for 3 h to give the title compound (0.275 g) as a colorless oil. MS: m/z=263 (M+H). $^1$H NMR (CDCl$_3$) δ 7.25–6.70 (m, 4H, Ar—H), 4.70 (s, 2H, O—CH$_2$—CO), 3.25 (m,1H), 3.10 (s, 3H, N—CH$_3$), 3.03 (s, 3H, N—CH$_3$), 2.94 (m, 3H), 1.89 (m, 2H), 1.62 (m, 3H).

Example 68

N-[(S)-2-(3,4-Dichlorophenyl)-4-[4-[2-methylsulfinylmethylphenyl]-1-piperidinyl]butyl]-N-methyl-3-cyano-1-naphthamide Citrate 30% aqueous hydrogen peroxide (0.015 g) was added to a solution of N-[(S)-2-(3,4-dichlorophenyl)-4-[4-[2-methylthiomethylphenyl]1-piperidinyl]butyl]-N-methyl-3-cyano-1-naphthamide (0.070 g) in acetic acid (2 mL) and the mixture stirred for 30 min. Acetic acid was evaporated, the residue dissolved in ethyl acetate and extracted with aqueous sodium bicarbonate. The organic phase was dried and evaporated and the residue converted to the citrate salt under standard conditions to give the title compound (0.078 g) as a white powder. MS: m/z=646 (M+H). $^1$H NMR (CDCl$_3$, selected resonances) δ 8.21 (m, 1H), 7.90 (m, 1H), 7.95–7.00 (m, 11H), 4.30 (m, 1H, Ar—CH$_2$—S), 3.96 (m, 1H, Ar—CH$_2$—S), 3.22 (s, 3H, S—CH$_3$), 2.51 (s, 3H, N—CH$_3$).

a) tert-Butyl 4-(2-hydroxymethylphenyl)piperidinecarbamate

A 1M borane solution in tetrahydrofuran (6 mL) was added to a solution of tert-butyl 4-(2-hydroxycarbonylphenyl)piperidinecarbamate (0.915 g) (prepared from 4-(2-methoxycarbonylphenyl)piperidine [Example 20] by N-protection using di-tert-butyldicarbonate followed by saponification of the methyl ester with lithium hydroxide) in tetrahydrofuran (20 mL) at 0° C. The reaction was warmed to ambient temperature and stirred overnight. The reaction was quenched with methanol and 1N aqueous HCl then extracted with diethyl ether. The organic phase was separated and extracted sequentially with aqueous sodium bicarbonate and brine. The organic phase was dried and evaporated to give the title compound (0.906 g) as a colorless oil. MS: m/z=192 (M-Boc). $^1$H NMR (CDCl$_3$) δ 7.28 (m, 4H, Ar—H), 4.75 (d, 2H, Ar—CH$_2$—O), 3.05 (m, 1H), 2.83 (m, 3H), 1.70 (m, 5H), 1.49 (s, 9H).

b) tert-Butyl 4-(2-chloromethylphenyl)piperidinecarbamate.

Hexachloroacetone (2.61 g) was added to a solution of triphenylphosphine (0.830 g) and tert-butyl 4-(2-hydroxymethylphenyl)piperidinecarbamate (0.838 g) in toluene (25 mL). The reaction was stirred for 1 h the evaporated. The residue was purified by chromatography (6:1 hexanes:ethyl acetate) to give the title compound (0.867 g) as a colorless oil. MS: m/z=210 (M+H). $^1$H NMR (CDCl$_3$) δ 7.28 (m, 4H, Ar—H), 4.75 (s, 2H, Ar—CH$_2$—Cl), 3.05 (m, 1H), 2.83 (m, 3H), 1.70 (m, 5H), 1.49 (s, 9H).

c) 4-(2-Methylthiomethylphenyl)piperidine.

Sodium thiomethoxide (0.220 g) tetra-n-butylammonium bromide (0.100 g) and tert-butyl 4-(2-chloromethylphenyl)piperidinecarbamate (0.867 g) were combined in acetone (20 mL) under nitrogen and stirred for 6 h, then heated under reflux for 90 min. The reaction was diluted with aqueous sodium bicarbonate and diethyl ether. The organic phase was dried and evaporated and the residue purified by chromatography (6:1 hexanes:ethyl acetate) to give tert-butyl 4-(2-methylthiomethylphenyl)piperidinecarbamate (0.471 g) as a yellow oil. MS: m/z222 (M-Boc). $^1$H NMR (CDCl$_3$) δ 7.18 (m, 4H, Ar—H), 3.68 (s, 2H, Ar—CH$_2$—S), 3.04 (m, 1H), 2.80 (m,3H), 2.04 (s, 3H, S—CH$_3$), 1.70 (m, 5H), 1.49 (s, 9H). This material was N-deprotected with HCl according to the conditions described for Example 21d to afford 4-(2-methylthiomethylphenyl)piperidine. $^1$H NMR (CDC$_{13}$) δ 7.30 (m, 4H, Ar—H), 3.77 (s, 2H), 3.63 (m, 2H), 3.10 (m, 3H), 2.25 (m, 2H), 2.04 (s, 3H, S—CH$_3$), 1.95 (m, 2H).

d) N-[(S)-2-(3,4-Dichlorophenyl)-4-[4-[2-methylthiomethylphenyl]-1-piperidinyl]butyl]-N-methyl-3-cyano-1-naphthamide.

Using the reductive amination conditions described in Example 63, 4-(2-methylthiomethylphenyl)piperidine was reacted with N-[2-(S)-(3,4-dichlorophenyl)]-4-oxobutyl-N-methyl-3-cyano-1-naphthamide, the product was isolated by extraction and used without purification. MS: m/z=630 (M+H).

Example 69

N-[(S)-2-(3,4-Dichlorophenyl)-4-[4-[(S)-2-methylsulfinylphenyl]-1-piperidinyl]butyl]-N-ethyl-3-cyano-1-naphthamide Using standard acylation conditions, 3-cyano-1-naphthoic acid (0.118 g) was converted to the acid chloride and reacted with N-[(S)-2-(3,4-dichlorophenyl)-4-[4-[(S)-2-methylsulfinylphenyl]-1-piperidinyl]butyl]-N-ethylamine (0.336 g) (prepared according to methods described for N-[(S)-2-(3,4-dichlorophenyl)-4-[4-[(S)-2-methylsulfinylphenyl]-1-piperidinyl]butyl]-N-methylamine, except ethyl chloroformate was used in place of acetyl chloride for the amine acylation prior to amide reduction). mp 115–118° C. (dec); $^1$H NMR (300 MHz, DMSO-d$_6$) δ 8.65 (d), 8.10 (m), 7.95–7.15 (m), 6.50 (m), 3.60 (s), 3.25–2.95 (m), 2.95–2.40 (m), 2.40–1.70 (m), 1.35 (m), 0.9 (m); MS APCI, m/z=646 (M$^+$).

Example 70

The following illustrates representative pharmaceutical dosage forms which may be used for the therapeutic or prophylactic administration of a compound of formula I or IX or a pharmaceutically acceptable salt or in vivo hydrolysable ester thereof hereinafter referred to as 'Compound X':

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 5.9 |
| Lactose | 392.9 |
| Sodium lauryl sulphate | 1.2 |
| | 400.0 |

| (iv) Capsule 2 | mg/capsule |
|---|---|
| 'Compound X' | 29.6 |
| Lactose | 331.4 |
| Sodium Lauryl Sulphate | 1.0 |
| | 362.0 |

| (v) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0–7.5) | q.s. |
| Water for injection | q.s. ad 1 mL |

| (vi) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0–7.5) | q.s. |
| Water for injection | q.s. ad 1 mL |

| (vii) Aerosol | |
|---|---|
| 'Compound X' | 1 g |
| HFA 227 or HFA 134A with 5% ethanol | |

It will be appreciated that the above pharmaceutical compositions may be varied according to well-known pharmaceutical techniques to accommodate differing amounts and types of active ingredient 'Compound X'. The aerosol (vii) may be used in conjunction with a standard, metered dose aerosol dispenser.

What is claimed is:

1. A compound of the formula (I):

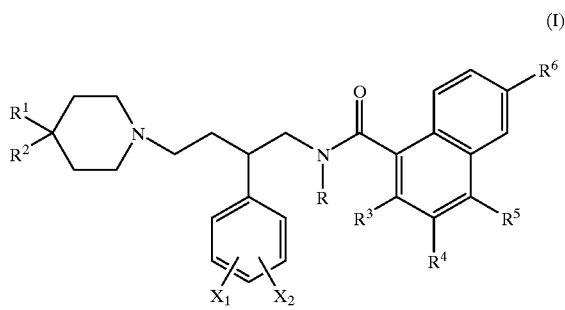

wherein:

R is alkyl;

$R^1$ is optionally substituted phenyl, 2-oxo-tetrahydro-1(2H)-pyrimidinyl, or 2-oxo-1-piperidinyl;

$R^2$ is hydrogen, alkoxy, alkanoyloxy, alkoxycarbonyl, alkanoylamino, acyl, alkyl, carbamoyl, N-alkylcarbamoyl, N,N-dialkylcarbamoyl where the alkyl groups are the same or different, hydroxy, thioacyl, thiocarbamoyl, N-alkylthiocarbamoyl, or N,N-dialkylthiocarbamoyl where the alkyl groups are the same or different;

$X_1$ and $X_2$ are independently hydrogen or halo, provided that at least one of $X_1$ or $X_2$ is halo; and $R^3$, $R^4$, $R^5$, and $R^6$ are independently hydrogen, cyano, nitro, trifluoromethoxy, trifluoromethyl, or alkylsulfonyl, provided that at least one of $R^3$, $R^4$, $R^5$, and $R^6$ is not hydrogen;

or a pharmaceutically acceptable salt or an in vivo hydrolysable precursor thereof.

2. A compound according to claim 1 wherein $R^1$ is phenyl optionally substituted by $C_{1-6}$alkyl, $C_{1-6}$alkylthio; $C_{1-6}$alkylsulfinyl; $C_{1-6}$alkylsulfonyl; $C_{1-6}$alkoxy; hydroxy; amino; halo; carboxy; $C_{1-6}$alkoxycarbonyl; nitro; $C_{1-6}$alkylamino; di-$C_{1-6}$alkylamino; trifluoromethyl; carbamoyl; $C_{1-6}$alkylcarbamoyl; di-$C_{1-6}$alkylcarbamoyl; trifluoromethylthio; trifluoromethylsulfinyl; trifluoromethylsulfonyl; $C_{1-6}$alkanesulfonamido; $C_{1-6}$alkanoyl; N—$C_{1-6}$alkoxy, N—$C_{1-6}$alkylamino; $C_{1-6}$alkanoylamino; ureido; $C_{1-6}$alkylureido; di-$C_{1-6}$alkylureido; $C_{1-6}$alkylsulfonyloxy; 2-oxopyrrolidino; N-oxo-N,N-di-$C_{1-6}$alkylamino; $C_{1-6}$alkoxycarbonylamino; $C_{1-6}$alkoxycarbonylcarbonylamino; $C_{1-6}$alkylcarbamoyl$C_{1-6}$alkoxy; di-$C_{1-6}$alkylcarbamoyl$C_{1-6}$alkoxy; and $C_{1-6}$alkyl substituted by any of the hereinabove substituents.

3. A compound according to claim 1 wherein $R^1$ is a phenyl group substituted in the ortho-position by $C_{1-6}$alkylthio; $C_{1-6}$alkylsulfinyl; $C_{1-6}$alkylsulfonyl; trifluoromethylthio; trifluoromethylsulfinyl; $C_{1-6}$alkanesulfonamido; $C_{1-6}$alkanoyl; $C_{1-6}$alkoxycarbonyl; succinamido; carbamoyl; $C_{1-6}$alkylcarbamoyl; di-$C_{1-6}$alkylcarbamoyl; $C_{1-6}$alkoxy; $C_{1-6}$alkylcarbamoyl; $C_{1-6}$alkanoylamino; ureido; $C_{1-6}$alkylureido, di-$C_{1-6}$alkylureido; amino; $C_{1-6}$alkylamino or di-$C_{1-6}$alkylamino and optionally is further substituted.

4. A compound according to claim 1 wherein $R^1$ is phenyl substituted in the ortho-position by methylsulfinyl, methylsulfonyl, methylureido, dimethylureido, amino, methylamino or dimethylamino.

5. A compound according to claim 1 wherein $R^1$ is:

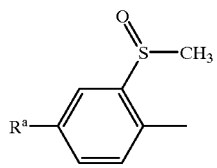

(Ia)

wherein $R^a$ is hydrogen, $C_{1-6}$alkoxy, halo, $C_{1-6}$alkylsulfinyl or carboxy.

6. A compound according to claim 1 wherein $R^1$ is phenyl and any orthoethylsulfinyl substituent has the (S)-configuration.

7. A compound according to claim 1 wherein $R^1$ is 2-oxotetrahydro-1(2H)-pyrimidinyl.

8. A compound according to claim 1 wherein $R^1$ is 2-oxo-1-piperidinyl.

9. A compound according to claim 1 wherein $R^2$ is hydrogen.

10. A compound according to claim 1 which is:

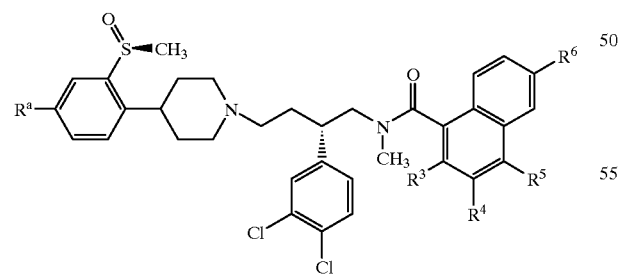

wherein $R^a$ is hydrogen, $C_{1-6}$alkoxy, halo, $C_{1-6}$alkylsulfinyl or carboxy; $R^3$ is hydrogen; $R^4$ is cyano or nitro; $R^5$ is hydrogen or cyano; and $R^6$ is hydrogen.

11. N-[(S)-2-(3,4-Dichlorophenyl)-4-[4-[(S)-2-methylsulfinylphenyl]-1-piperidinyl]butyl]-N-methyl-3-cyano-1-naphthamide or a pharmaceutically acceptable salt thereof.

12. N-[(S)-2-(3,4-Dichlorophenyl)-4-[4-{4-methoxy-(S)-2-methylsulfinylphenyl}-1-piperidinyl]butyl]-N-methyl-3-cyano-1-naphthamide or a pharmaceutically acceptable salt thereof.

13. A compound of the formula (IX):

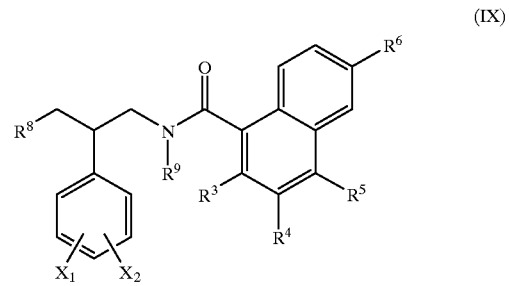

(IX)

wherein $R^9$ is hydrogen or a group R as defined in claim 1, $X_1$, $X_2$ and $R^3$–$R^6$ are as defined in claim 1; and $R^8$ is —CHO, —$CH_2OR^{10}$ wherein $R^{10}$ is hydrogen or an ester thereof or $C_{1-6}$alkyl, or a pharmaceutically acceptable salt or in vivo hydrolysable precursor thereof.

14. A compound according to claim 1 in the form of a base or pharmaceutically acceptable salt wherein R is methyl.

15. A pharmaceutical composition which comprises a compound according to claim 1 and a pharmaceutically acceptable carrier.

16. A method of treating a disease condition wherein antagonism of at least one tachykinin receptor is beneficial which comprises administering to a patient in need thereof an effective amount of a compound according to claim 1.

17. A process for preparing a compound of the formula (I) or a pharmaceutically acceptable salt or an in vivo hydrolysable precursor thereof which process comprises:

a) reacting a compound of the formula (III) with a compound of the formula (IV):

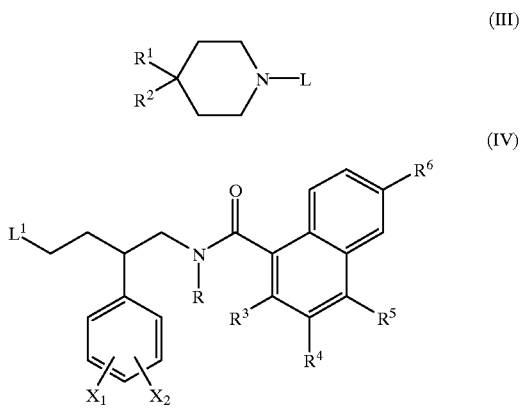

(III)

(IV)

wherein R, $R^1$–$R^6$, $X_1$ and $X_2$ are as defined in claim 1; and L and $L^1$ are groups such that reductive amination of the compounds of the formulae (III) and (IV) forms a N—C bond; or b) reacting a compound of the formula (V) with a compound of the formula (VI):

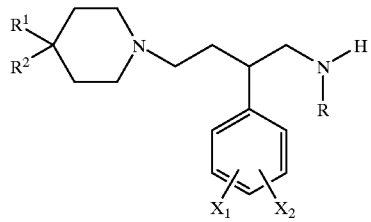

(V)

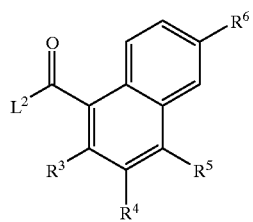

(VI)

wherein $R^1$–$R^6$, $R^2$, $X_1$ and $X_2$ are as defined in claim 1; and $L^2$ is a leaving group; wherein any other functional group is protected, if necessary, and:
i) removing any protecting groups;
ii) optionally forming a pharmaceutically acceptable salt or in vivo hydrolysable precursor.

\* \* \* \* \*

UNITED STATES PATENT AND TRADEMARK OFFICE
CERTIFICATE OF CORRECTION

PATENT NO. : 6,365,602 B1
DATED : April 2, 2002
INVENTOR(S) : Peter Bernstein, Robert Dedinas, Keith Russell and Ashokkumar Shenyl It is certified that error appears in the above-identified patent and that said Letters Patent is hereby corrected as shown below:

<u>Title page,</u>
Item [75], Inventors, the name of the fourth inventor "Ashokkumar Shenyl" should be -- Ashokkumar Shenvi --.

Signed and Sealed this

Twenty-ninth Day of October, 2002

*Attest:*

*Attesting Officer*

JAMES E. ROGAN
*Director of the United States Patent and Trademark Office*